United States Patent
Hwang et al.

(10) Patent No.: US 9,640,768 B2
(45) Date of Patent: May 2, 2017

(54) HETEROCYCLIC COMPOUND AND ORGAINIC LIGHT-EMITTING DEVICE INCLUDING THE SAME

(71) Applicant: SAMSUNG DISPLAY CO., LTD., Yongin, Gyeonggi-Do (KR)

(72) Inventors: Seok-Hwan Hwang, Yongin (KR); Young-Kook Kim, Yongin (KR); Jun-Ha Park, Yongin (KR); Hye-Jin Jung, Yongin (KR); Jin-O Lim, Yongin (KR); Eun-Young Lee, Yongin (KR); Sang-Hyun Han, Yongin (KR); Eun-Jae Jeong, Yongin (KR); Soo-Yon Kim, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 375 days.

(21) Appl. No.: 14/287,438

(22) Filed: May 27, 2014

(65) Prior Publication Data

US 2015/0001496 A1    Jan. 1, 2015

(30) Foreign Application Priority Data

Jun. 26, 2013   (KR) .................. 10-2013-0073960

(51) Int. Cl.
   *H01L 51/00* (2006.01)
   *H01L 51/50* (2006.01)
   (Continued)

(52) U.S. Cl.
   CPC ........ *H01L 51/0072* (2013.01); *C07D 405/04* (2013.01); *C07D 405/14* (2013.01);
   (Continued)

(58) Field of Classification Search
   None
   See application file for complete search history.

(56) References Cited

U.S. PATENT DOCUMENTS 7,429,372 B2    9/2008  Pez et al.
2012/0235123 A1  9/2012  Lee et al.
2014/0361258 A1* 12/2014 Hwang .................. C09K 11/06
                                                              257/40

FOREIGN PATENT DOCUMENTS

JP    2006-352046 A   12/2006
KR    10-2011-0015836 A   2/2011

OTHER PUBLICATIONS

M.A. Baldo et al.; Highly Efficient Phosphorescent Emission From Organic Electroluminescent Devices; Letters to Nature; vol. 395; Sep. 10, 1998; pp. 151-154.
Baldo et al.; Very High-Efficiency Green Organic Light-Emitting Devices Based on Electrophorescence; Applied Physics Letters; vol. 75; No. 1; Jul. 5, 1999; pp. 4-6.
Adachi et al.; High-Efficiency Organic Electrophosphorescent Devices with Tris (2-Phenylpyridine) Iridium Doped into Electron-Transporting Materials; Applied Physics Letters; vol. 77; No. 6; Aug. 7, 2000; pp. 904-906.

(Continued)

*Primary Examiner* — J. L. Yang
(74) *Attorney, Agent, or Firm* — Lee & Morse, P.C.

(57) ABSTRACT

A heterocyclic compound of Formula 1 and an organic light-emitting device including the same are provided.

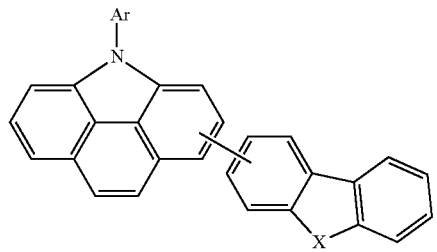

Ar and X in Formula 1 are defined as in the specification.

20 Claims, 1 Drawing Sheet

(51) Int. Cl.
    *C07D 405/14*     (2006.01)
    *C07D 405/04*     (2006.01)
    *C07D 409/04*     (2006.01)
    *C07D 409/14*     (2006.01)
    *C07F 7/08*     (2006.01)

(52) U.S. Cl.
    CPC ......... *C07D 409/04* (2013.01); *C07D 409/14* (2013.01); *C07F 7/0812* (2013.01); *H01L 51/0067* (2013.01); *H01L 51/0073* (2013.01); *H01L 51/0074* (2013.01); *H01L 51/0077* (2013.01); *H01L 51/006* (2013.01); *H01L 51/0085* (2013.01); *H01L 51/5016* (2013.01); *H01L 51/5072* (2013.01)

(56) References Cited

OTHER PUBLICATIONS

Kwong et al.; High Operational Stability of Electrophosphorescent Devices; Applied Physics Letters; vol. 81; No. 1; Jul. 1, 2002; pp. 162-164.

Oryong Hall; A Novel Conjugated Polymer Based on 4H-Benzo [def] Carbazole Backbone for OLED; Fall Assembly and Symposium; Gwangju Institute of Science and Technology; vol. 34; No. 2; Oct. 8-9, 2009.

Aldrich; H-Benzo [def] Carbazole; Sigma-Aldrich Internet Page, 2014.

\* cited by examiner

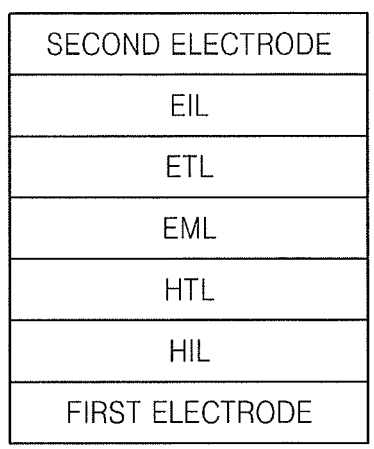

HETEROCYCLIC COMPOUND AND ORGAINIC LIGHT-EMITTING DEVICE INCLUDING THE SAME

CROSS-REFERENCE TO RELATED APPLICATION

The present application claims priority under 35 U.S.C. §119 to Korean Patent Application No. 10-2013-0073960, filed on Jun. 26, 2013, in the Korean Intellectual Property Office, and entitled: "Heterocyclic Compound and Organic Light-Emitting Device Including the Same," which is incorporated by reference herein in its entirety.

BACKGROUND

1. Field

One or more embodiments relate to a heterocyclic compound and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and the ability to provide multicolored images. A typical OLED has a structure including a substrate, and an anode, a hole transport layer (HTL), an emission layer (EML), an electron transport layer (ETL), and a cathode, which are sequentially stacked on the substrate. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted. There is an ongoing demand for a material having improved electrical stability, high charge-transport or emission capability, and a high glass transition temperature that is high enough to prevent crystallization, with regard to existing unimolecular materials.

SUMMARY

According to one or more embodiments, there is provided a heterocyclic compound represented by Formula 1:

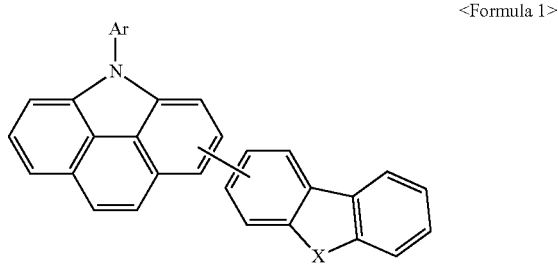

<Formula 1> wherein, in Formula 1, Ar is a hydrogen atom, a deuterium atom, a substituted, or an unsubstituted $C_1$-$C_{60}$ alkyl group, a substituted or unsubstituted $C_3$-$C_{60}$ cycloalkyl group, a substituted or unsubstituted $C_2$-$C_{60}$ heteroaryl group, a substituted or unsubstituted $C_6$-$C_{60}$ aryl group, or a substituted or unsubstituted $C_6$-$C_{60}$ condensed polycyclic group; and X is O or S.

According to one or more embodiments, an organic light-emitting device includes a first electrode, a second electrode, and an organic layer disposed between the first electrode and the second electrode. The organic layer includes the above-described heterocyclic compound of Formula 1.

According to one or more embodiments, a flat panel display device includes an organic light-emitting device described herein. The first electrode of the organic light-emitting device is electrically connected to a source electrode or a drain electrode of a thin-film transistor.

BRIEF DESCRIPTION OF THE DRAWING

These and/or other aspects will become apparent and more readily appreciated from the following description of the embodiments, taken in conjunction with the accompanying drawing of which: FIG. 1 illustrates a schematic view of a structure of an organic light-emitting device according to an embodiment.

DETAILED DESCRIPTION

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "and/or" includes any and all combinations of one or more of the associated listed. Expressions such as "at least one of," when preceding a list of elements, modify the entire list of elements and do not modify the individual elements of the list.

According to an aspect, there is provided a heterocyclic compound represented by Formula 1:

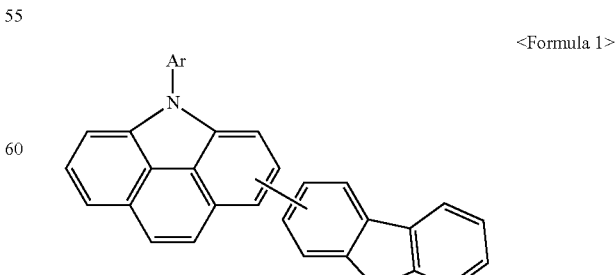

<Formula 1>

In Formula 1, Ar is a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_2$-$C_{60}$ heteroaryl group, a substituted or unsubstituted $C_6$-$C_{60}$ aryl group, or a substituted or unsubstituted $C_6$-$C_{60}$ condensed polycyclic group; and X is O or S.

In some embodiments, the heterocyclic compound of Formula 1 may serve as a light-emitting material or an electron transporting material for organic light-emitting devices. The heterocyclic compound of Formula 1 may have a high glass transition temperature (Tg) or melting point due to introduction of the heterocyclic group. Thus, the heterocyclic compound may have high heat resistance against Joule's heat generated in an organic layer, between organic layers, or between an organic layer and a metal electrode when light emission occurs, and have high durability in high-temperature environments. An organic light-emitting device manufactured using the heterocyclic compound of Formula 1, according to an embodiment, may have high durability when stored or operated.

The compound of Formula 1 may be a compound represented by Formula 2 or 3, Ar and X may be defined as described with respect to Formula 1.

<Formula 2>

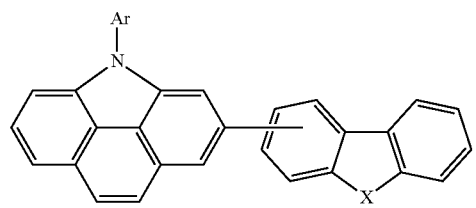

<Formula 3>

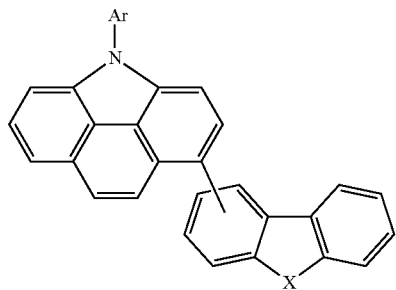

In some embodiments, Ar in Formula 1 may be a group represented by one of Formulae 2a to 2d.

2a

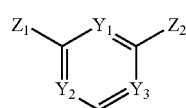

2b

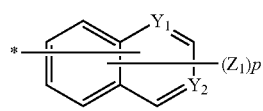

2c

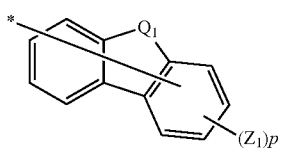

2d

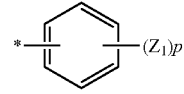

In Formulae 2a to 2d, $Y_1$, $Y_2$, and $Y_3$ may be each independently CH or N; $Q_1$ may be O, or —NR50-; $Z_1$, $Z_2$, and $R_{50}$ may be each independently a hydrogen atom, a deuterium atom, a substituted or unsubstituted $C_1$-$C_{20}$ alkyl group, a $C_1$-$C_{20}$ alkylsilyl group, a $C_6$-$C_{20}$ arylsilyl group, a substituted or unsubstituted $C_6$-$C_{20}$ aryl group, a substituted or unsubstituted $C_2$-$C_{20}$ heteroaryl group, a substituted or unsubstituted C6-C20 condensed polycyclic group, an amino group substituted with a C6-C20 aryl group or a $C_2$-$C_{20}$ heteroaryl group, a halogen group, a cyano group, a nitro group, a hydroxy group, or a carboxyl group; p may be an integer from 1 to 7; and * indicates a binding site.

For example, Ar in Formula 1 may be a group represented by one of Formulae 3a to 3i:

3a

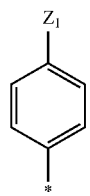

3b

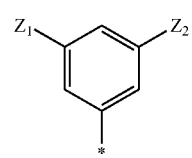

3c

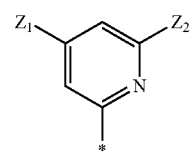

3d

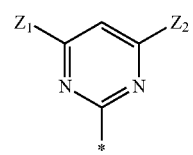

3e

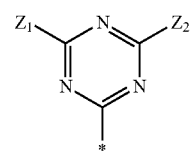

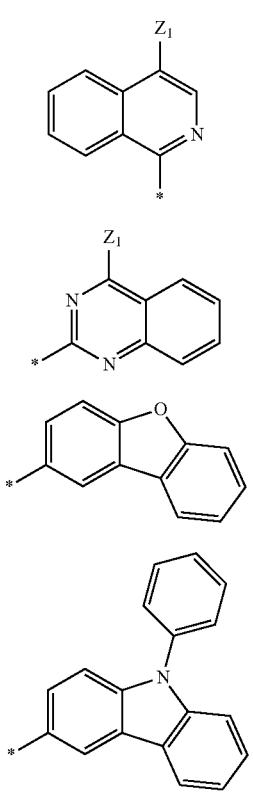

In Formulae 3a to 3i, $Z_1$ and $Z_2$ may be each independently a hydrogen atom, a deuterium atom, a substituted or unsubstituted $C_1$-$C_{20}$ alkyl group, a $C_1$-$C_{20}$ alkylsilyl group, a $C_6$-$C_{20}$ arylsilyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, an amino group substituted with a $C_6$-$C_{20}$ aryl group or a $C_2$-$C_{20}$ heteroaryl group, a halogen group, a cyano group, a nitro group, a hydroxy group, or a carboxyl group; and * indicates a binding site.

Hereinafter, substituents described with reference to the formulae will now be described in detail. In this regard, the numbers of carbons in substituents are presented only for illustrative purposes and do not limit the characteristics of the substituents. The substituents not defined herein are construed as the same meanings understood by one of ordinary skill in the art.

The unsubstituted $C_1$-$C_{60}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, an alkylsilyl group, an arylsilyl group, or a $C_2$-$C_{16}$ heteroaryl group.

The unsubstituted $C_2$-$C_{60}$ alkenyl group indicates an unsaturated alkyl groups having at least one carbon-carbon double bond in the center or at a terminal of the alkyl group. Examples of the alkenyl group are an ethenyl group, a propenyl group, and a butenyl group. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Non-limiting examples of the unsubstituted $C_2$-$C_{20}$ alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted $C_3$-$C_{60}$ cycloalkyl group indicates a $C_3$-$C_{60}$ cyclic alkyl group wherein at least one hydrogen atom in the cycloalkyl group may be substituted with a substituent described above in conduction with the $C_1$-$C_{60}$ alkyl group.

The unsubstituted $C_1$-$C_{60}$ alkoxy group indicates a group having a structure of —OA wherein A is an unsubstituted $C_1$-$C_{60}$ alkyl group as described above. Non-limiting examples of the unsubstituted $C_1$-$C_{60}$ alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_6$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted $C_1$-$C_{60}$ alkyl group.

Non-limiting examples of the substituted or unsubstituted $C_6$-$C_{60}$ aryl group are a phenyl group, a $C_1$-$C_{10}$ alkylphenyl group (for example, an ethylphenyl group), a biphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N-dimethyl)aminophenyl group, a (N,N'-diphenyl)aminophenyl group, a pentalenyl group, an indenyl group, a naphthyl group, a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, an azulenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_2$-$C_{60}$ heteroaryl group used herein includes one, two, three, or four heteroatoms selected from N, O, P and S. At least two rings may be fused to each other or linked to each other by a single bond. Non-limiting examples of the unsubstituted $C_4$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{60}$ alkyl group.

The unsubstituted $C_6$-$C_{60}$ aryloxy group is a group represented by —$OA_1$, wherein $A_1$ may be a $C_6$-$C_{60}$ aryl group. An example of the aryloxy group is a phenoxy group. At least one hydrogen atom in the aryloxy group may be substituted with a substituent described above in conjunction with the unsubstituted C1-C60 alkyl group.

The unsubstituted $C_6$-$C_{60}$ arylthio group is a group represented by -$SA_1$, wherein $A_1$ may be a $C_6$-$C_{60}$ aryl group. Non-limiting examples of the arylthio group are a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted $C_6$-$C_{60}$ condensed polycyclic group is distinct from an aryl group or a heteroaryl group in terms of being non-aromatic.

Examples of the heterocyclic compound of Formula 1 include Compounds 1 to 90.

1

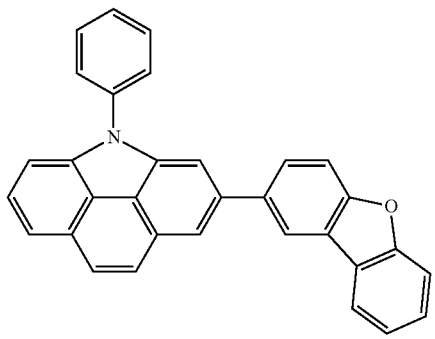

2

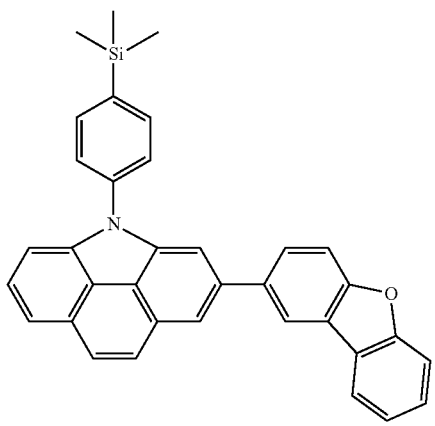

3

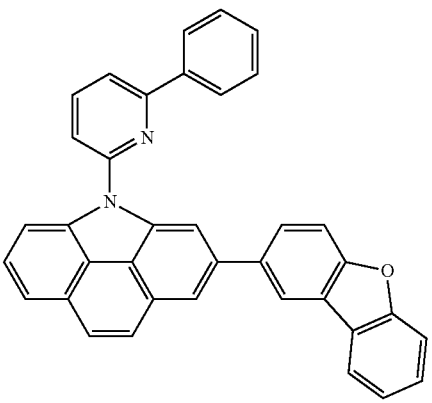

-continued

4

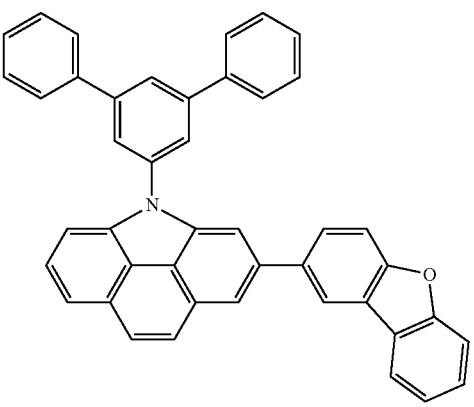

5

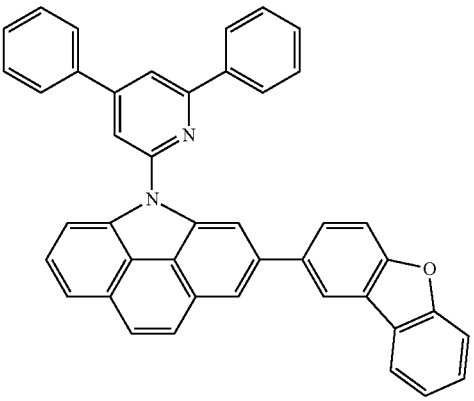

6
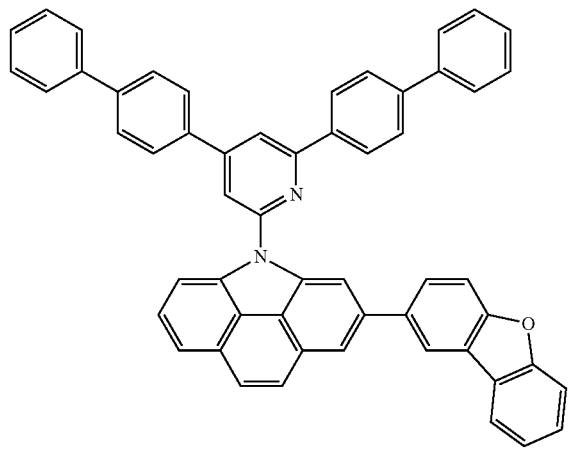
7
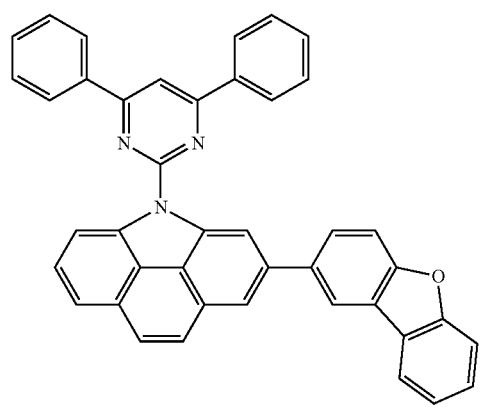
8
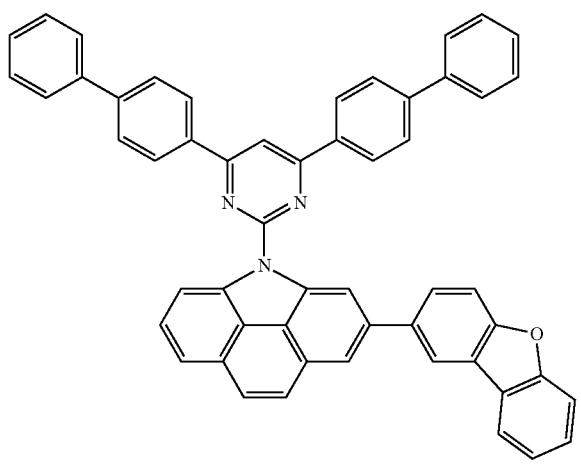
9
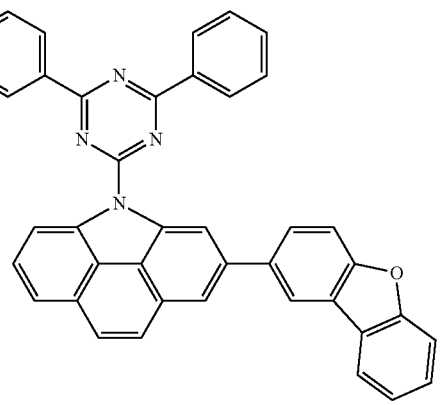
10
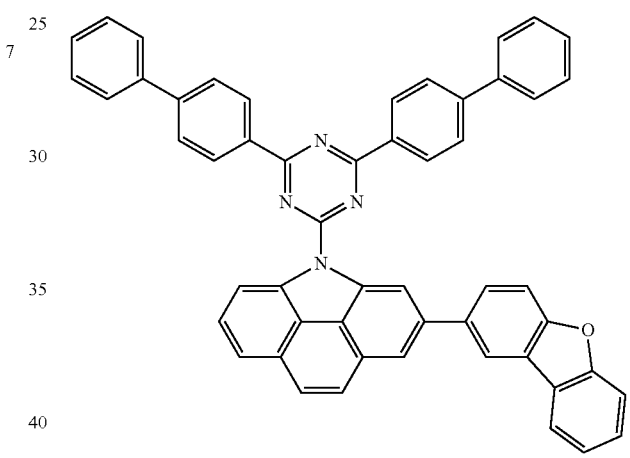
11
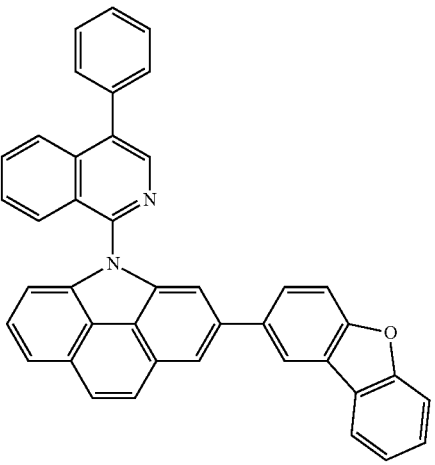

-continued
12
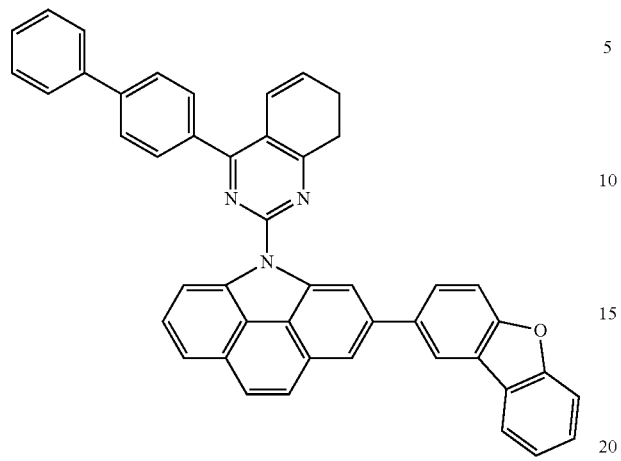
13
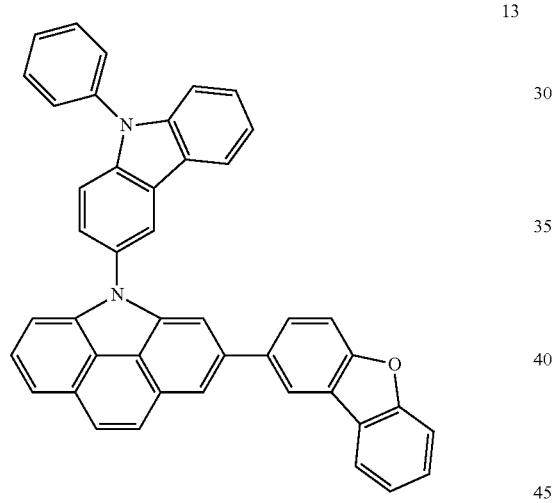
14
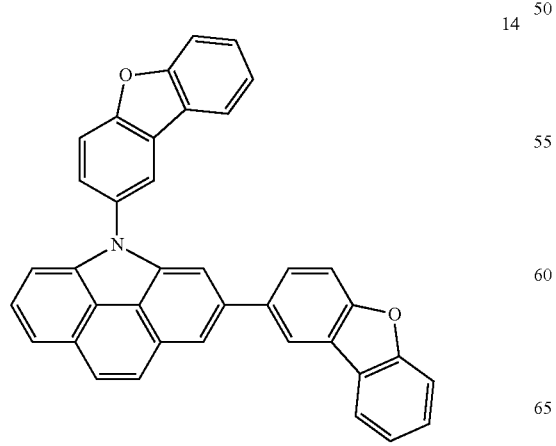
-continued
15
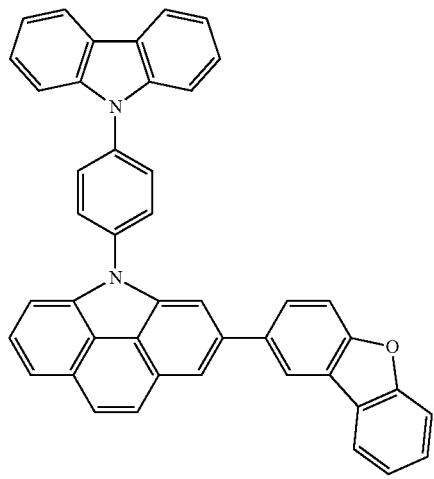
16
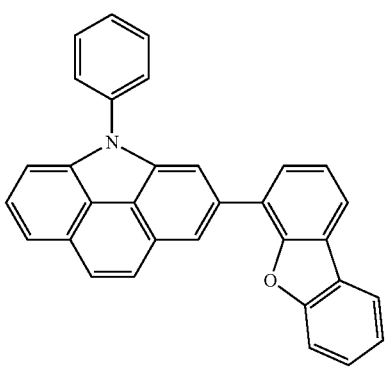
17
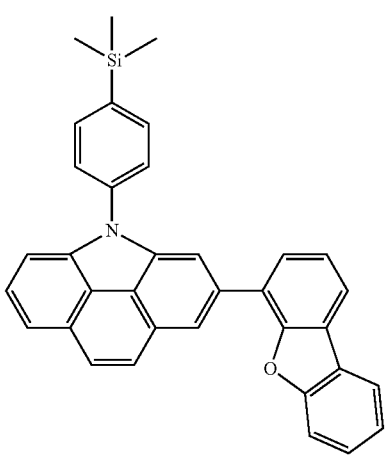

18
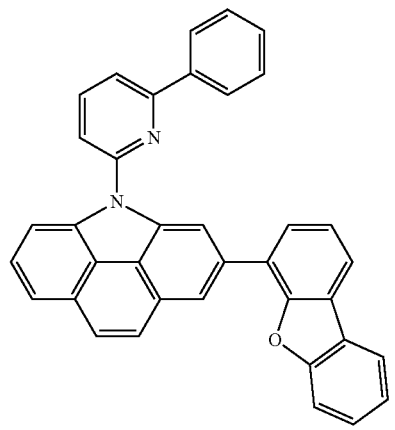
19
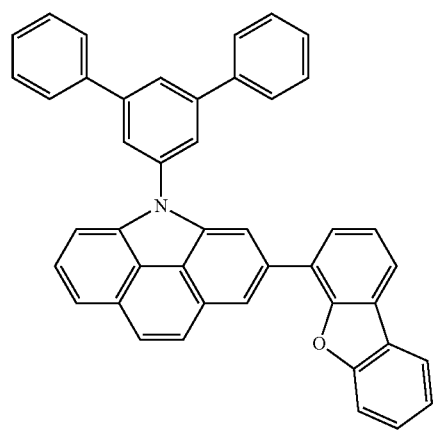
20
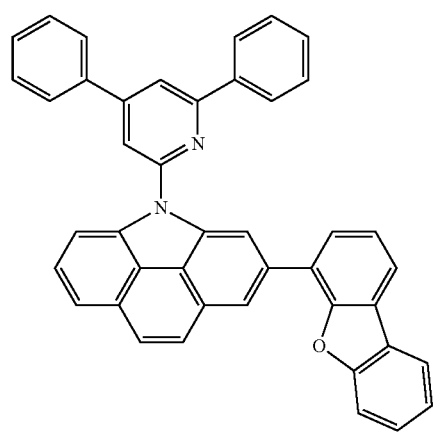
21
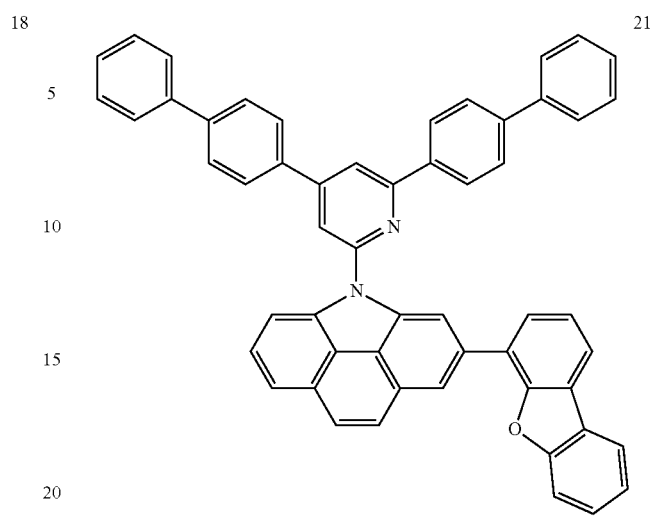
22
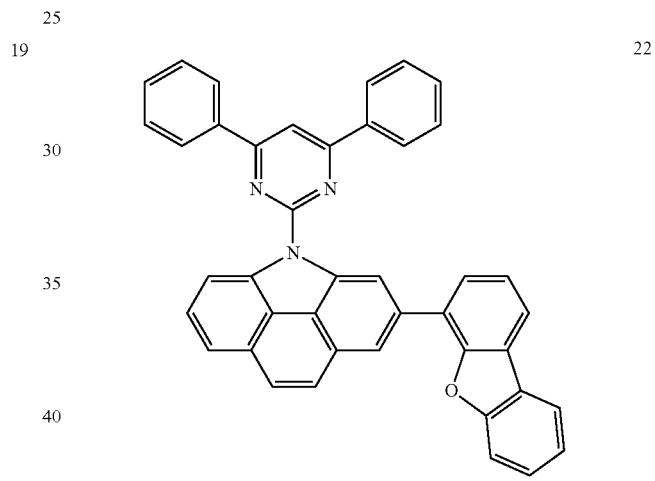
23
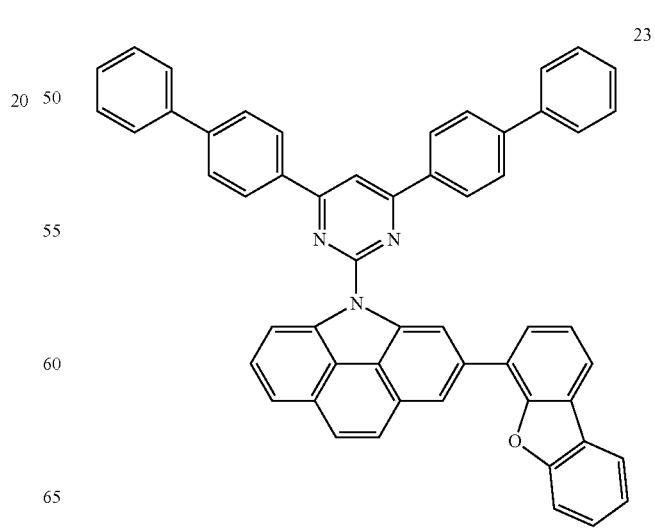

-continued
24
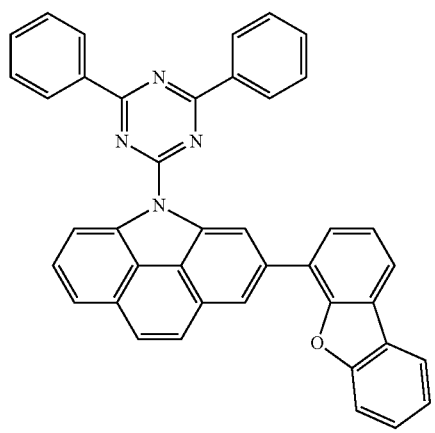
25
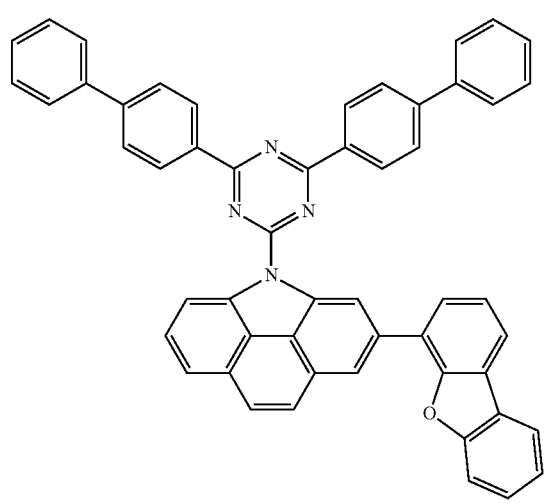
26
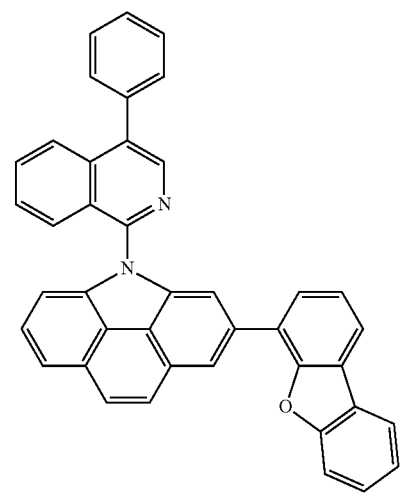
-continued
27
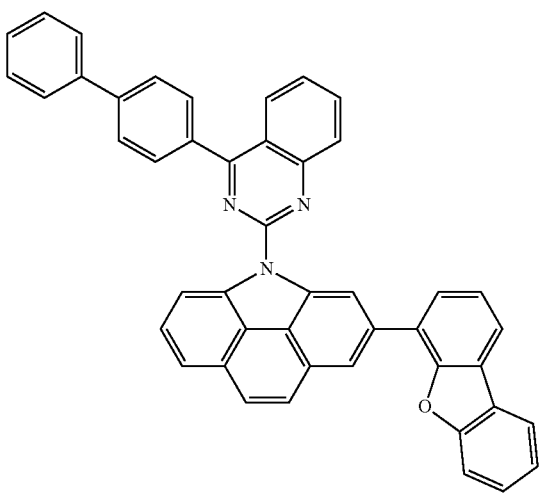
28
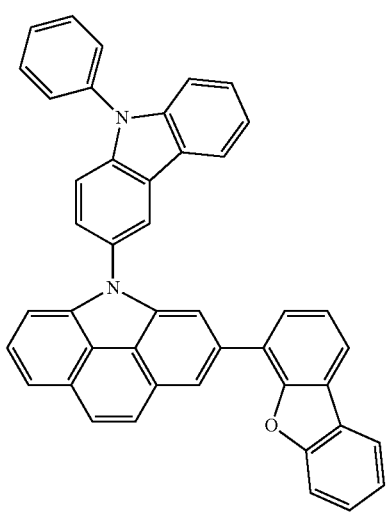
29
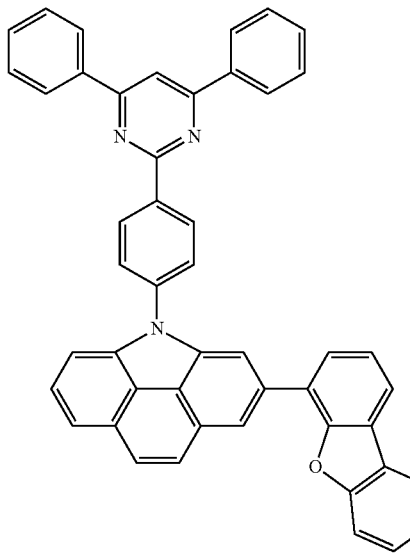

17
-continued
30
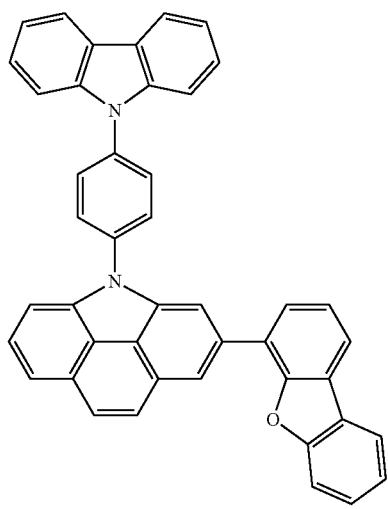
31
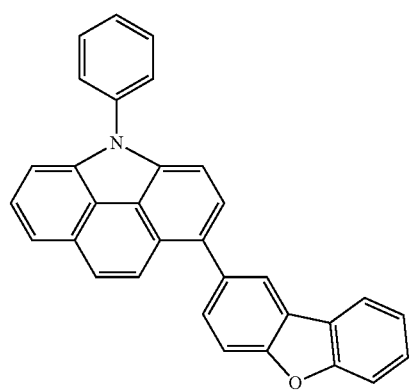
32
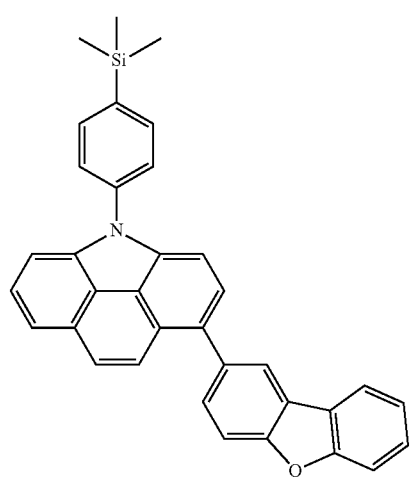
18
-continued
33
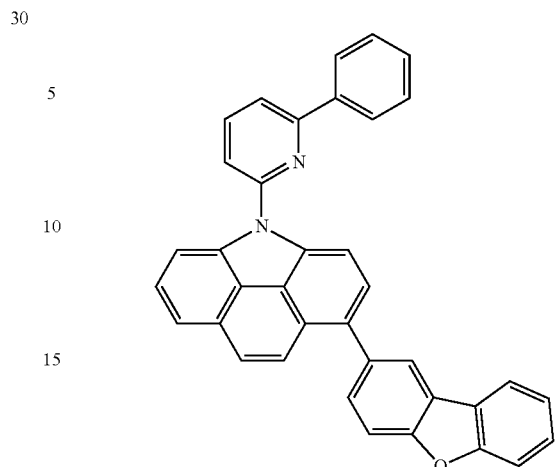
34
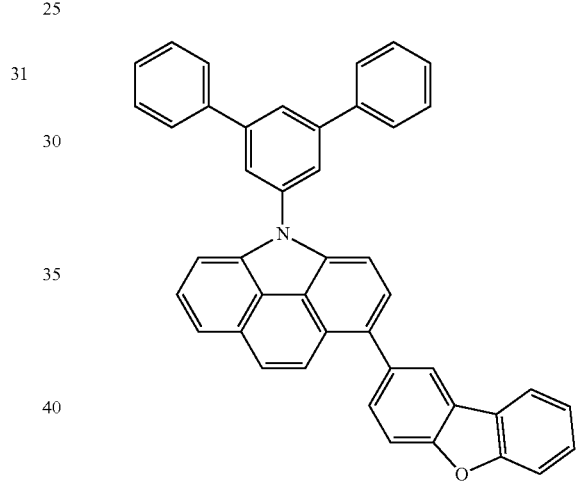
35
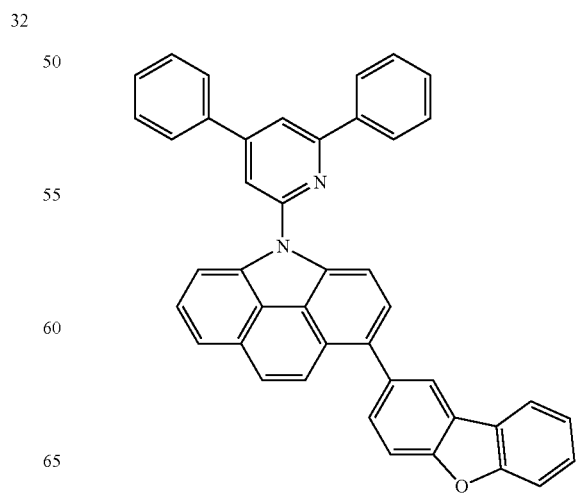

36
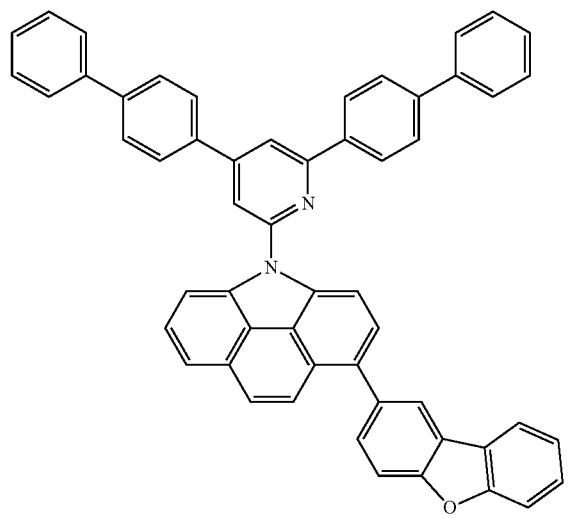
37
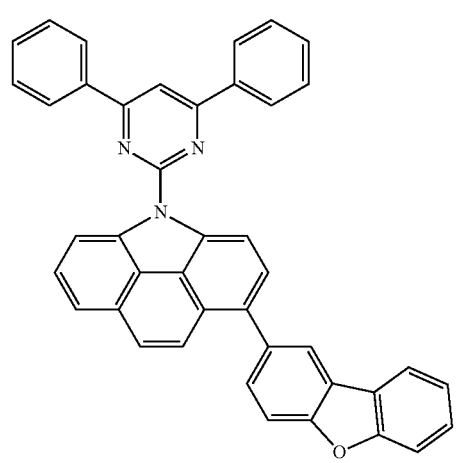
38
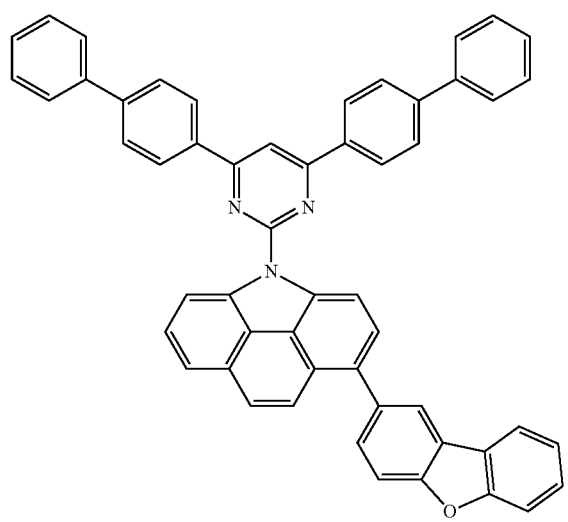
39
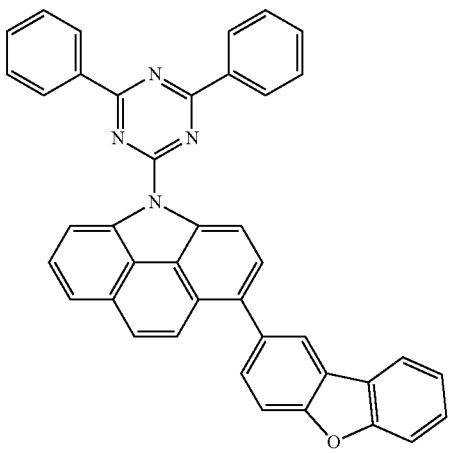
40
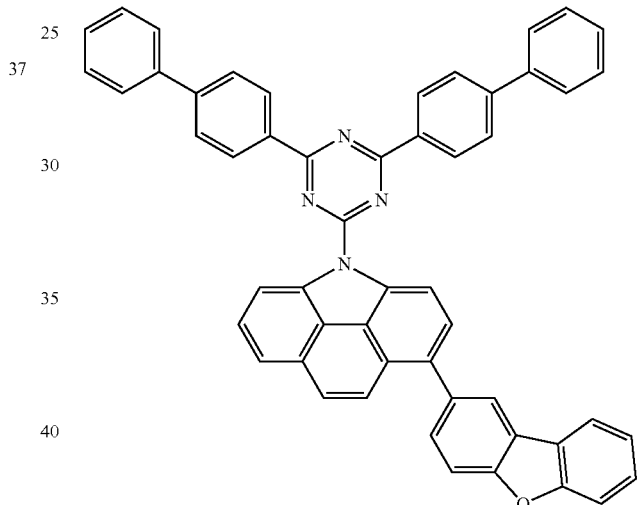
41
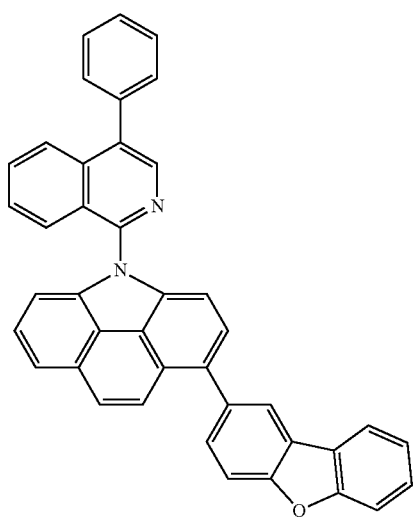

42
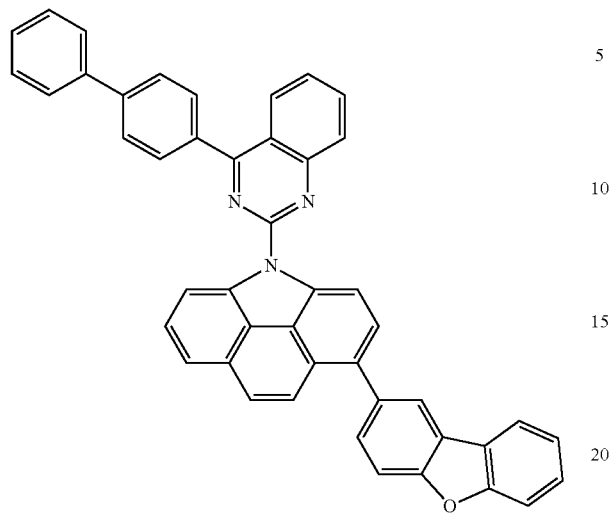
43
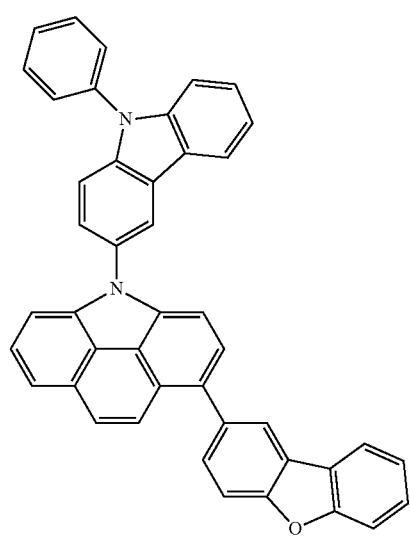
44
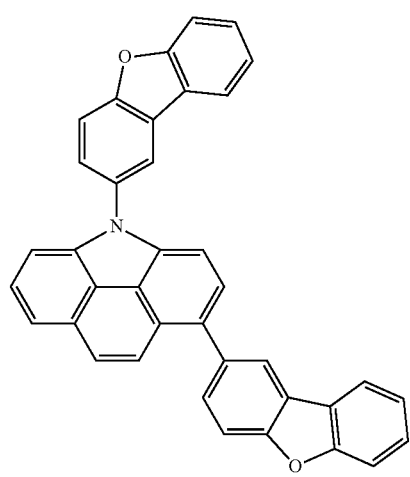
45
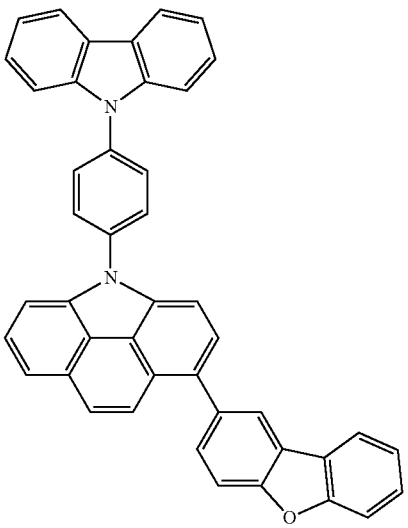
46
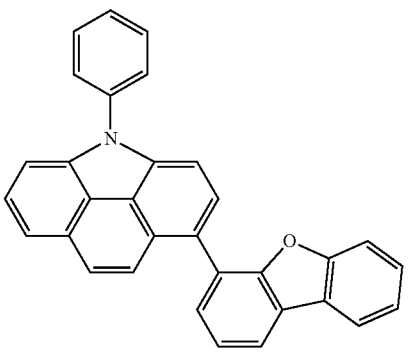
47
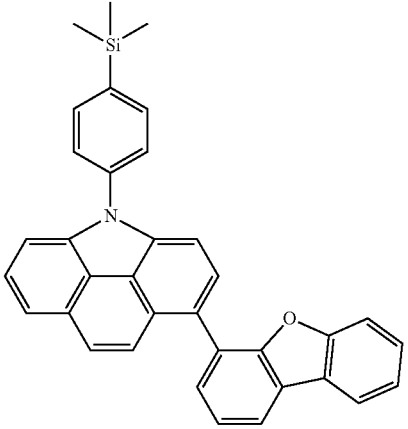

48
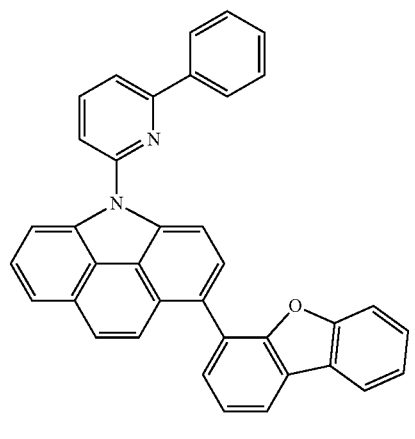
49
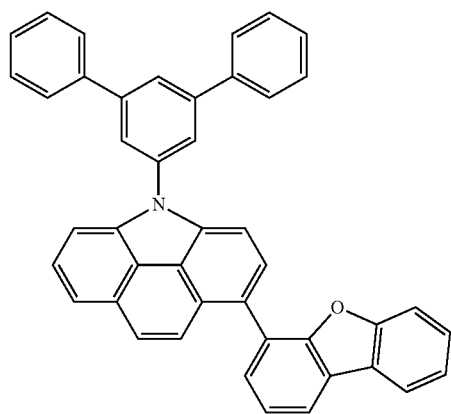
50
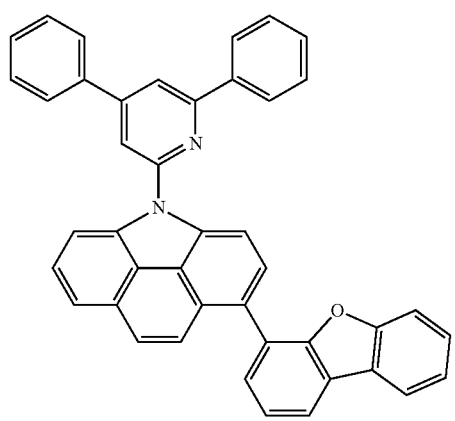
51
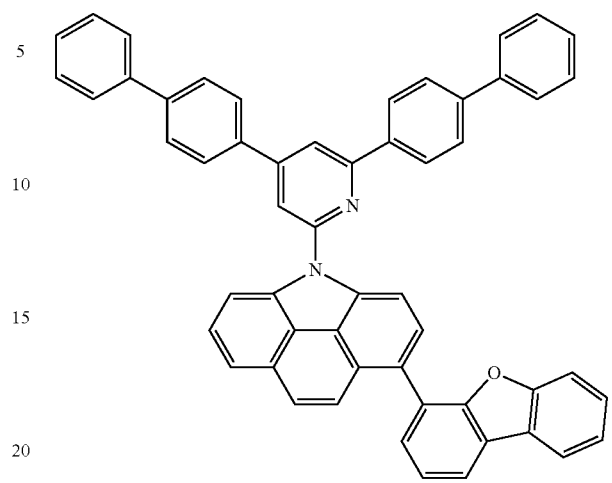
52
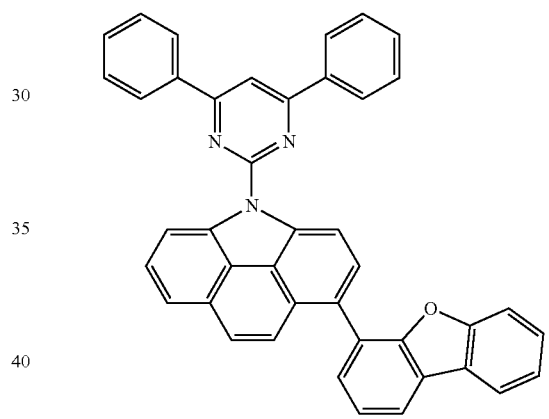
53
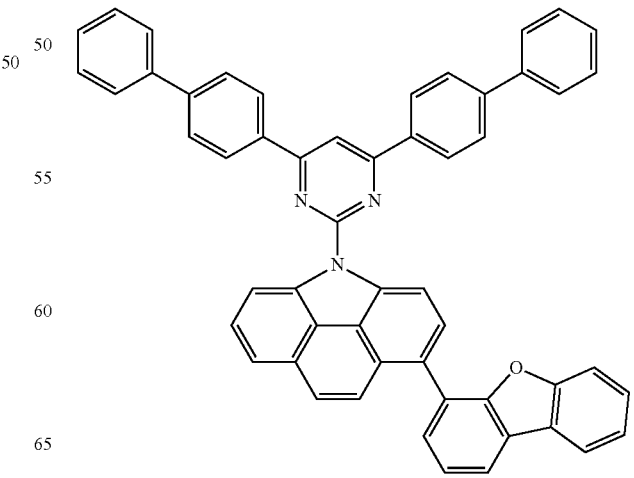

-continued
54
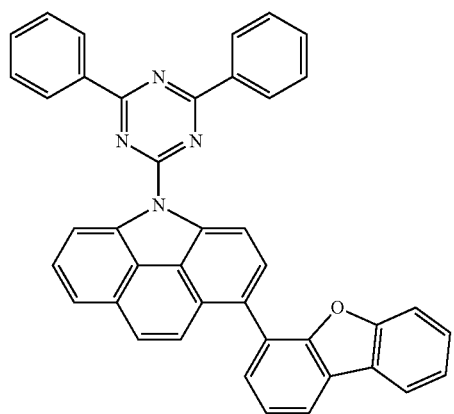
55
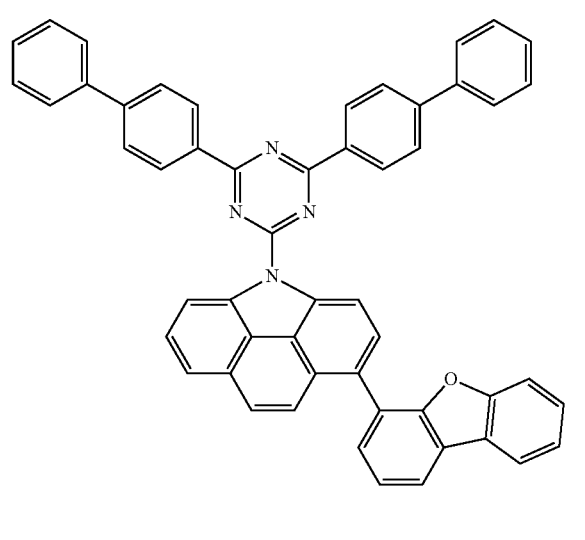
56
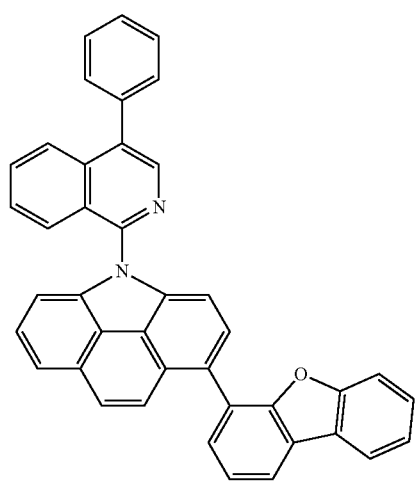
-continued
57
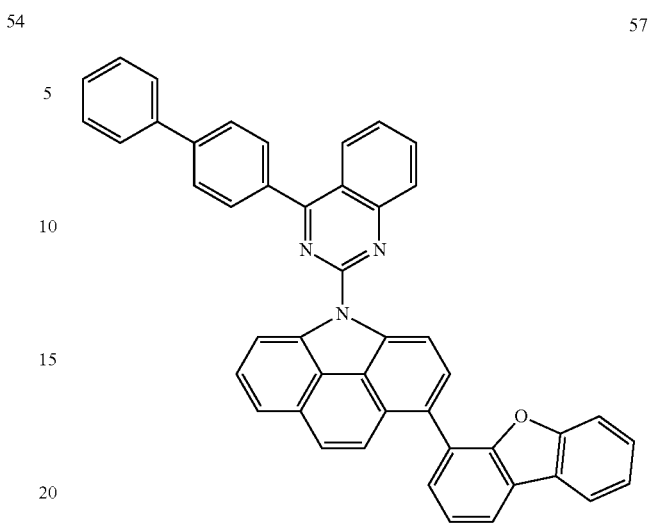
58
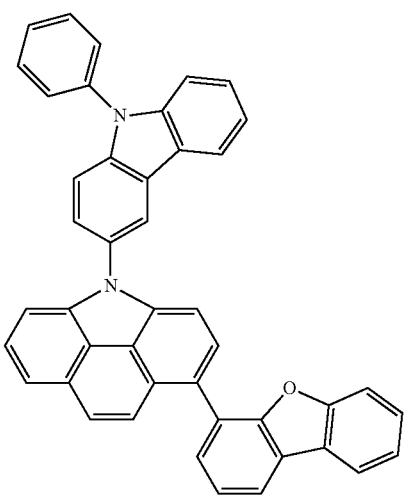
59
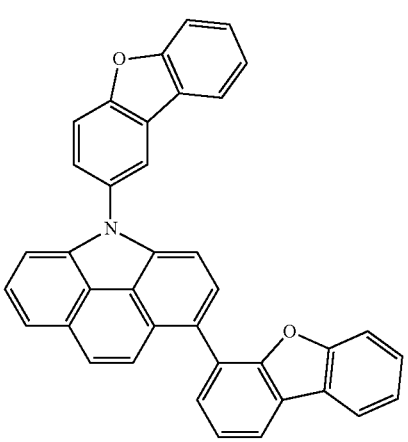

27
-continued
60
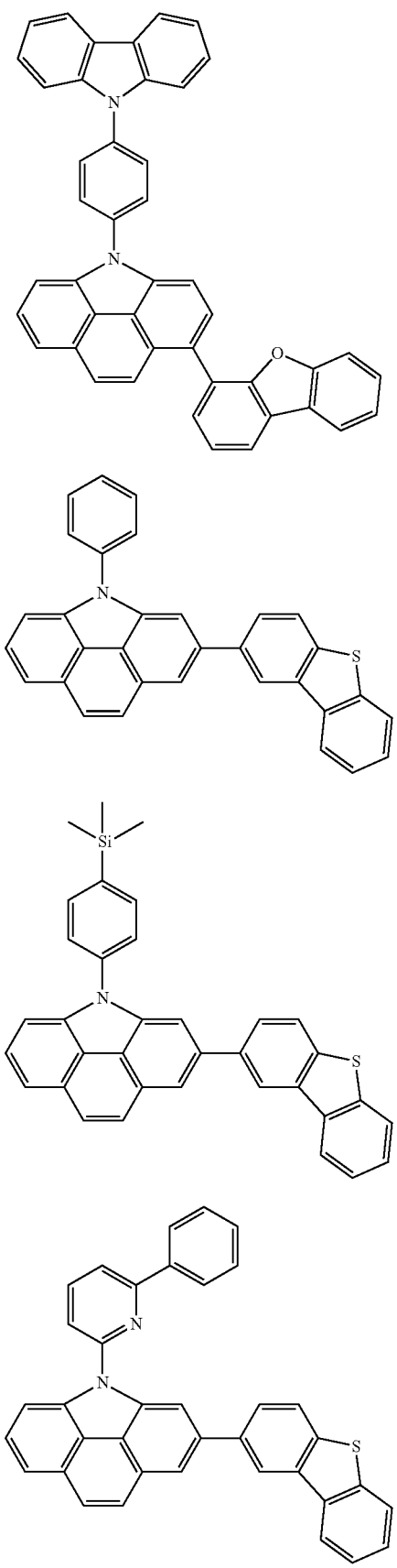
61
62
63
28
-continued
64
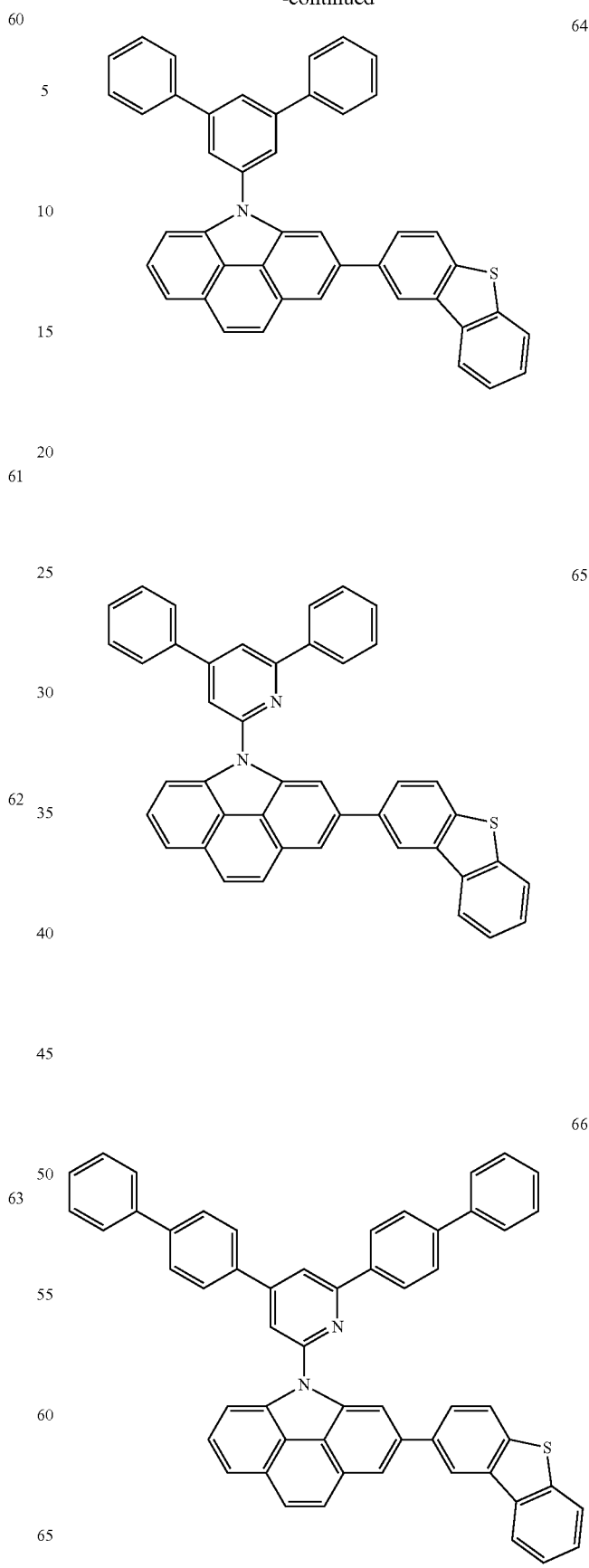
65
66

67
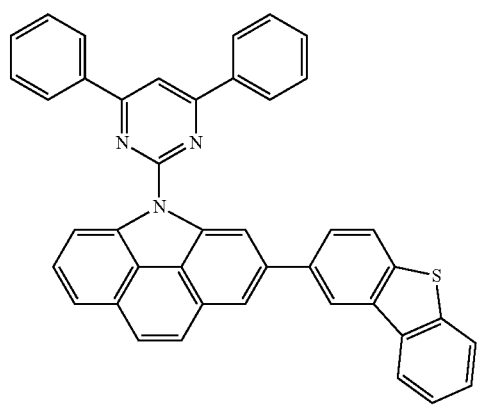
68
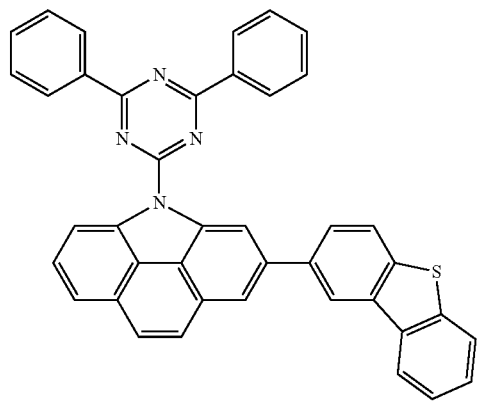
69
70
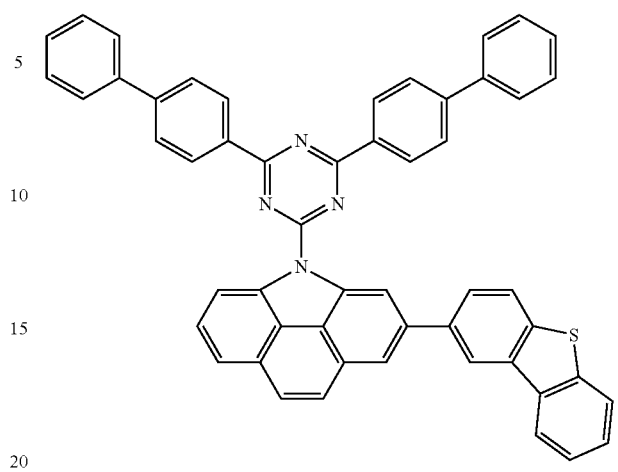
71
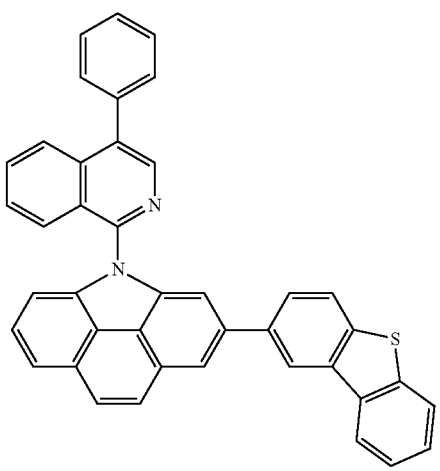
72
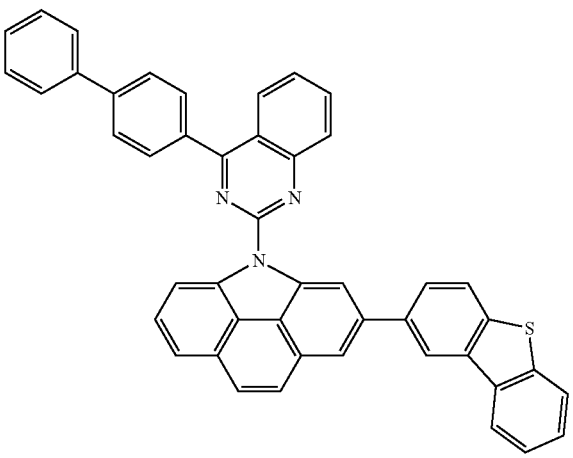

31
-continued
73
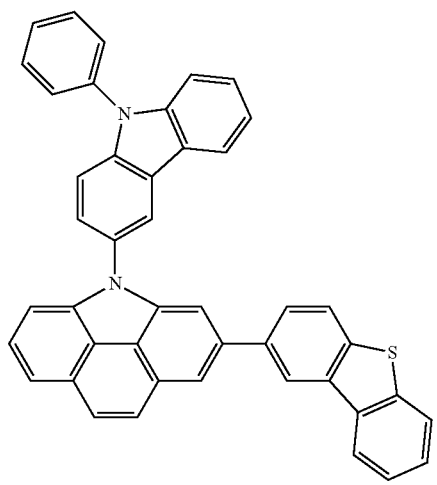
74
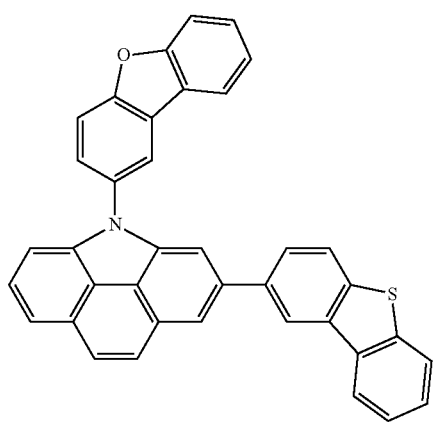
75
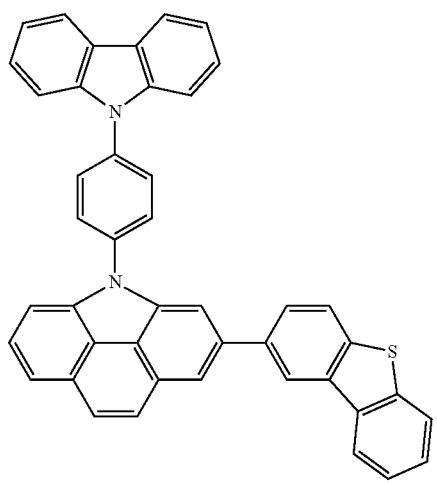
32
-continued
76
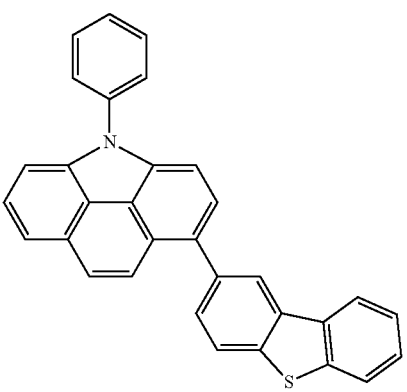
77
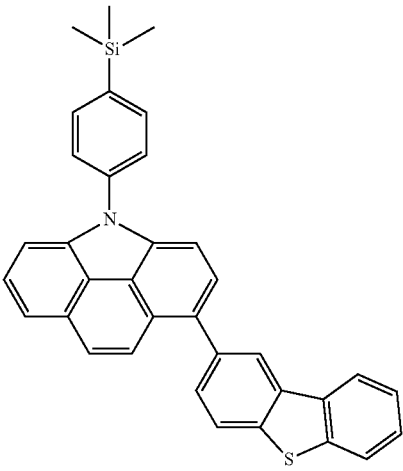
78
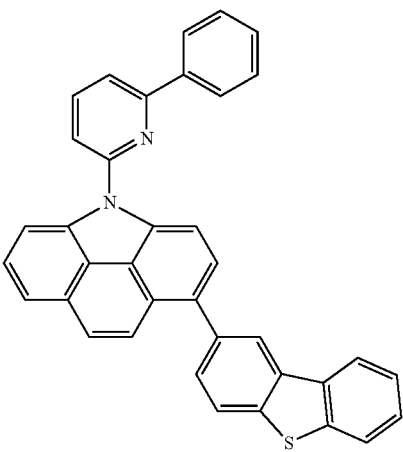

33
-continued
34
-continued
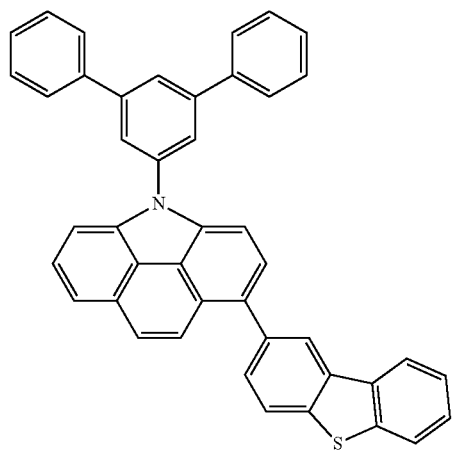
79
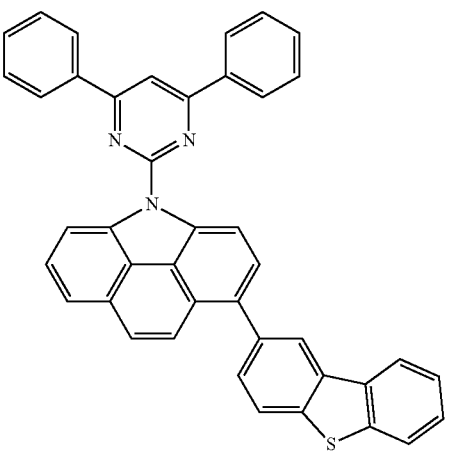
82
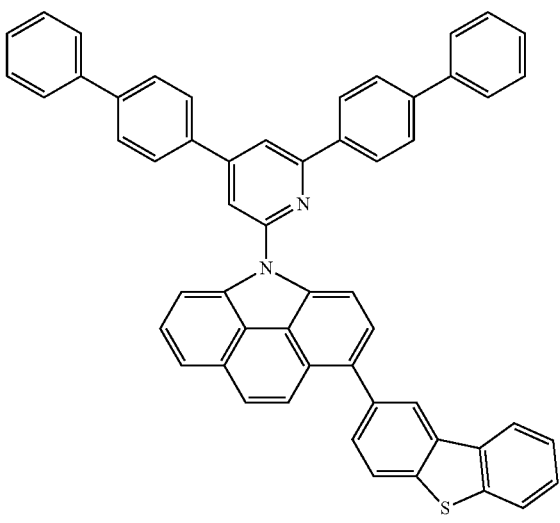
80
81
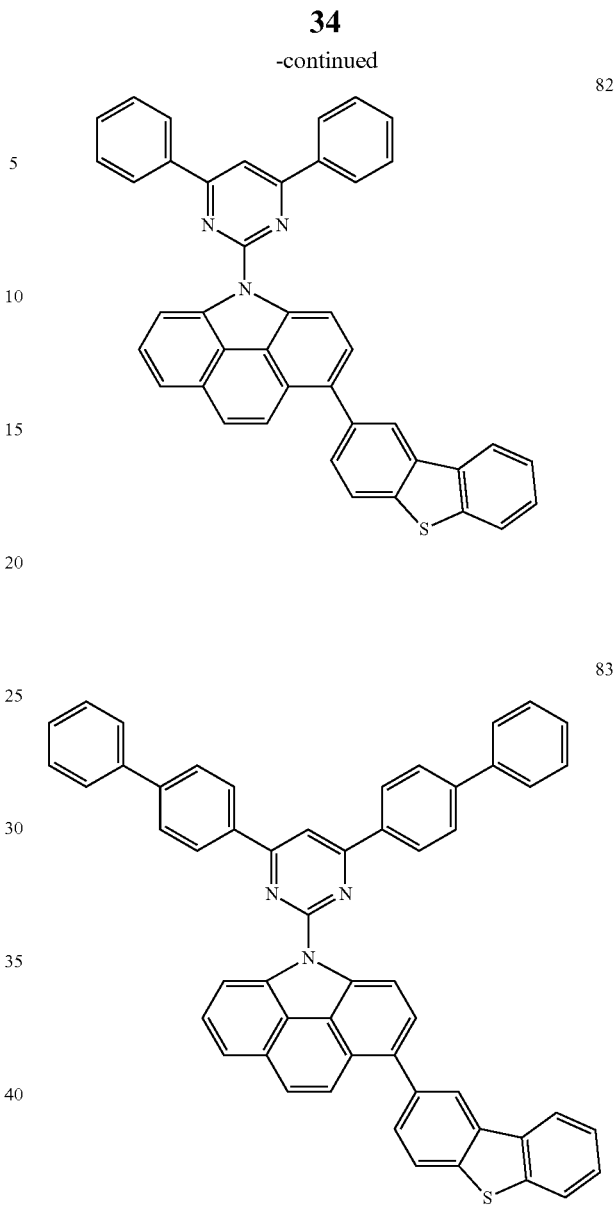
83
84
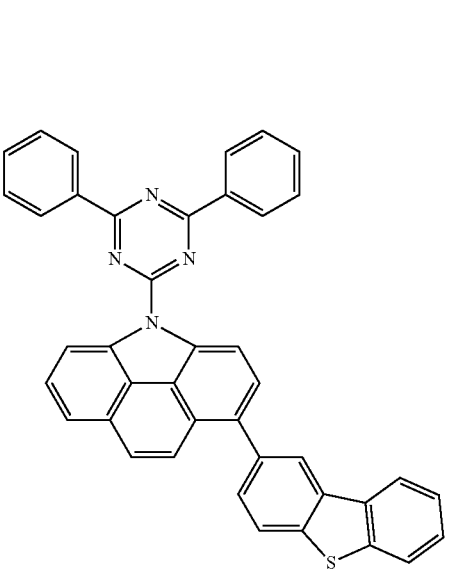

85
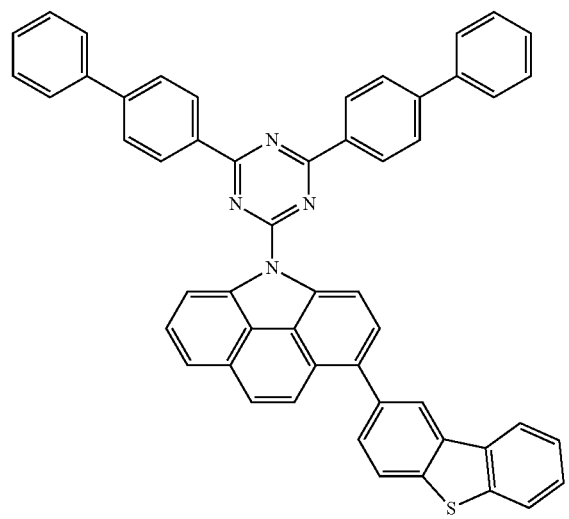
86
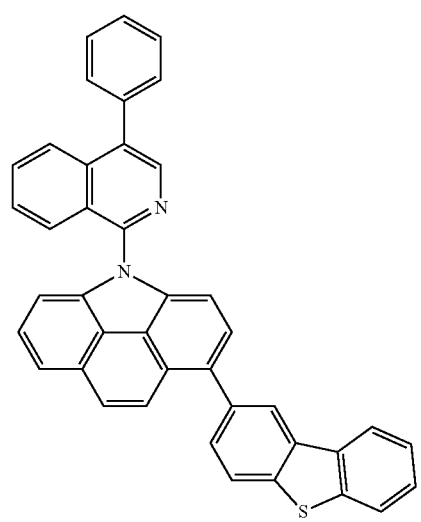
87
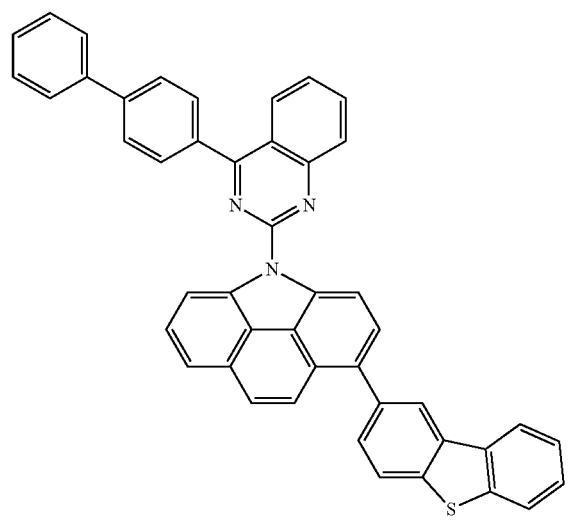
88
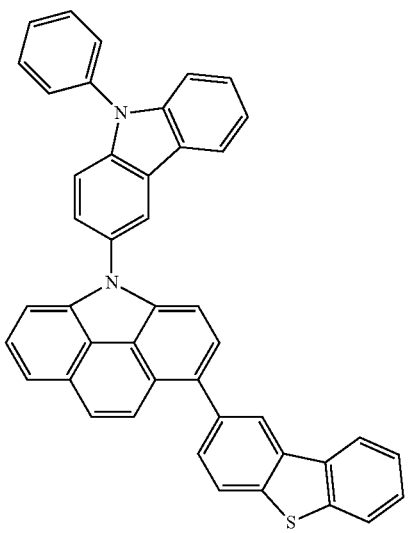
89
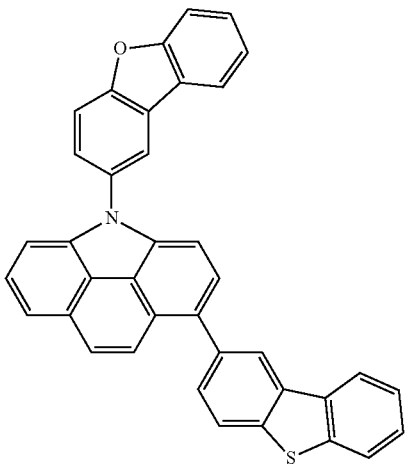
90
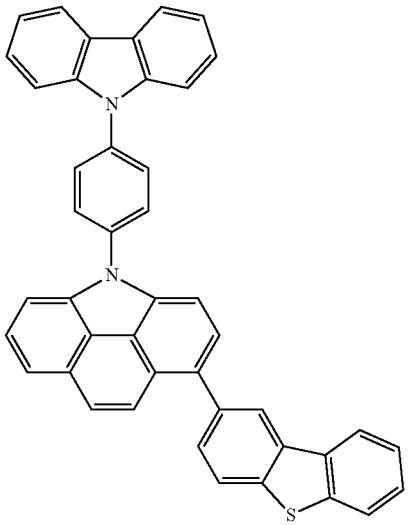
According to another aspect, an organic light-emitting device includes a first electrode, a second electrode, and an organic layer disposed between the first electrode and the second electrode, wherein the organic layer includes the heterocyclic compound of Formula 1.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer"). For example, the organic layer may be an emission layer or an electron transporting layer.

In some embodiments, the organic layer may include an electron injection layer, an electron transport layer, an emission layer, a hole injection layer, a hole transport layer, or a functional layer having both hole injection and transport capabilities, and the emission layer may include an anthracene-based compound, an arylamine-based compound, or a styryl-based compound.

In some other embodiments, the organic layer may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material.

In some embodiments, the charge-generating material may be a p-type dopant, and the p-type dopant may be a quinine derivative, a metal oxide or a cyano group-containing compound. In some embodiments, the organic film may include an electron transport layer, and the electron transport layer may include an electron-transporting organic compound and a metal complex. The metal complex may be a lithium (Li) complex.

The term "organic layer" and/or "organic film" as used herein refers to a single layer and/or a plurality of layers disposed between the first and second electrodes of the organic light-emitting device. The organic film may include an emission layer, and the emission layer may include the compound of Formula 1. The organic film may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

FIG. 1 illustrates a schematic sectional view of an organic light-emitting device according to an embodiment. A structure of an organic light-emitting device according to an embodiment and a method of manufacturing the same are described with reference to FIG. 1.

A substrate may be any suitable substrate that is used in an organic light emitting device. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode may have a single-layer structure or a multi-layer structure including at least two layers. For example, the first electrode may have a three-layered structure of ITO/Ag/ITO.

An organic layer(s) is disposed on the first electrode. The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like. When the HIL is formed using vacuum deposition, vacuum deposition conditions may vary depending on the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. When the HIL is formed using spin coating, the coating conditions may vary depending on the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C.

The HIL may be formed of a suitable material for a HIL. Examples of the material that can be used to form the HIL include N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and polyaniline)/poly(4-styrene-sulfonate) (PANI/PSS).

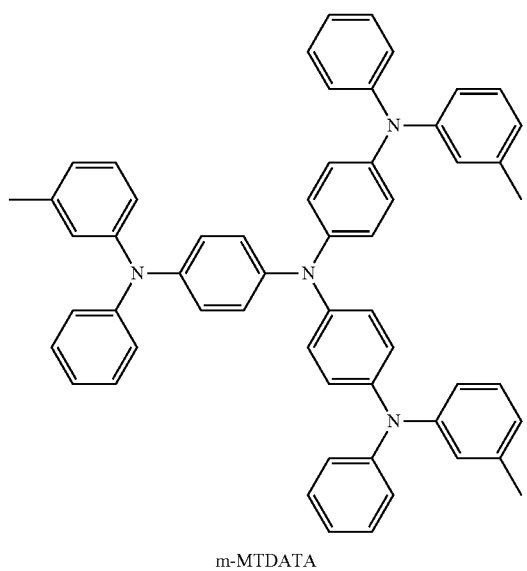

m-MTDATA

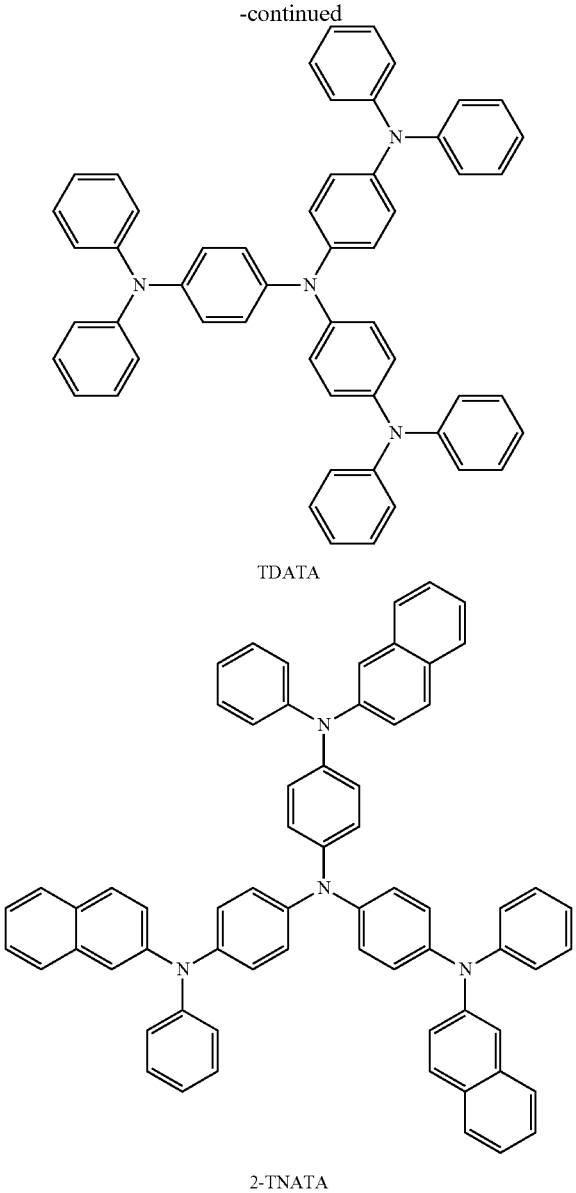

TDATA

2-TNATA

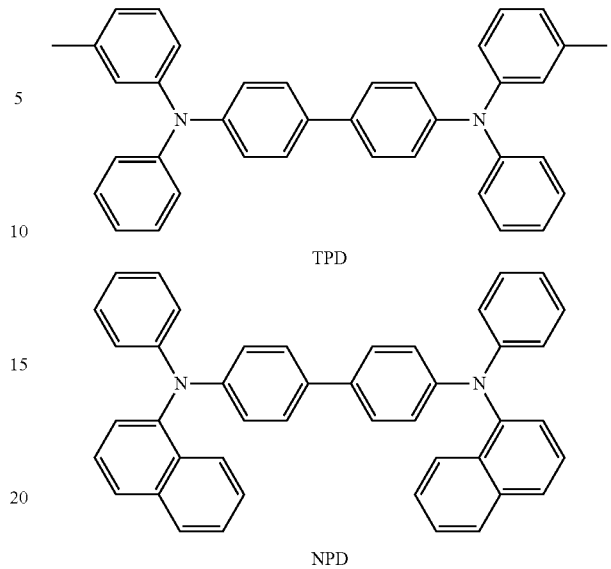

TPD

NPD

The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 and a compound of Formula 350:

<Formula 300>

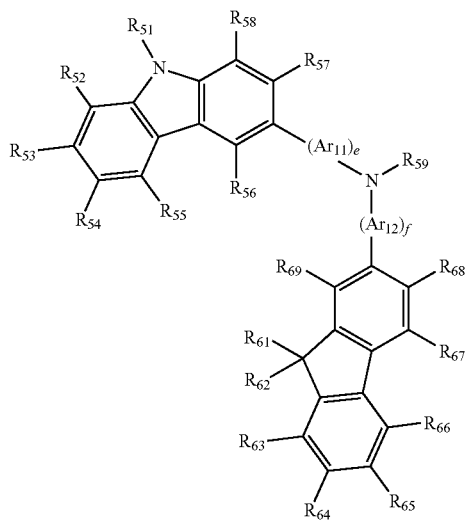

The thickness of the HIL may be about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary depending on the material that is used to form the HTL.

The HTL may be formed of any suitable hole-transporting materials. Examples of suitable HTL forming materials include carbazole derivatives, such as N-phenylcarbazole or polyvinylcarbazole, N,N'-bis(3-methylphenyl)-N,N-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

<Formula 350>

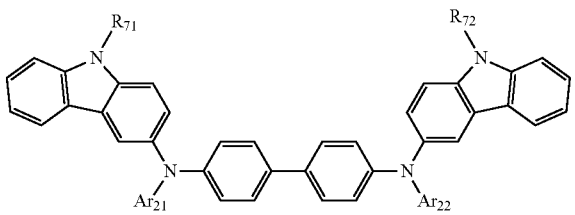

In Formulae 300 and 350, $Ar_{11}$, $Ar_{12}$, $Ar_2$, and $Ar_{22}$ may be each independently a substituted or unsubstituted $C_5$-$C_{60}$ arylene group. In Formula 300, e and f may be each independently an integer from 0 to 5, for example, may be 0, 1, or 2. For example, e may be 1, and f may be 0.

In Formulae 300 and 350, $R_{51}$ to $R_{58}$, $R_{61}$ to $R_{69}$, and $R_{71}$ and $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl) group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{109}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A:

<Formula 300A>

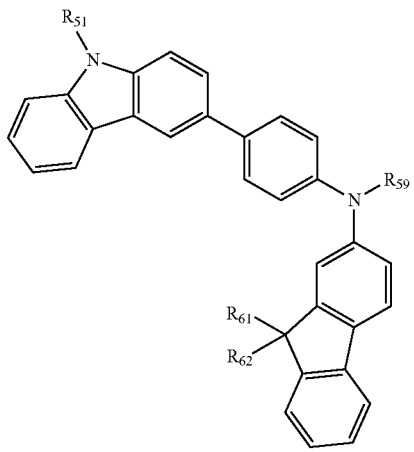

In Formula 300A, $R_{51}$, $R_{61}$, $R_{62}$, and $R_{59}$ may be as defined herein.

In some embodiments, for example, at least one of the HIL, HTL, and H-functional layer may include at least one of the compounds represented by Formulae 301 to 320:

301

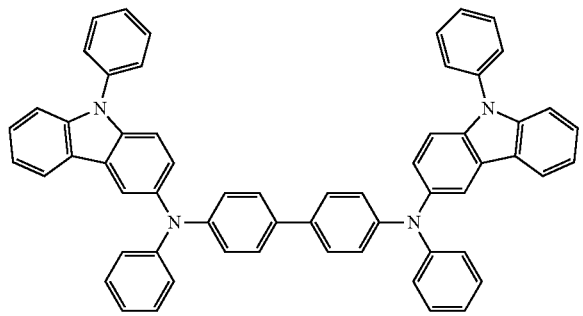

302

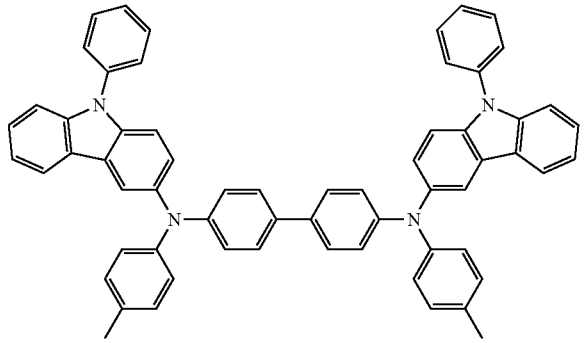

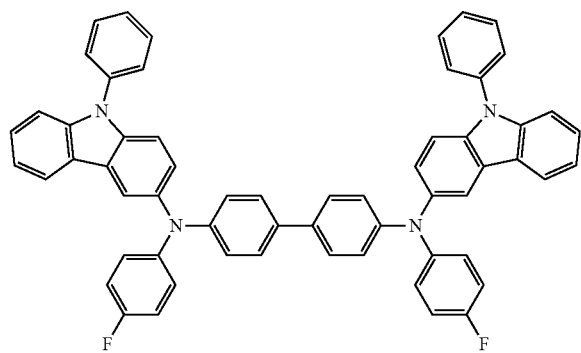
303
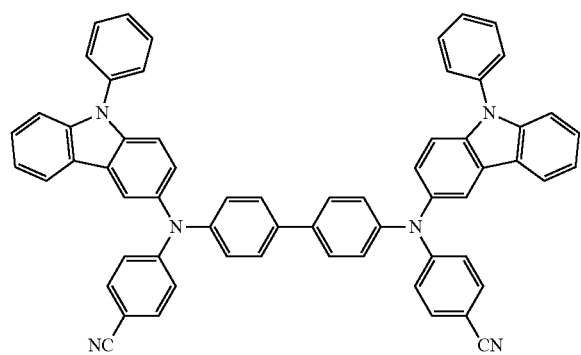
304
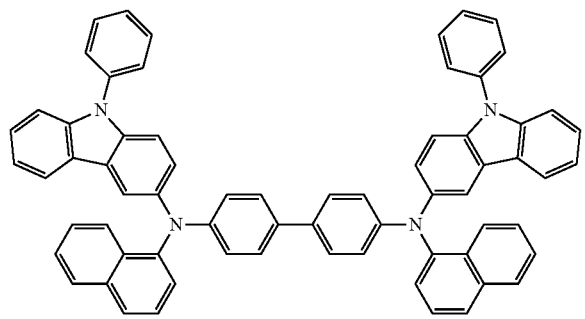
305
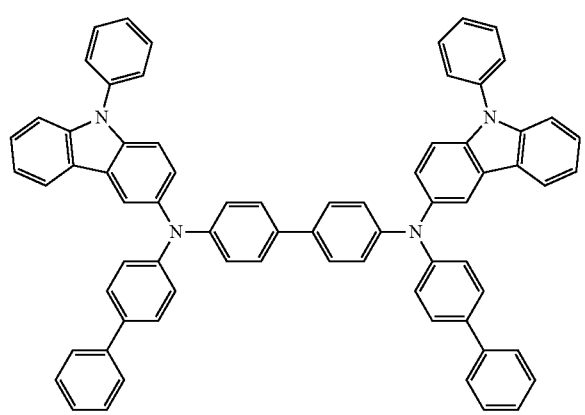
306
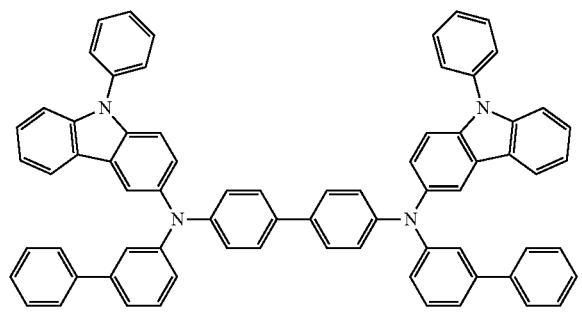
307
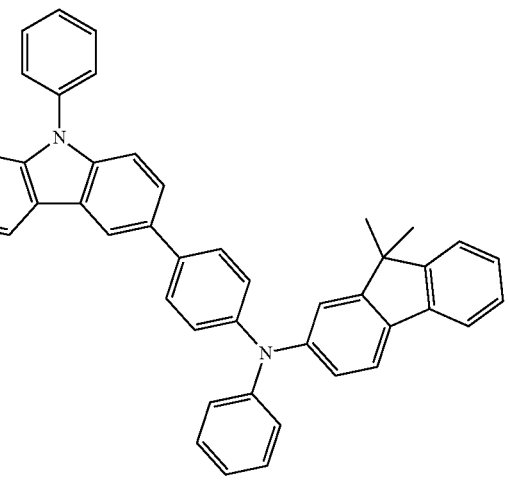
308
309

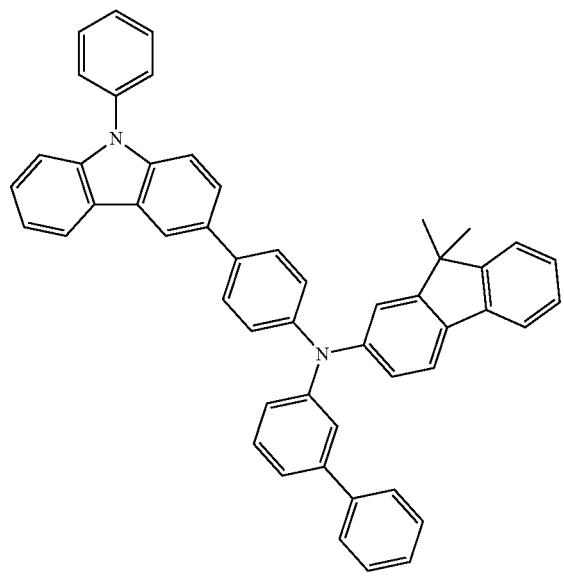
310
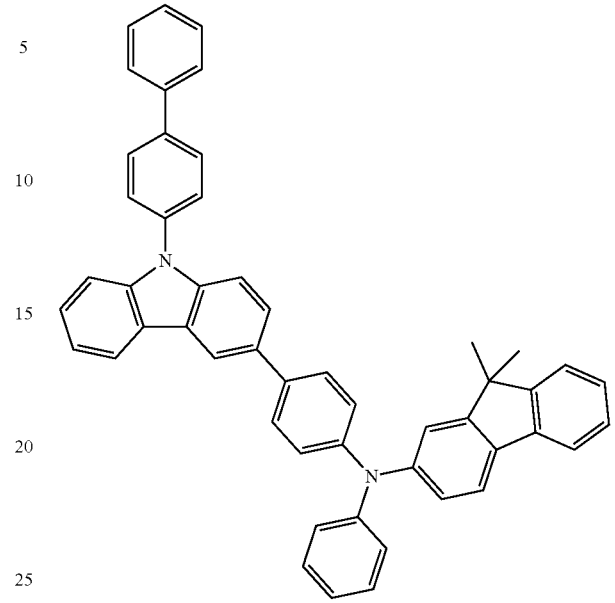
312
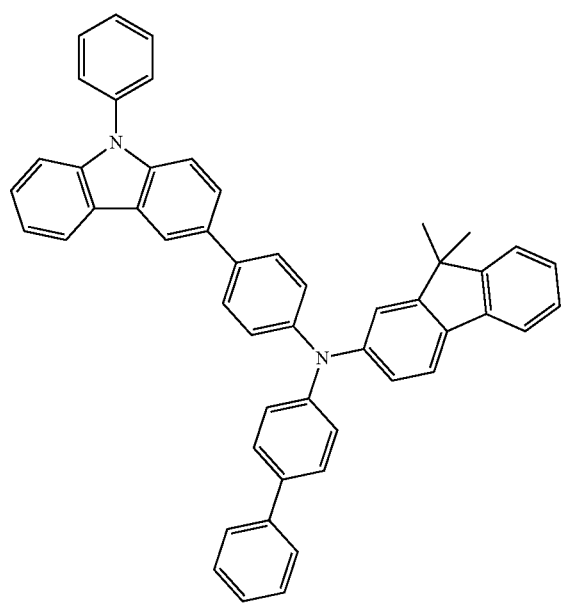
311
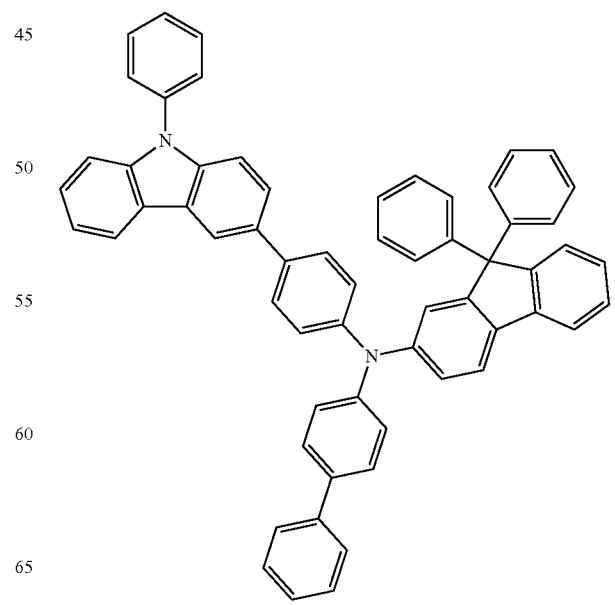
313

314
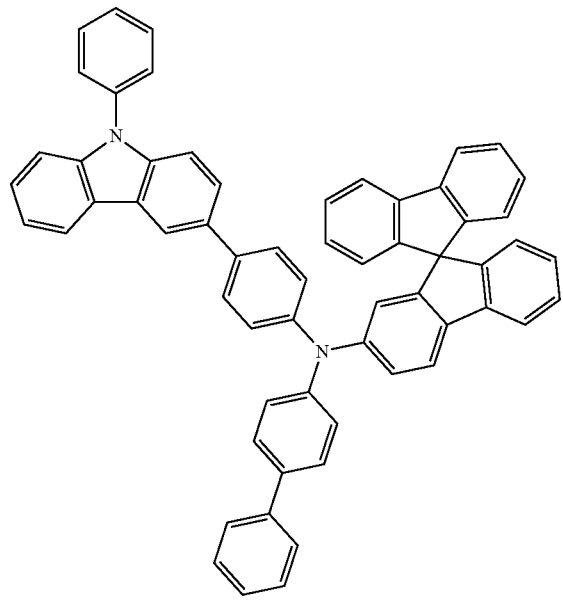
316
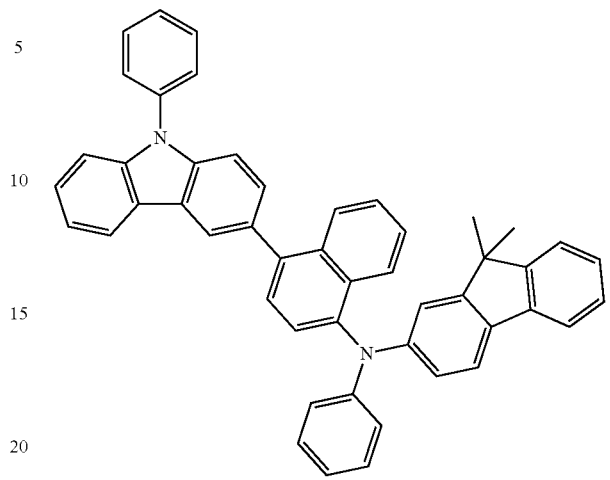
315
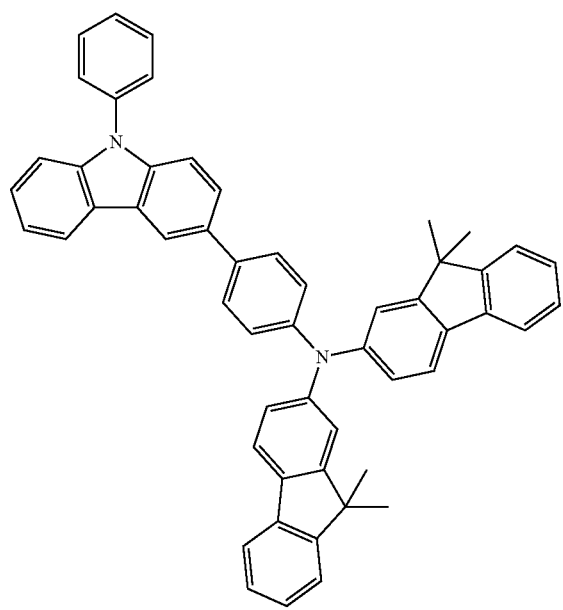
317
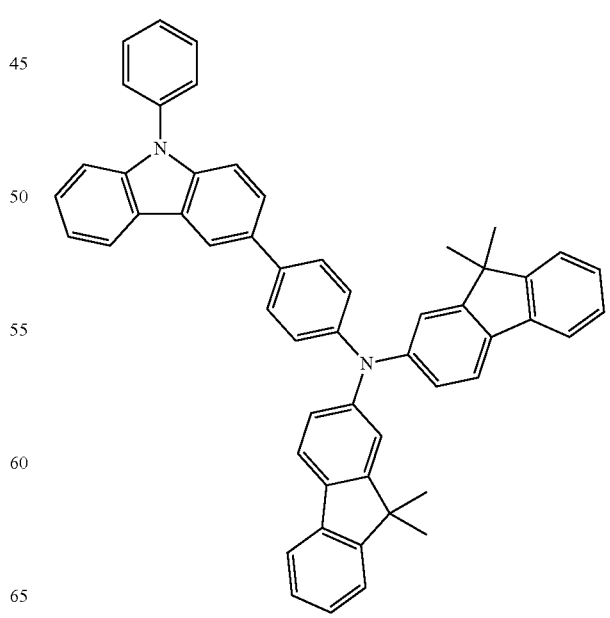

318

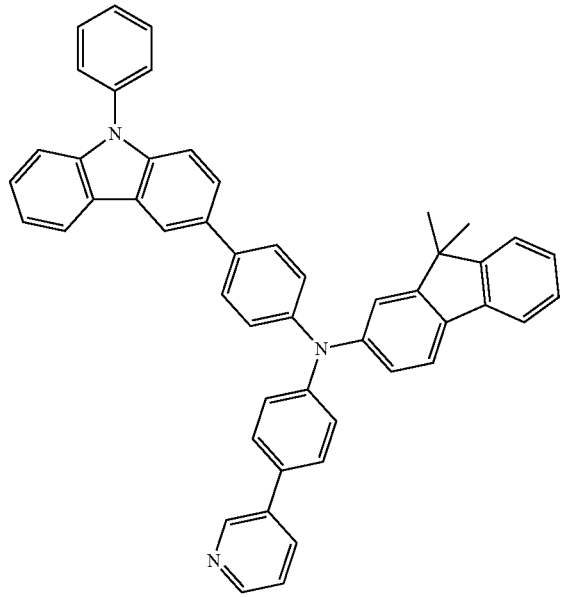

319

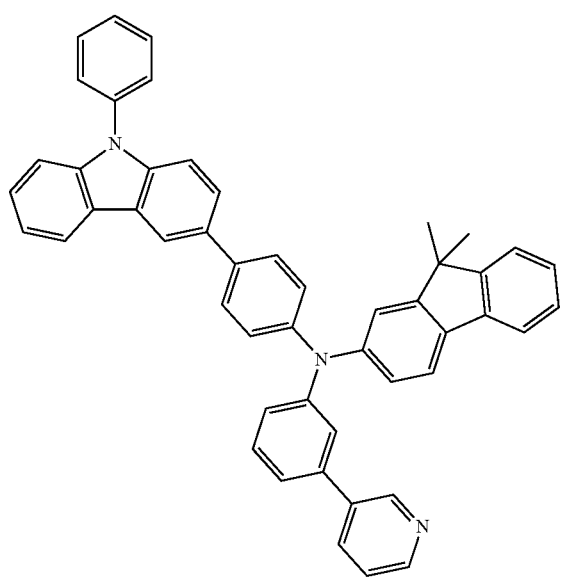

320

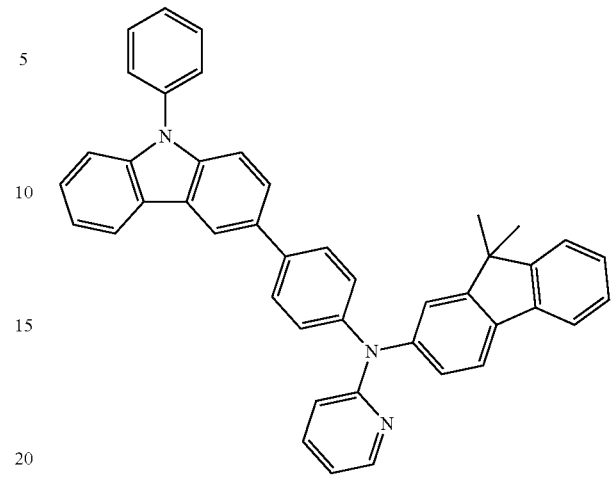

At least one of the HIL, HTL, and H-functional layer may further include a charge-generating material for improved layer conductivity, in addition to a suitable hole injecting material, hole transport material, and/or material having both hole injection and hole transport capabilities as described herein.

The charge-generating material may be, for example, a p-dopant. The p-dopant may be, for example, one or more of quinone derivatives, metal oxides, and compounds with a cyano group. Examples of the p-dopant include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200.

<Compound 200>

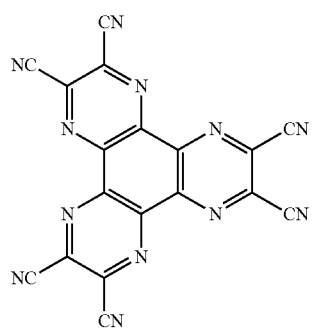

<F4-TCNQ>

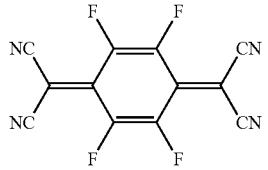

When the hole injection layer, hole transport layer, or H-functional layer further includes a charge-generating material, the charge-generating material may be homogeneously dispersed or non-homogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include any suitable hole injecting material or bale transporting material. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary depending on the material that is used to form the EML.

The EML may be formed using the compound of Formula 1, or any of a variety of suitable light-emitting materials, such as suitable hosts and dopants. Dopants that may be used to form the EML may include either a fluorescent dopant or a phosphorescent dopant that are suitable. Examples of the suitable host include Alq$_3$, 4,4'-N,N'-dicarbazole-biphenyl (CBP), poly(n-vinylcarbazole) (PVK), 9,10-di(naphthalene-2-yl)anthracene (DNA), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP, and Compounds 501 to 509.

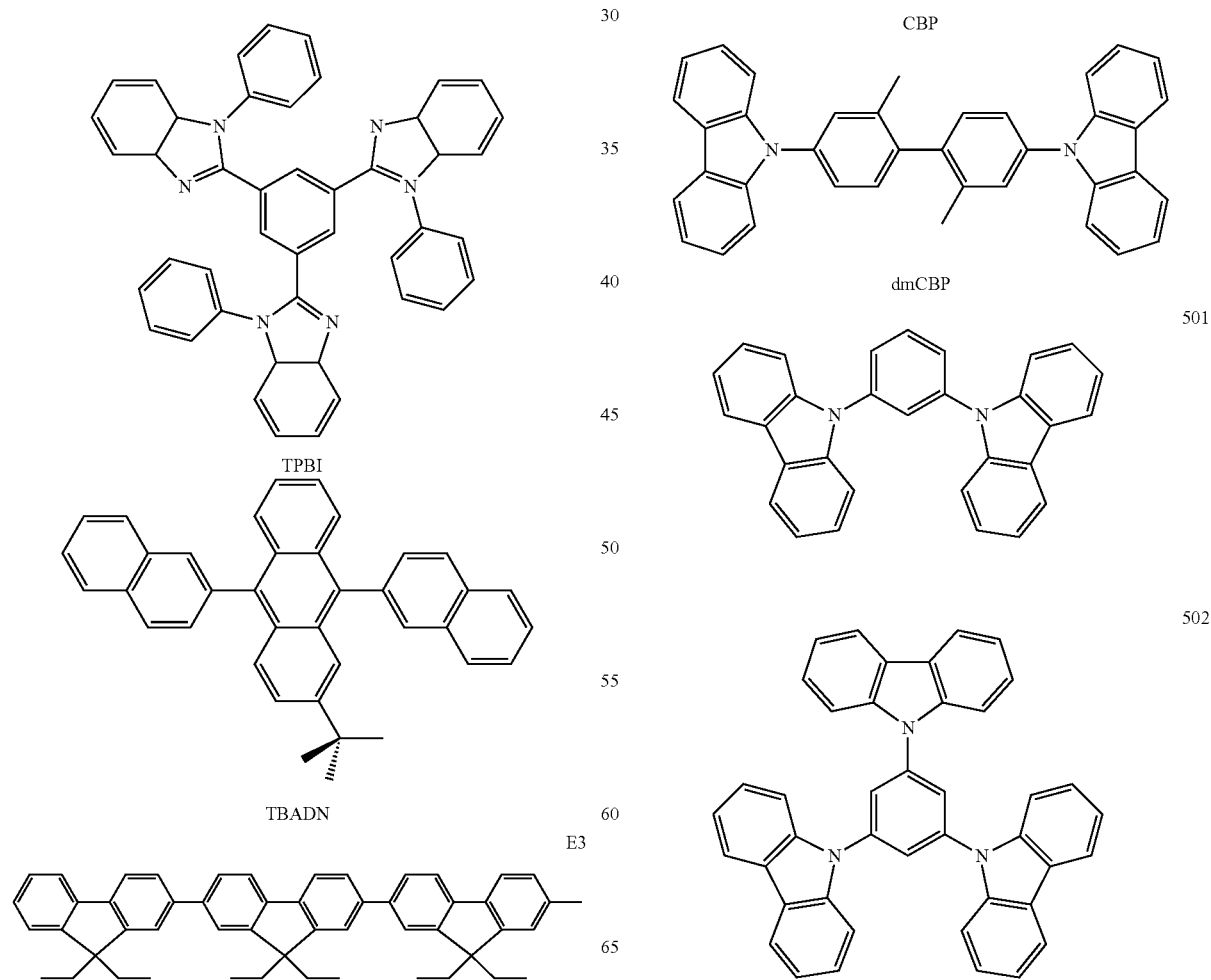

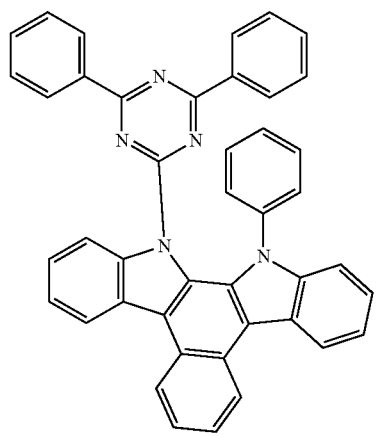
503
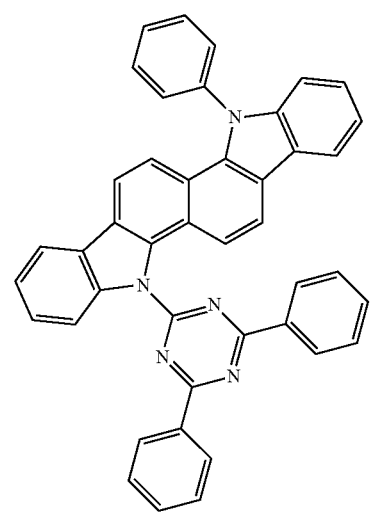
504
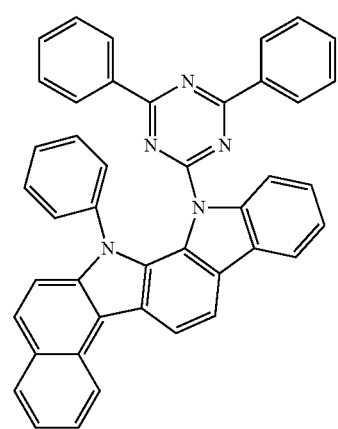
505
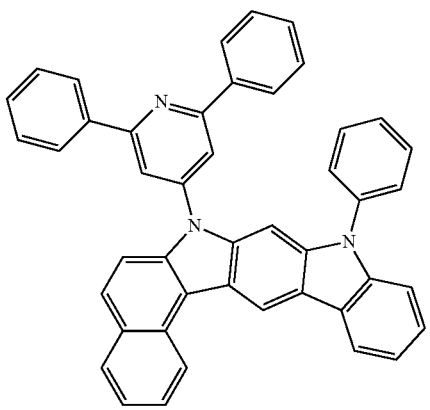
506
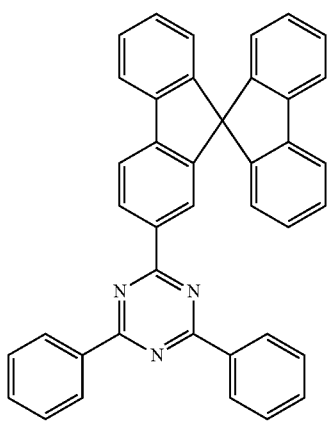
507
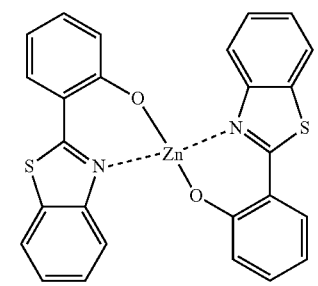
508
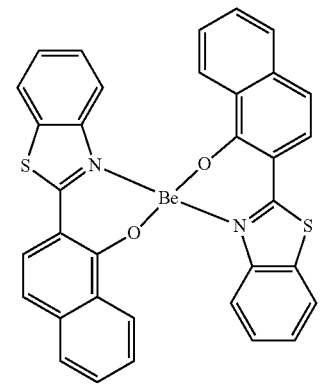
509
In some embodiments, an anthracene-based compound represented by Formula 400 may be used as the host.

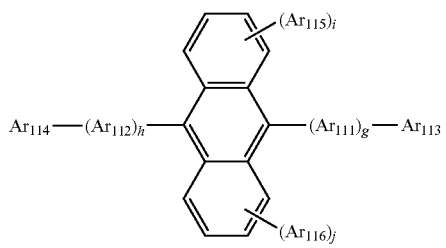

<Formula 400>

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_5$-$C_{60}$ aryl group; and g, h, I, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group. In Formula 400, g, h, I, and j may be each independently 0, 1, or 2. In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{10}$ alkoxy group, a phenyl group, a naphthyl group, an anthryl group, a pyrenyl group, a phenanthrenyl group, and a fluorenyl group, and

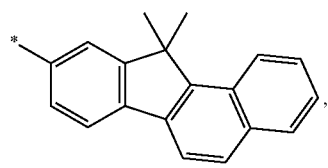 [SMILES: *c1ccc2c(c1)C(C)(C)c1c-2ccc2ccccc12]

or the like.

For example, the anthracene-based compound of Formula 400 may be one of the compounds represented by the following formulae:

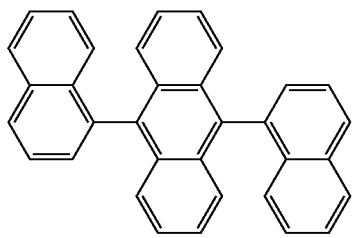

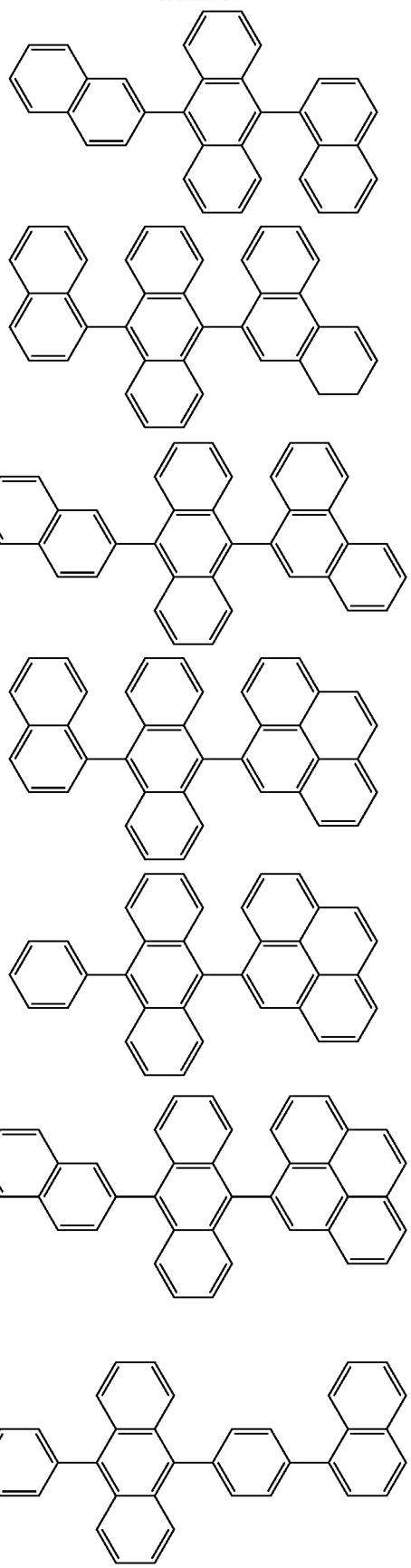

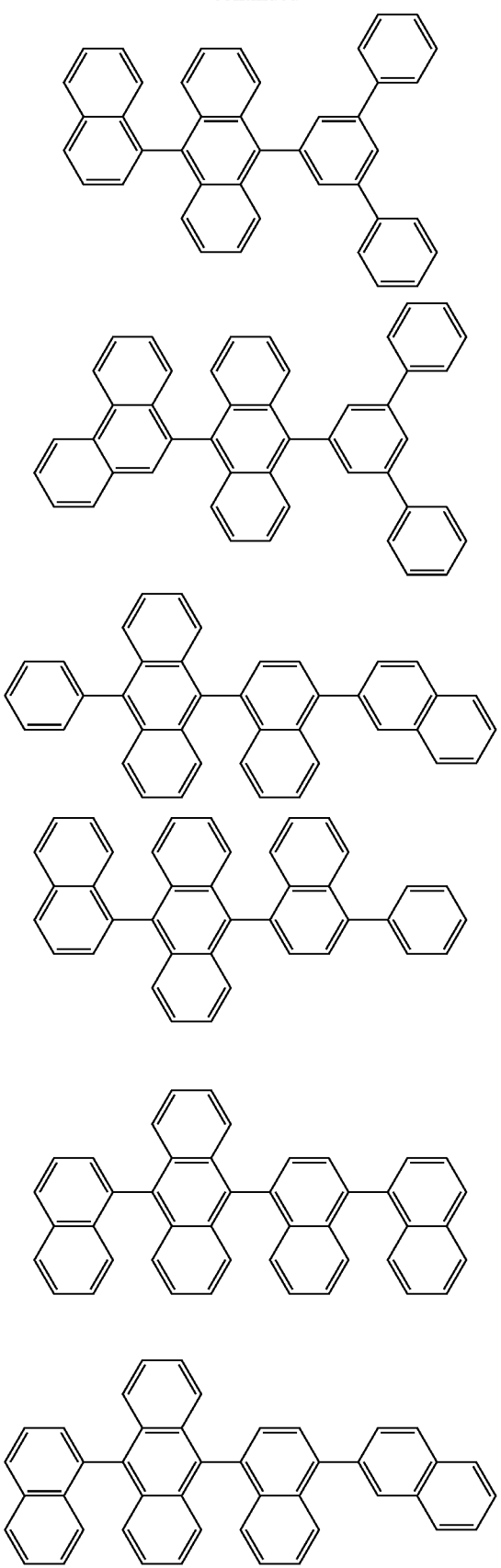
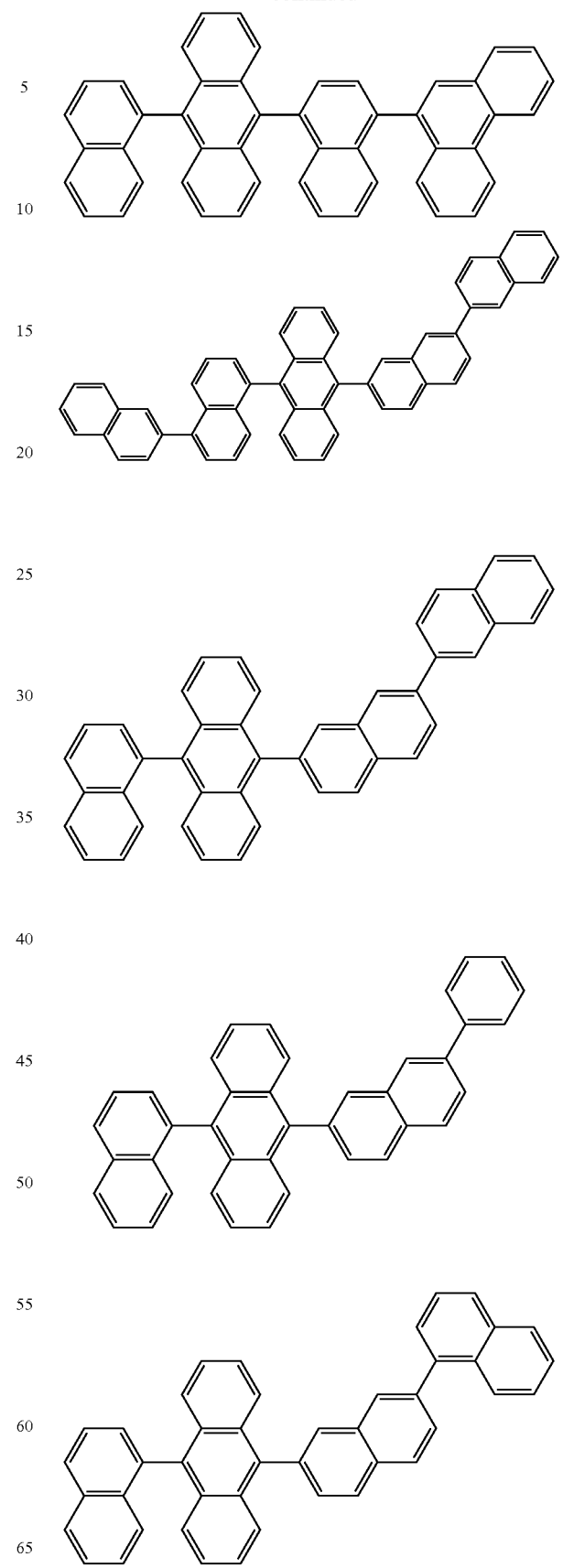

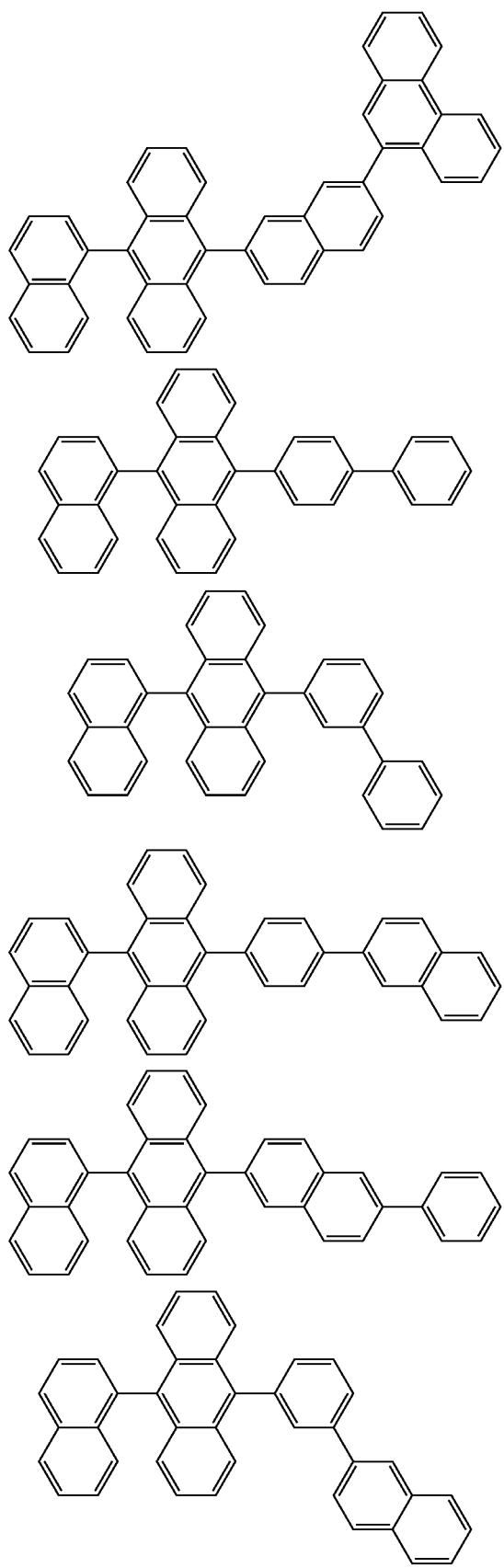
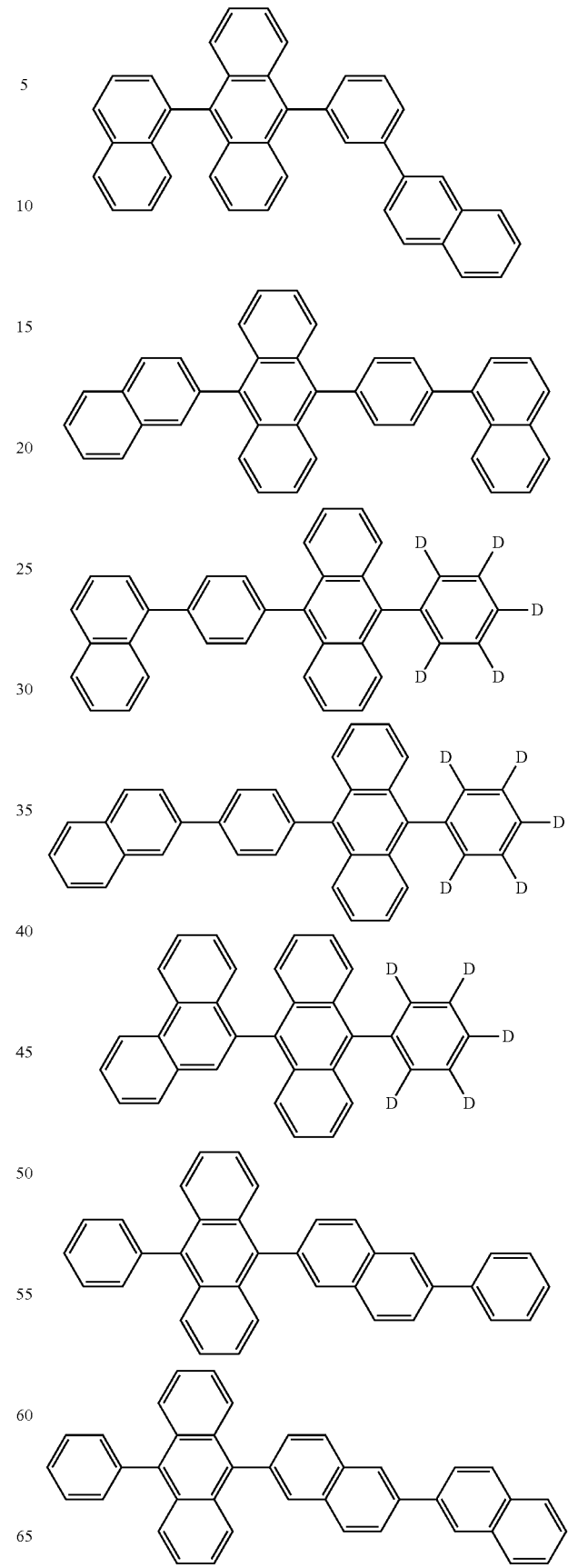

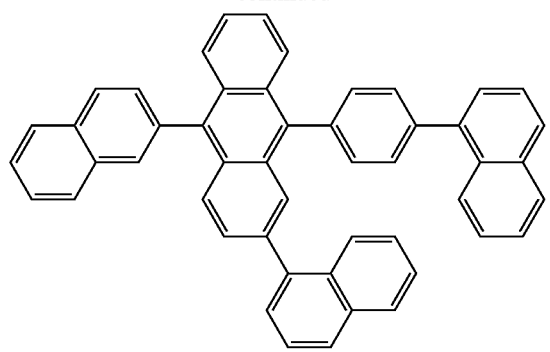
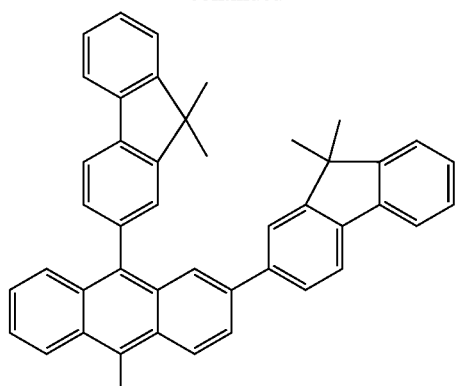
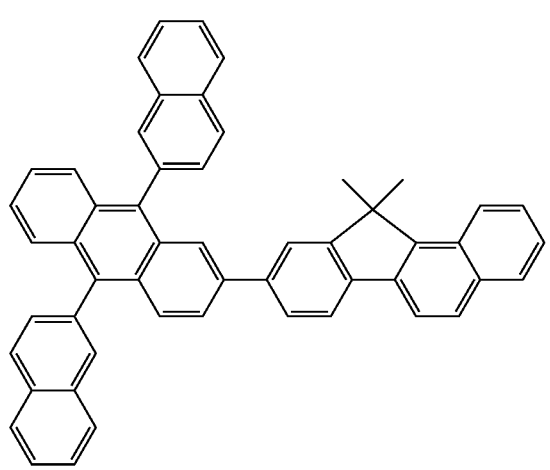
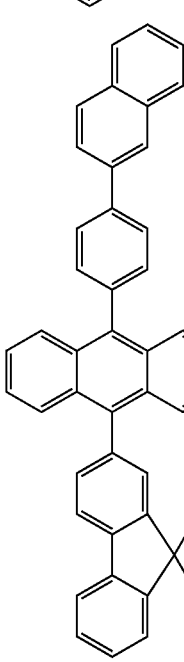
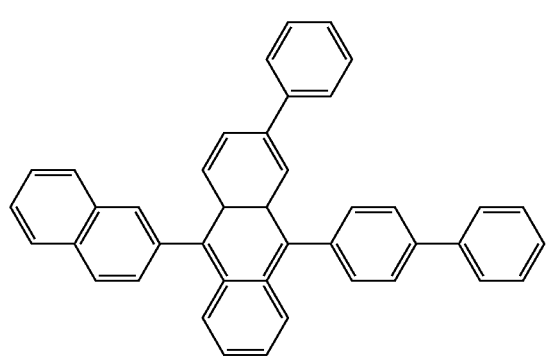
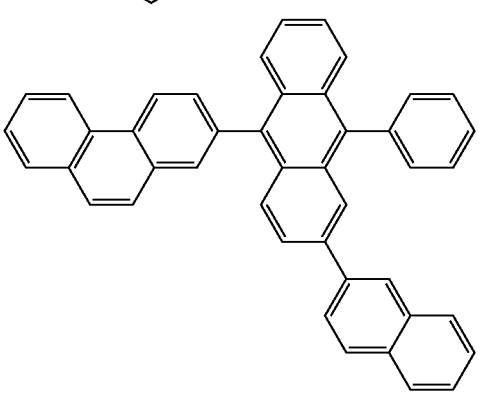
In some embodiments, an anthracene-based compound represented by Formula 401 may be used as the host.

<Formula 401>

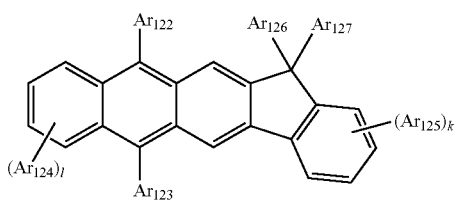

Ar$_{122}$ to Ar$_{125}$ in Formula 401 may be defined as described in conjunction with Ar$_{113}$ of Formula 400. Ar$_{126}$ and Ar$_{127}$ in Formula 401 may be each independently a $C_1$-$C_{10}$ alkyl group, for example, a methyl group, an ethyl group, or a propyl group. In Formula 401, k and l may be each independently an integer from 0 to 4, for example, 0, 1, or 2. For example, the anthracene compound of Formula 401 may be one of the compounds represented by the following formulae:

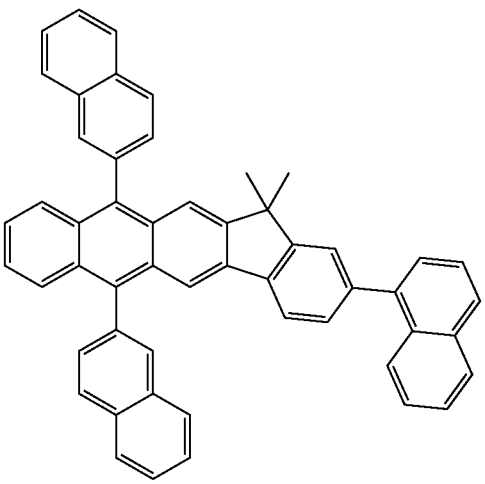

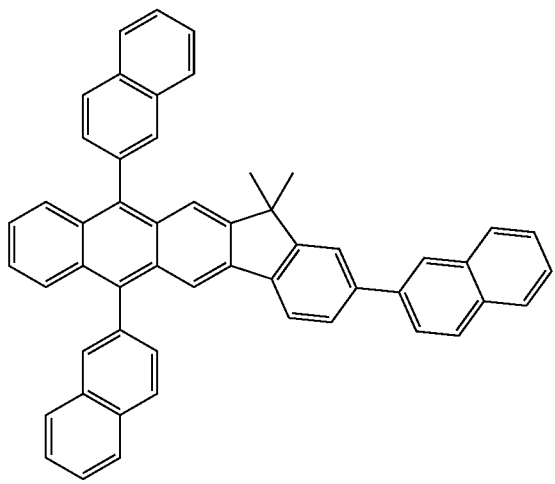

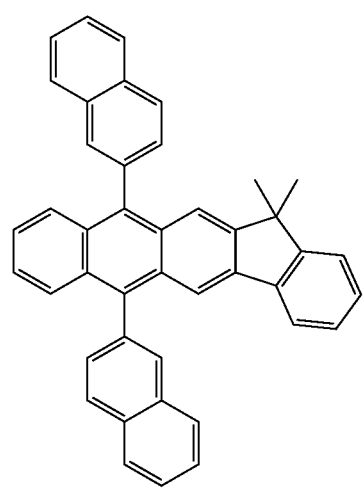

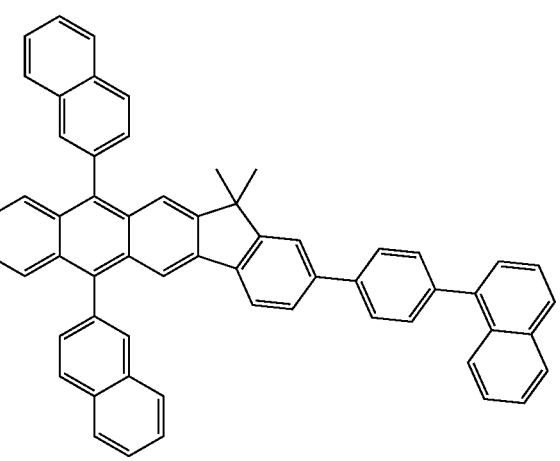

When the organic light-emitting device is a full color organic light-emitting device, the emission layer may be patterned into a red emission layer, a green emission layer, and a blue emission layer. At least one of the red EML, the green EML, and the blue EML may include a dopant described herein (ppy=phenylpyridine). Examples of the blue dopant include compounds represented by the following formulae.

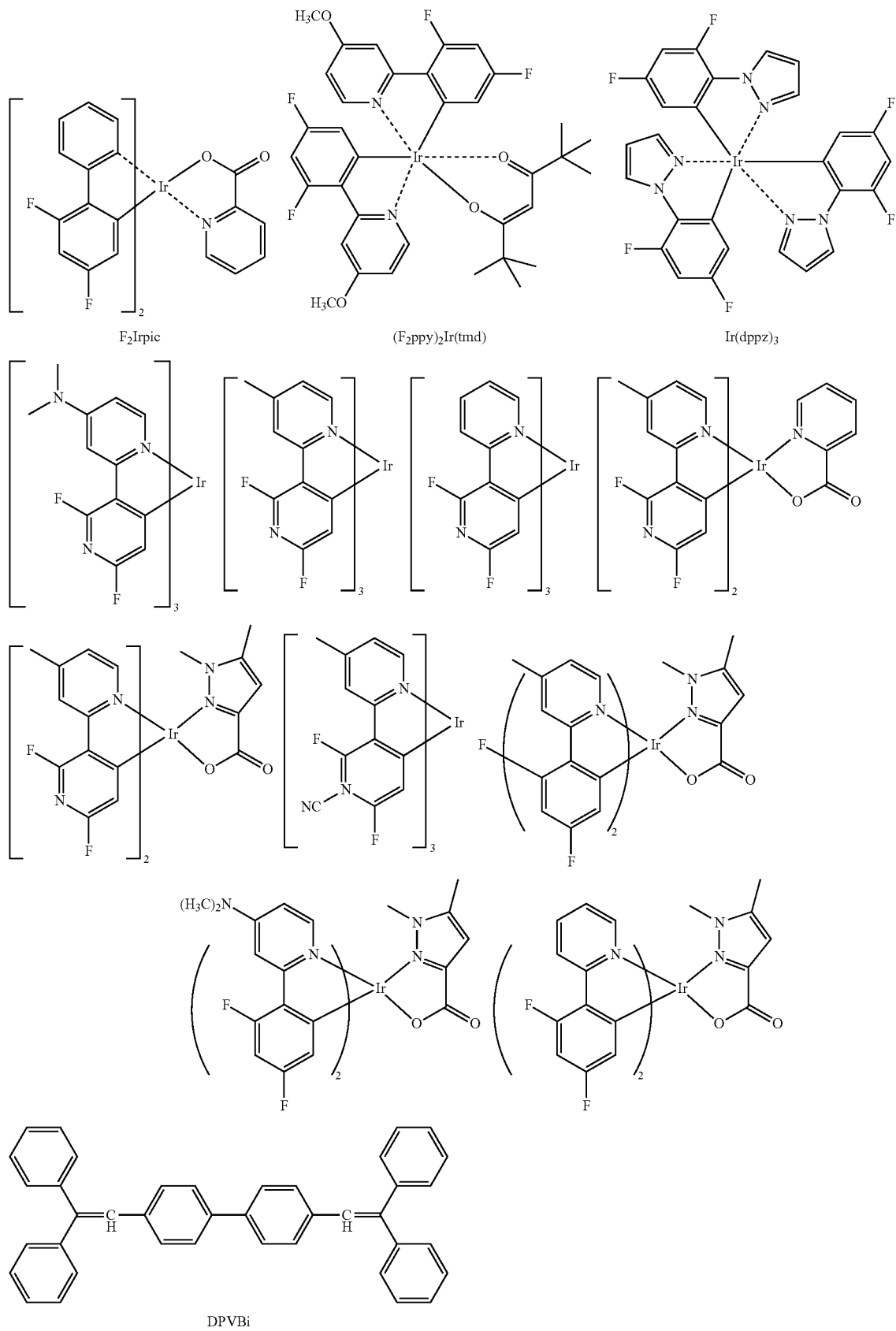

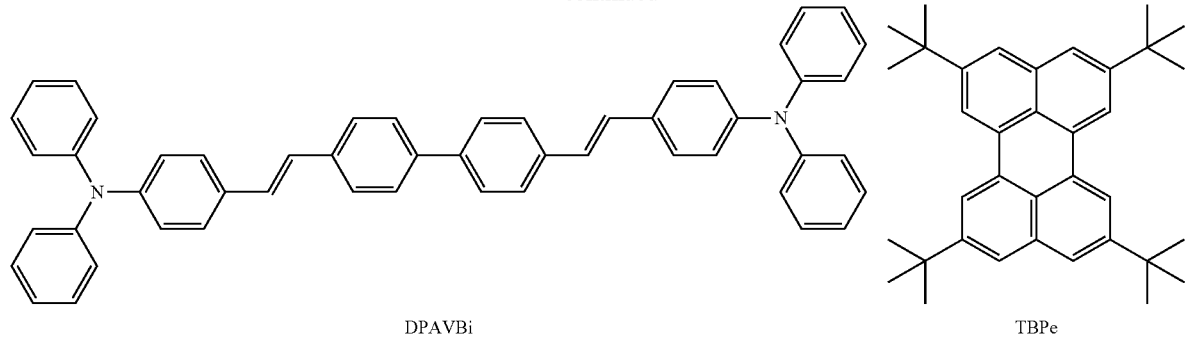
DPAVBi
TBPe
Examples of the red dopant include compounds represented by the following formulae.
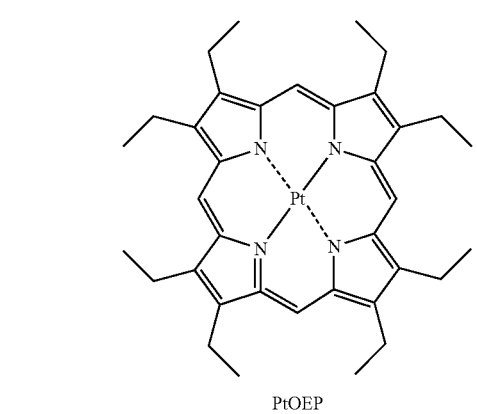
PtOEP
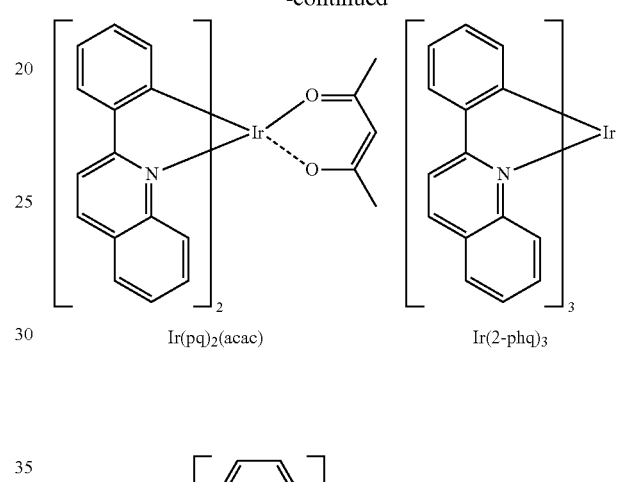
Ir(pq)₂(acac)
Ir(2-phq)₃
Ir(BT)₂(acac)
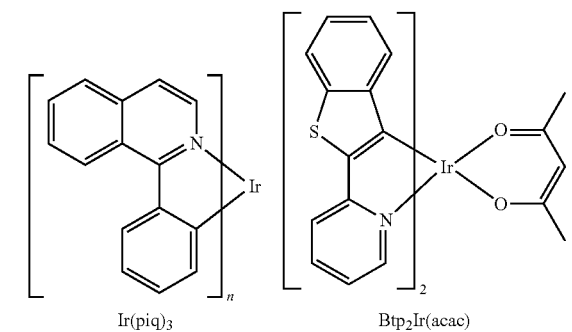
Ir(piq)₃
Btp₂Ir(acac)
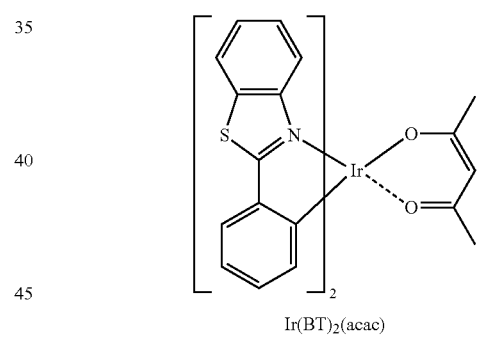
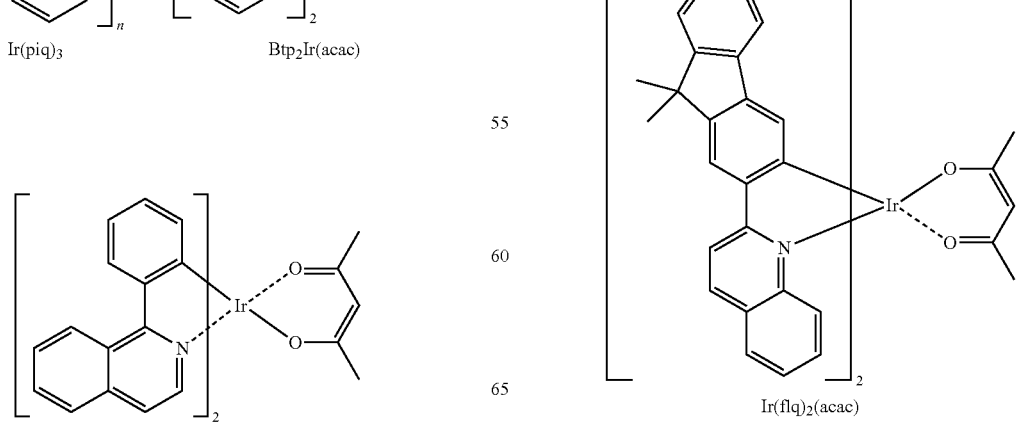
Ir(flq)₂(acac)

-continued
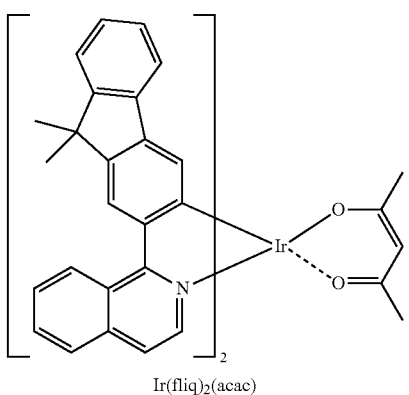
Ir(fliq)₂(acac)
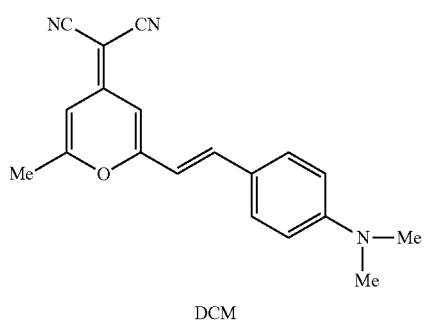
DCM
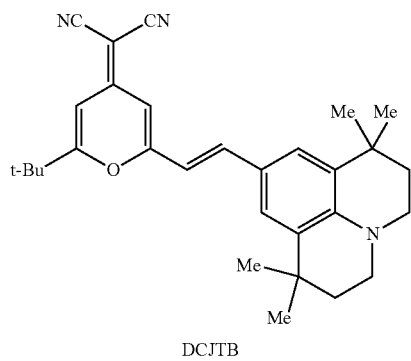
DCJTB
Examples of the green dopant include compounds represented by the following formulae.
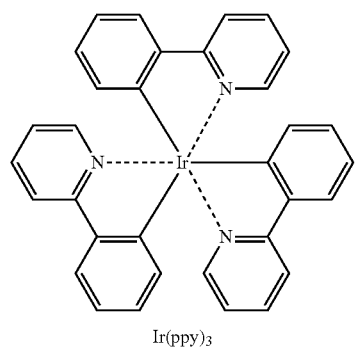
Ir(ppy)₃
-continued
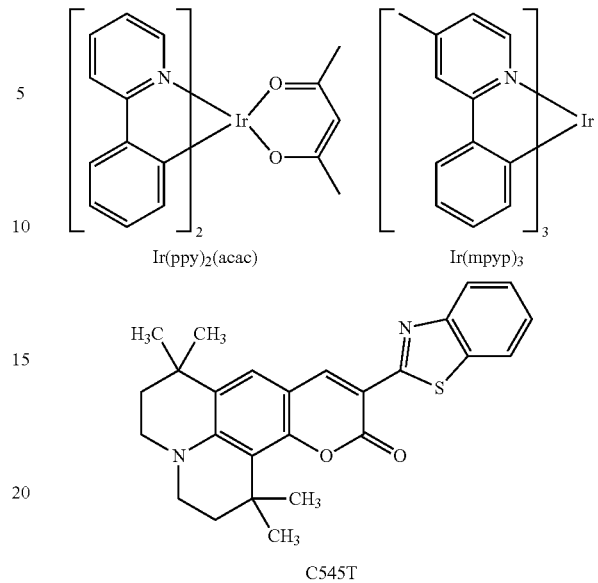
Ir(ppy)₂(acac)       Ir(mpyp)₃
C545T
Examples of the dopant that may be used in the EML include Pd complexes or Pt complexes represented by the following formulae.
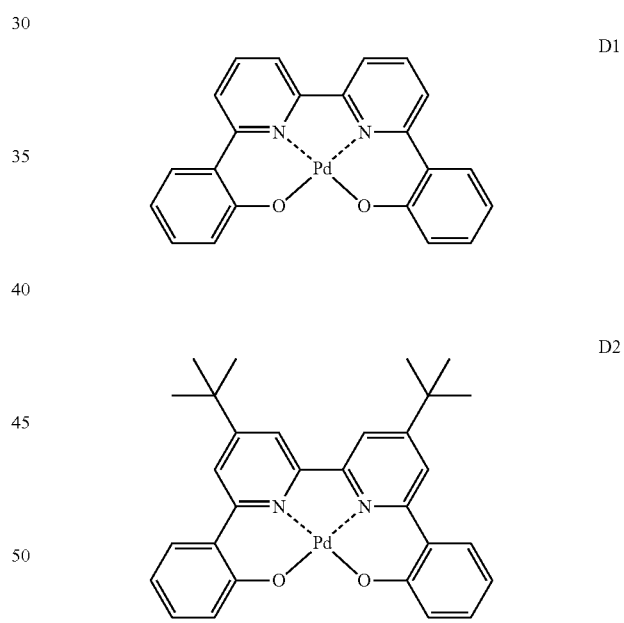
D1
D2
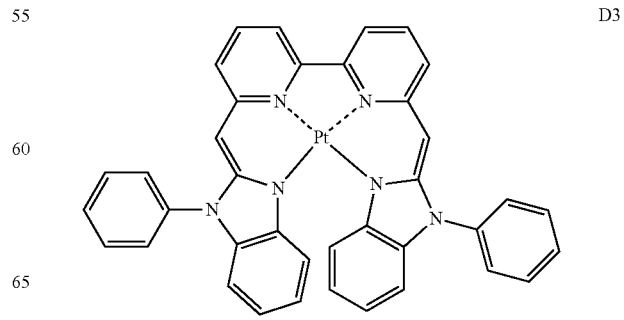
D3

D4 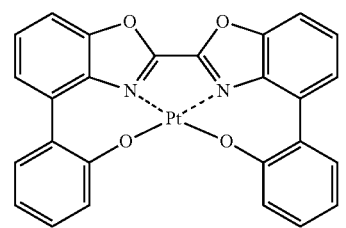
D5 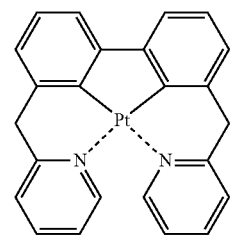
D6 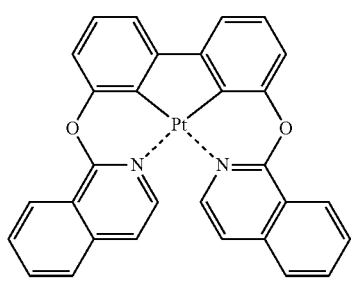
D7 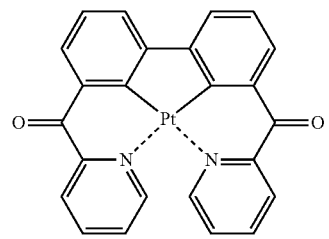
D8 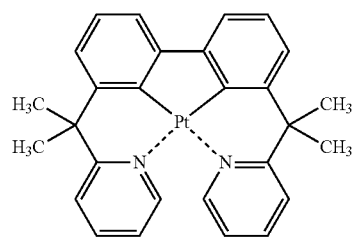
D9 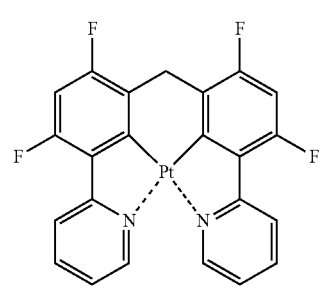
D10 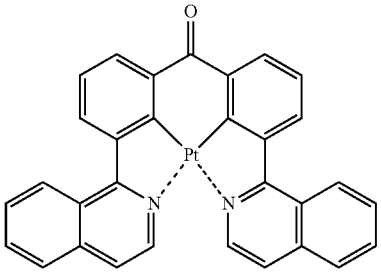
D11 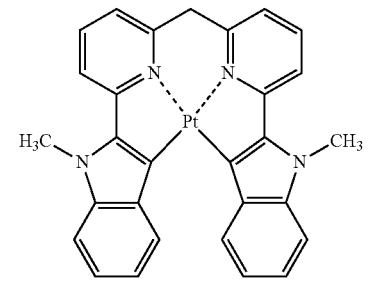
D12 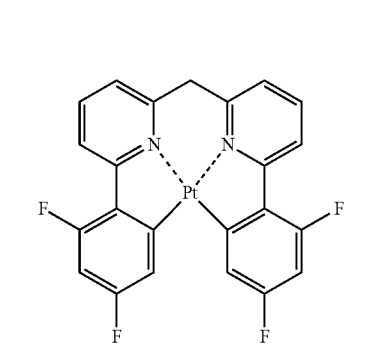
D13 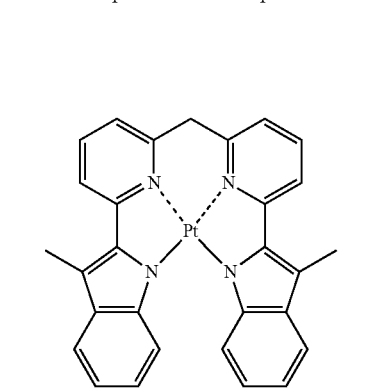
D14 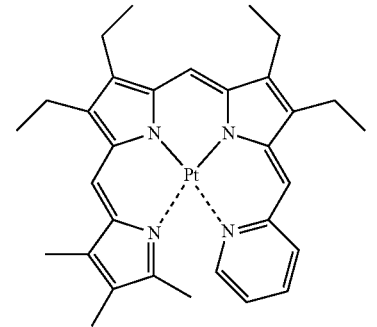

-continued
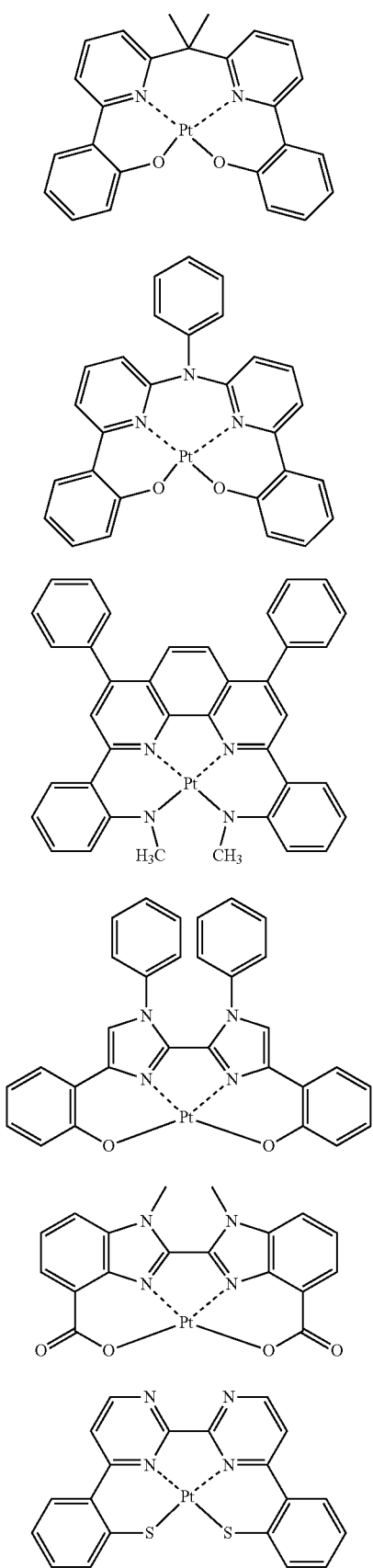
D15
D16
D17
D18
D19
D20
-continued
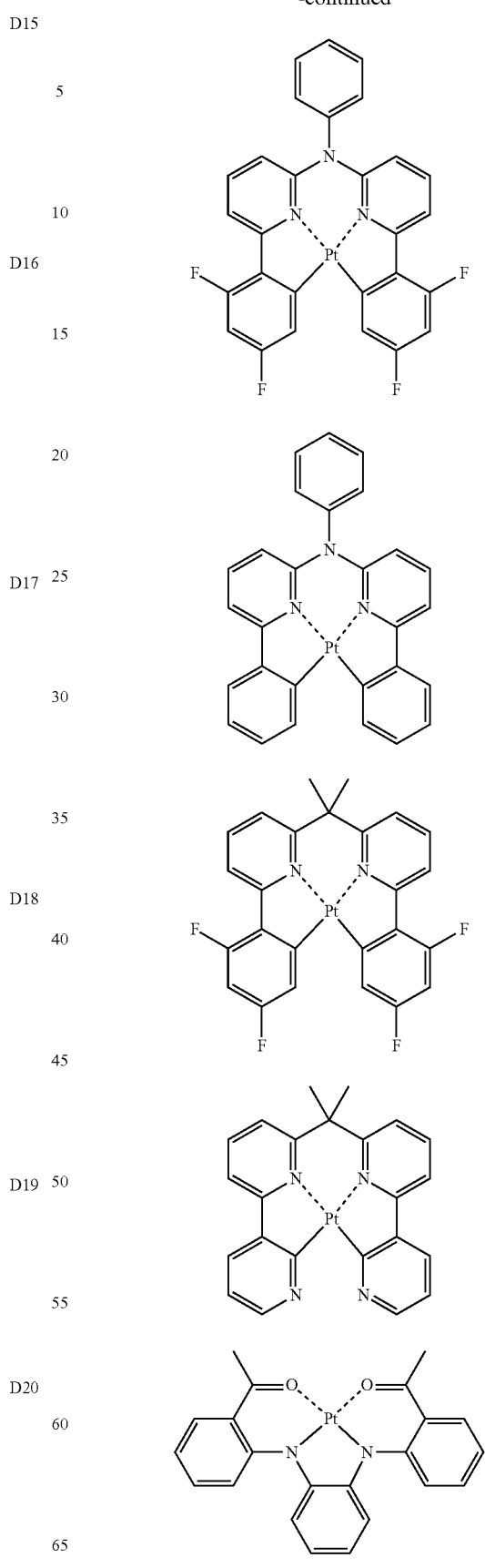
D21
D22
D23
D24
D25

-continued
D26
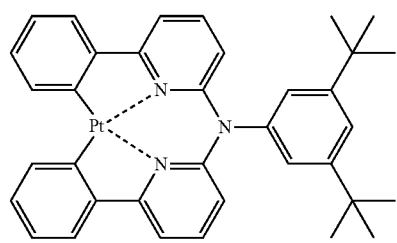
D27
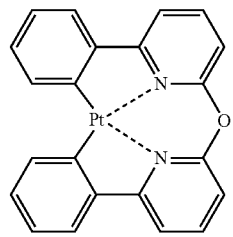
D28
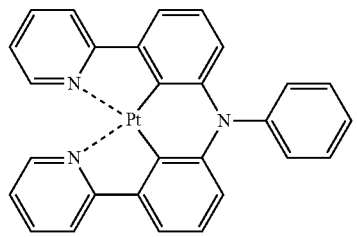
D29
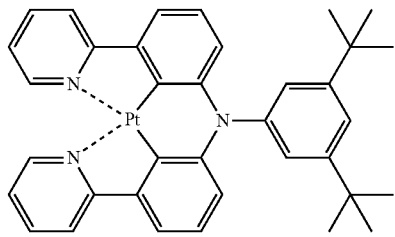
D30
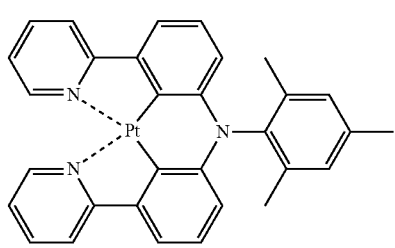
D31
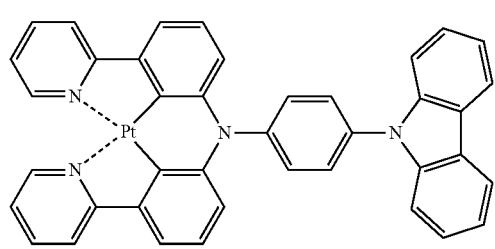
-continued
D32
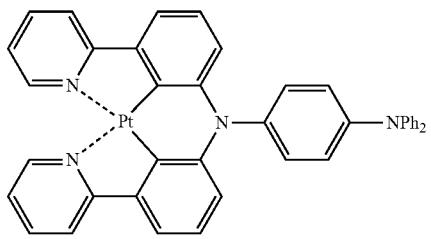
D33
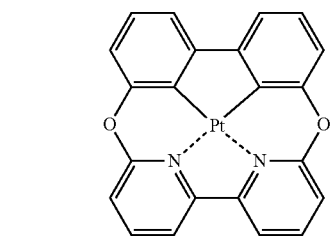
D34
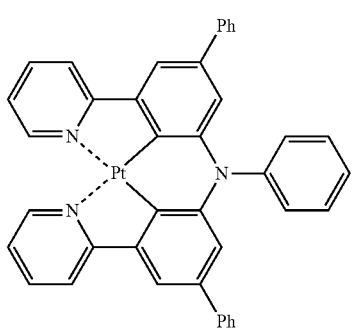
D35
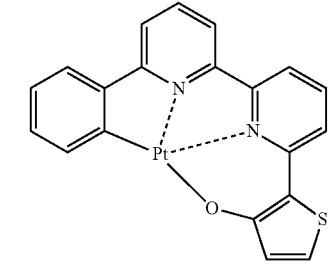
D36
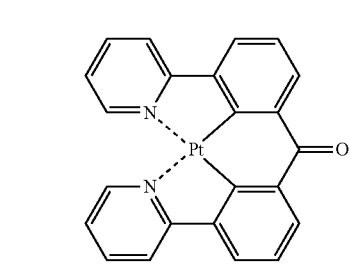

-continued
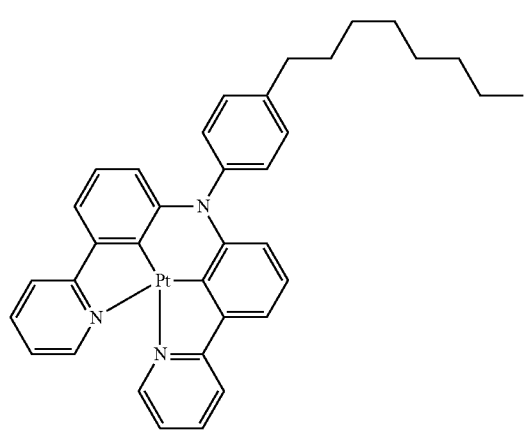
D37
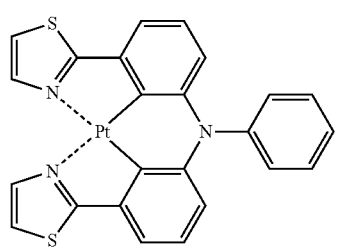
D38
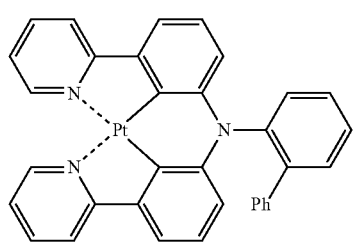
D39
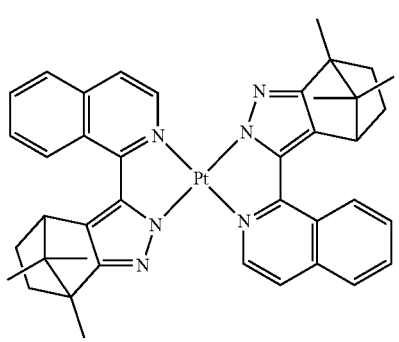
D40
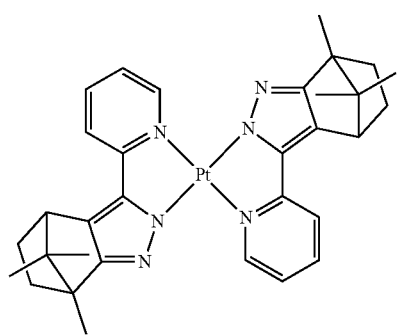
D41
-continued
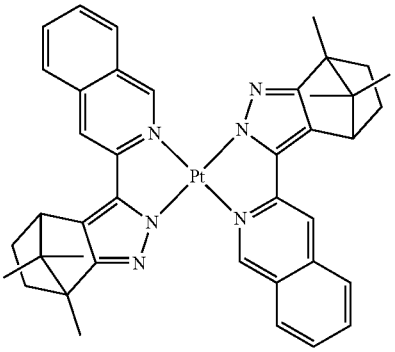
D42
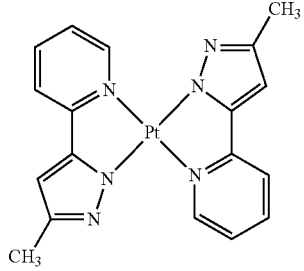
D43
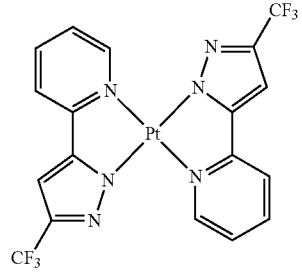
D44
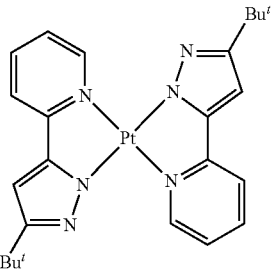
D45
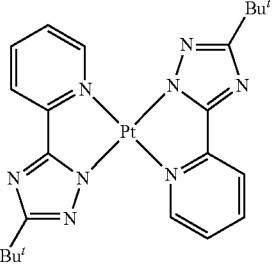
D46

-continued

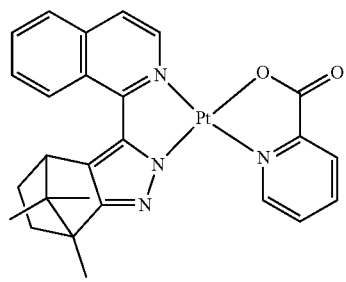
D47

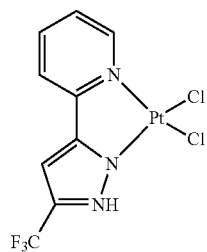
D48

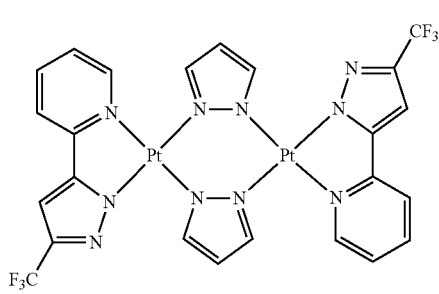
D49

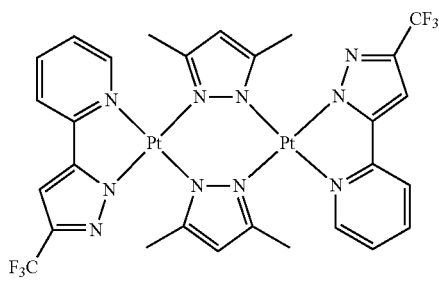
D50

-continued

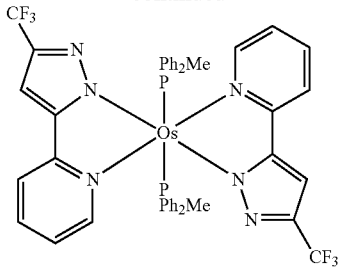
Os(fppz)₂(PPh₂Me)₂

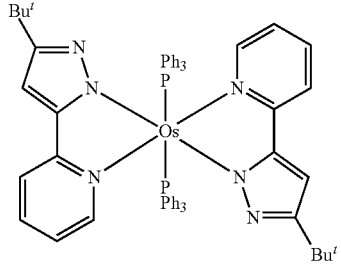
Os(fppz)₂(PPh₂Me)₂

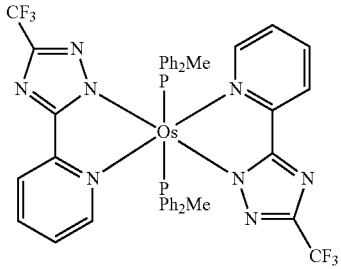
Os(fptz)₂(PPh₂Me)₂

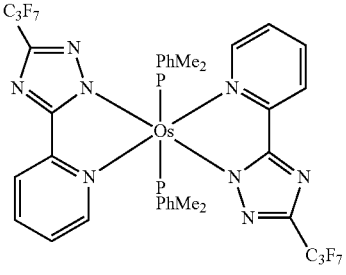
Os(hptz)₂(PPhMe₂)₂

Examples of the dopant that may be used in the EML include Os complexes represented by the following formulae.

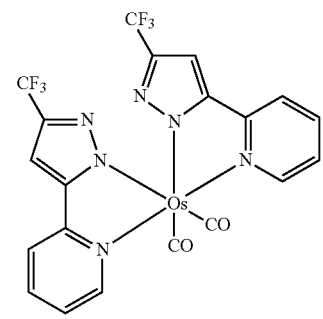
Os(fppz)₂(CO)₂

When the EML includes both a host and a dopant, the amount of the dopant may, for example, be from about 0.01 to about 15 parts by weight based on 100 parts by weight of the host. The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary depending on a compound that is used to form the ETL.

A material for forming the ETL may be the compound of Formula 1 or any suitable material that can stably transport electrons injected from an electron injecting electrode (cathode). Examples of materials for forming the ETL include a quinoline derivative, such as tris(8-quinolinorate)aluminum (Alq$_3$), TAZ, BAlq, beryllium bis(benzoquinolin-10-olate (Bebq$_2$), 9,10-di(naphthalene-2-yl)anthracene (ADN), Compound 201, and Compound 202.

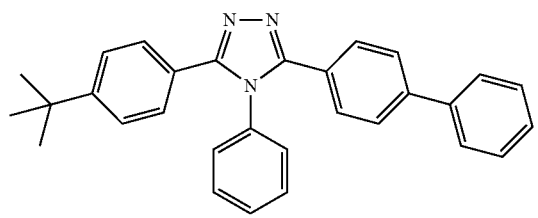

TAZ

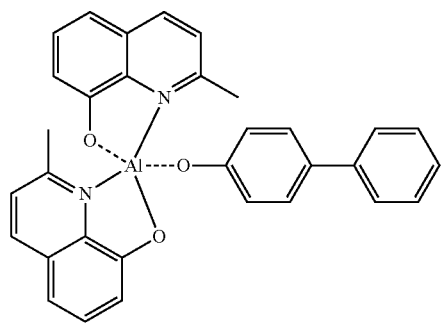

BAlq

<Compound 201>

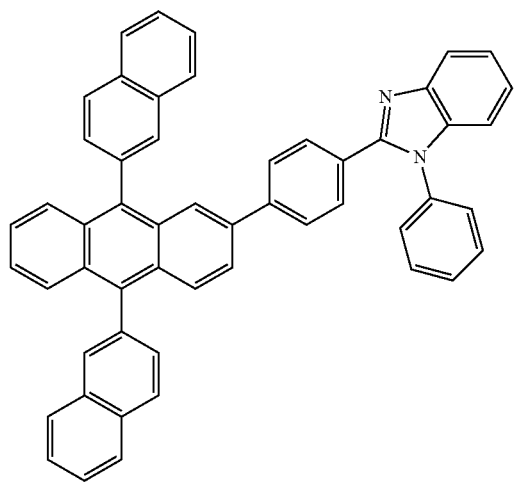

<Compound 202>

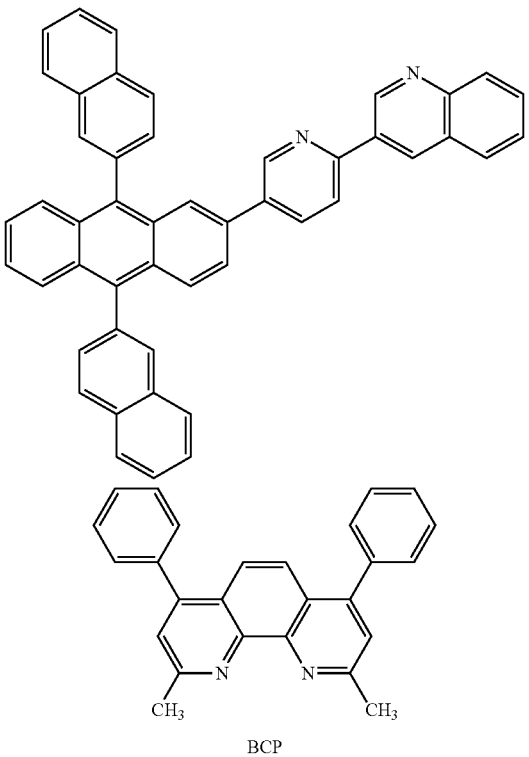

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any suitable electron-transporting organic compound. The metal-containing material may include a lithium (Li) complex. Examples of the Li complex include lithium quinolate (LiQ) and Compound 203:

<Compound 203>

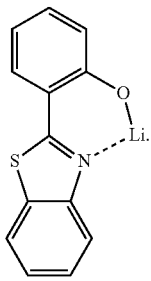

Then, an EIL, which facilitates injection of electrons from the cathode, may be formed on the ETL. Any suitable electron-injecting material may be used to form the EIL. Examples of materials for forming the EIL include LiF, NaCl, CsF, Li$_2$O, and BaO. The deposition and coating conditions for forming the EIL 18 may be similar to those for the formation of the HIL, though the deposition and coating conditions may vary depending on the material that is used to form the EIL 18. The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

Finally, the second electrode is disposed on the organic layer. The second electrode 17 may be a cathode that is an electron injection electrode. A material for forming the second electrode 17 may be a metal, an alloy, an electro-conductive compound, which have a low work function, or a mixture thereof. In this regard, the second electrode 9 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary depending on the material that is used to form the HBL. Any suitable hole-blocking material may be used. Examples of hole-blocking materials include oxadiazole derivatives, triazole derivatives, and phenanthroline derivatives. For example, bathocuproine (BCP) represented by the following formula may be used as a material for forming the HBL.

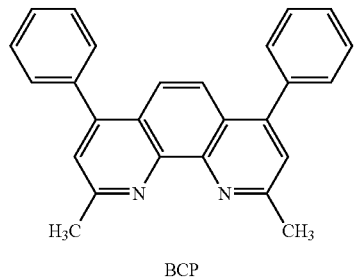 [SMILES: Cc1cc(-c2ccccc2)c2ccc3c(-c4ccccc4)cc(C)nc3c2n1 ; "BCP"]

BCP

The thickness of the HBL may be from about 20 Å to about 1000 Å, and in some embodiments, may be from about 30 Å to about 300 Å. When the thickness of the HBL is within these ranges, the HBL may have improved hole blocking ability without a substantial increase in driving voltage.

According to embodiments, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens. In some embodiments the organic layer of the organic light-emitting device may be formed of the compound of Formula 1 by using a deposition method or may be formed using a wet method of coating a solution of the compound of Formula 1.

The following examples are for illustrative purposes only and are not intended to limit the scope of the present disclosure. The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Example 1

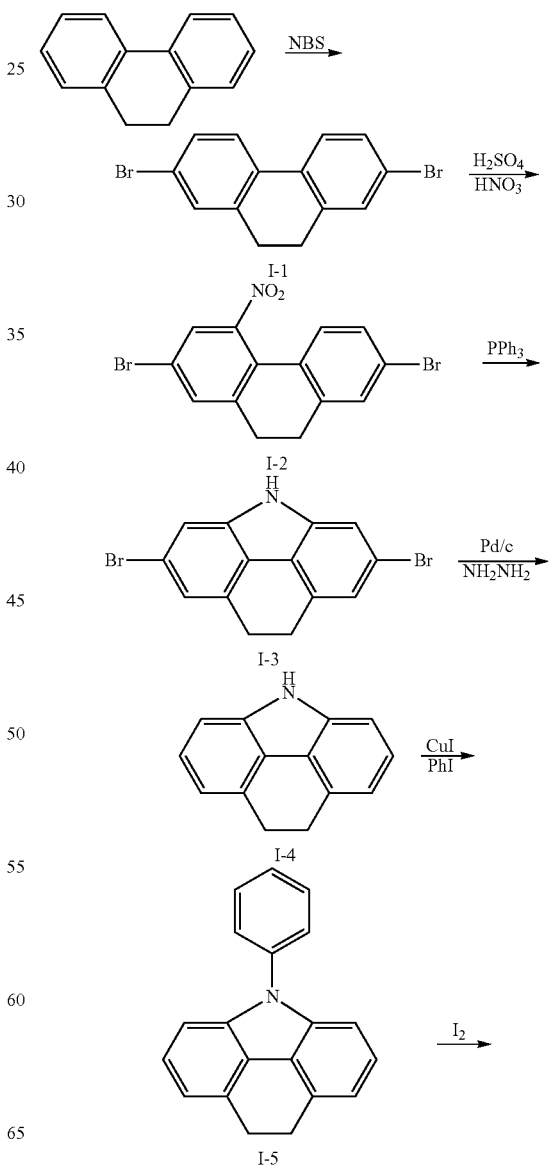

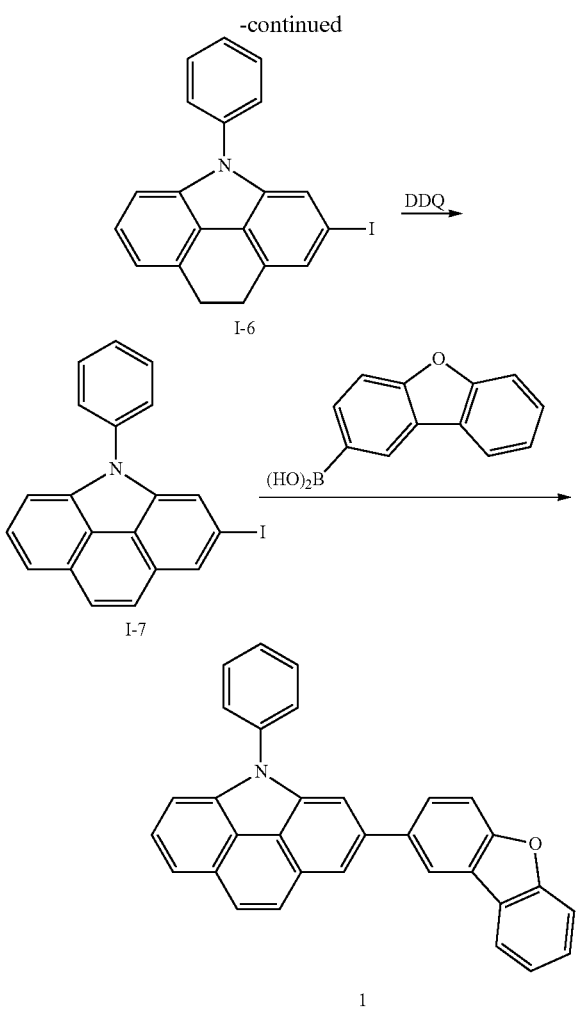

Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and then stirred at about 50° C. for about 12 hours. The reaction solution was cooled down to room temperature, and stirred for about 30 minutes to precipitate crystals. The crystals were collected through a vacuum filter, and washed with methanol to obtain 8.4 g of Intermediate I-1 as gray crystals (Yield 45%). This compound was identified using liquid chromatography-mass spectroscopy (LC-MS). $C_{14}H_{10}Br_2M^+$ 336.9

Synthesis of Intermediate I-2

After 5.0 g (15.0 mmol) of Intermediate I-1 was completely dissolved in 50 mL of dichloromethane, 1.7 g (30.0 mmol) of nitric acid was added, and 1.5 g (15.0 mmol) of sulfuric acid was slowly dropwise added thereto to obtain a solution, which was then stirred at about 30° C. for about 6 hours. After completion of the reaction, the reaction solution was cooled down to room temperature, 50 mL of methanol was added thereto and stirred for about 2 hours to precipitate crystals. The crystals were collected through a vacuum filter, and washed with methanol to obtain 5.2 g of Intermediate I-2 as yellow crystals (Yield 90%). This compound was identified using LC-MS. $C_{14}H_9Br_2NO_2$ $M^+$ 381.9

Synthesis of Intermediate I-3

After 4.6 g (12.0 mmol) of Intermediate I-2 was dissolved in 30 mL of o-dichlorobenzene and heated until completely dissolved, 4.7 g (18.0 mmol) of triphenylphosphine was added thereto and stirred at about 180° C. for about 3 hours. After the reaction solution was cooled down to room temperature, the solvent was removed by evaporation to obtain a residue, which was then separated and purified using silica gel column chromatography, and washed with methanol to obtain 2.9 g of Intermediate I-3 (Yield: 70%) as white crystals. This compound was identified using LC-MS. $C_{14}H_9Br_2N$ $M^+$ 349.9

Synthesis of Intermediate I-4

After 10 g (28.5 mmol) of Intermediate I-3 and 0.03 g (0.28 mmol) of Pd/C (10%) were dissolved in 100 mL of ethanol at room temperature, the temperature was increased to 50° C., and 5.48 g (171 mmol) of hydrazine was dropwise added thereto and stirred for about 24 hours. The reaction solution was cooled down to room temperature, and washed with acetone, followed by adding 100 mL of ice water to obtain 3.63 g of Intermediate I-4 as white crystals (Yield 66%). This compound was identified using LC-MS. $C_{14}H_{11}N$ M+ 194.1

Synthesis of Intermediate I-5

1.93 g (10.0 mmol) of Intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) of $K_2CO_3$ were dissolved in 30 mL of N,N-dimethylformamide (DMF) to obtain a solution, which was then stirred at about 80° C. for about 24 hours. The reaction solution was cooled down to room temperature, and then extracted three times with 30 mL of water and 40 mL of diethyl ether. An organic layer was collected and was dried using magnesium sulfate to evaporate the solvent. The residue was separated and purified using silica gel column chromatography to obtain 2.39 g of Intermediate I-5 (Yield 89%). This compound was identified using LC-MS. $C_{20}H_{15}N$ $M^+$ 270.1

Synthesis of Intermediate I-6

After 10 g (37.1 mmol) of Intermediate I-5 was completely dissolved in 100 mL of dichloromethane, 3.58 g (14.1 mmol) of iodine and 2.38 g (11.13 mmol) of $KIO_3$ were added over five times. After being stirred for about 6 hours, the reaction solution was washed with methanol to obtain 8.06 g of Intermediate I-6 (Yield 55%). This compound was identified using LC-MS. $C_{20}H_{14}IN$ M+ 396.1

Synthesis of Intermediate I-7

After 10 g (25.3 mmol) of Intermediate I-6 was dissolved in 100 mL of toluene in an oxygen atmosphere, 1.57 g (7.6 mmol) of 2,3-dichloro-5,6-dicyano-1,4-benzoquinone and 0.52 g (7.6 mmol) of $NaNO_2$ were added thereto. After being stirred at about 110° C. for about 6 hours and completion of the reaction, the reaction solution was cooled down to room temperature, and the solvent was evaporated. The residue was separated and purified using silica gel column chromatography to obtain 8.94 g of Intermediate I-7 (Yield: 90%). This compound was identified using LC-MS. $C_{20}H_{12}IN$ M+ 394.0

Synthesis of Compound 1

3.93 g (10 mmol) of Intermediate I-7, 2.12 g (10.0 mmol) of dibenzo[b,d]furan-2-ylboroni acid, 0.58 g (0.5 mmol) of tetrakis(triphenylphosphine)palladium $(Pd(PPh_3)_4)$, and 4.15 g (30.0 mmol) of $K_2CO_3$ were dissolved in 40 mL of a mixed solution of tetrahydrofuran (THF) and $H_2O$ (2:1 by volume), and then stirred at about 70° C. for about 5 hours. The reaction solution was cooled down to room temperature, followed by adding 40 mL of water and extracting three times with 50 mL of diethylether. An organic layer was collected and was dried using magnesium sulfate to evaporate the solvent. The residue was separated and purified using silica gel column chromatography to obtain 3.77 g of Compound 1 (Yield 87%).

This compound was identified using mass spectroscopy/fast atom bombardment (MS/FAB) and $^1$H nuclear magnetic resonance (NMR). $C_{32}H_{19}NO$ cal. 433.15. found 434.15 $^1$H NMR (CDCl$_3$, 400 MHz) . . . 8.26 (m, 1H), 8.06 (m, 1H), 8.04-8.02 (dd, 1H), 7.92-7.90 (m, 1H), 7.78-7.75 (m, 1H), 7.72-7.69 (m, 2H), 7.58-7.53 (m, 4H), 7.49 (s, 1H), 7.48-7.45 (m, 2H), 7.39-7.35 (m, 2H), 7.31-7.30 (m, 2H), 7.23 (d, 1H)

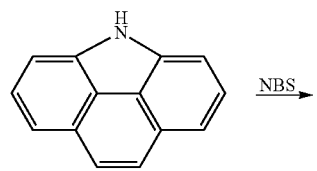

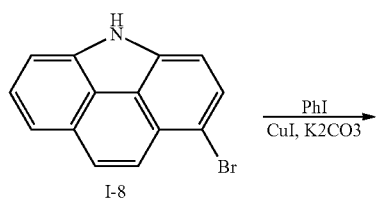

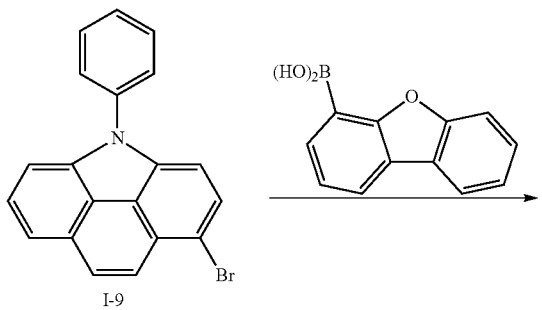

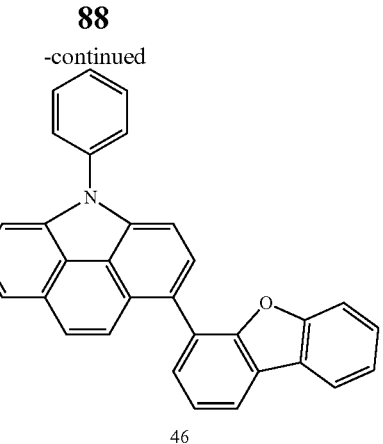

46

Synthesis of Intermediate I-8

After 1.91 g (10.0 mmol) of 6H-benzo[def]carbazole was completely dissolved in 60 mL of carbon tetrachloride (CCl$_4$), 1.78 g (10.0 mmol) of N-bromosuccinimide was added thereto to obtain a solution, which was then stirred at about 80° C. for about 6 hours. The reaction solution was cooled down to room temperature, and stirred for about 30 minutes to precipitate crystals. The crystals were collected through a vacuum filter, and washed with methanol to obtain 1.1 g of Intermediate I-8 as white crystals (Yield 45%). This compound was identified using LC-MS. $C_{14}H_8BrN$: M$^+$ 245.9

Synthesis of Intermediate I-9

Intermediate I-9 was synthesized in the same manner as in the synthesis of Intermediate I-5, except that Intermediate I-8 instead of Intermediate I-4 was used. This compound was identified using LC-MS. $C_{20}H_{12}BrN$: M$^+$ 346.0

Synthesis of Compound 46

3.55 g (Yield 82%) of Compound 46 was synthesized in the same manner as in the synthesis of Compound 1, except that Intermediate I-9 and dibenzo[b,d]furan-4-ylboronic acid, instead of Intermediate I-7 and dibenzo[b,d]furan-2-ylboronic acid, respectively, were used.

This compound was identified using MS/FAB and $^1$H NMR. $C_{32}H_{19}NO$ cal. 433.15. found 434.15 $^1$H NMR (CDCl$_3$, 400 MHz) 8.19-8.17 (ss, 1H), 8.01-7.97 (m, 2H), 7.95-7.93 (m, 1H), 7.75-7.73 (m, 1H), 7.65-7.63 (m, 1H), 7.57 (s, 1H), 7.55-7.46 (m, 8H), 7.44 (m, 1H), 7.40-7.30 (m, 3H)

Additional compounds were synthesized using appropriate intermediate compounds according to the same synthetic pathways and the same method as described herein. Analysis data of these compounds by $^1$H NMR and MS/FAB are shown in Table 1.

Other compounds not shown in Table 1 may also be synthesized based on the synthetic pathways and source materials described herein.

TABLE 1

| Comp. | $^1$H NMR (CDCl$_3$, 400 MHz) | MS/FAB found | calc. |
|---|---|---|---|
| 1 | δ = 8.26 (m, 1H), 8.06 (m, 1H), 8.04-8.02 (dd, 1H), 7.92-7.90 (m, 1H), 7.78-7.75 (m, 1H), 7.72-7.69 (m, 2H), 7.58-7.53 (m, 4H), 7.49 (s, 1H), 7.48-7.45 (m, 2H), 7.39-7.35 (m, 2H), 7.31-7.30 (m, 2H), 7.23 (d, 1H) | 434.15 | 433.15 |
| 7 | δ = 8.27 (m, 6H), 8.05-8.04 (m, 1H), 8.02 (d, 1H), 7.93 (s, 1H), 7.92-7.90 (m, 1H), 7.83-7.82 (d, 1H), 7.80-7.79 (m, 1H), 7.74-7.69 (m, 3H), 7.66-7.64 (m, 2H), 7.56-7.51 (m, 5H), 7.35-7.33 (dd, 1H), 7.32-7.27 (m, 2H) | 588.20 | 587.20 |
| 13 | δ = 8.37-8.32 (m, 1H), 8.26 (m, 1H), 8.06 (m, 1H), 8.04-8.02 (dd, 1H), 7.92-7.90 (m, 2H), 7.78-7.69 (m, 3H), 7.58-7.46 (m, 7H), 7.39-7.26 (m, 8H), 7.21 (d, 1H), 7.12-7.09 (dd, 1H) | 599.20 | 598.20 |

TABLE 1-continued

| Comp. | $^1$H NMR (CDCl$_3$, 400 MHz) | MS/FAB found | MS/FAB calc. |
|---|---|---|---|
| 14 | δ = 8.26 (m, 1H), 8.06 (m, 1H), 8.04-8.02 (dd, 1H), 7.92-7.89 (m, 2H), 7.78-7.75 (m, 2H), 7.72-7.69 (m, 3H), 7.63-7.61 (ss, 1H), 7.58-7.56 (ss, 1H), 7.55-7.48 (m, 3H), 7.40-7.29 (m, 4H), 7.23-7.20 (m, 2H) | 524.16 | 523.16 |
| 17 | δ = 8.23 (m, 1H), 8.05-8.02 (dd, 1H), 7.97-7.90 (m, 2H), 7.78-7.75 (m, 1H), 7.63-7.58 (m, 3H), 7.55-7.53 (ss, 1H), 7.51-7.42 (m, 5H), 7.39-7.37 (m, 2H), 7.35-7.33 (dd, 1H), 7.31-7.28 (m, 1H), 0.26 (s, 9H) | 506.19 | 505.19 |
| 19 | δ = 8.23 (m, 1H), 8.05-8.02 (dd, 1H), 7.97-7.90 (m, 2H), 7.80-7.75 (m, 5H), 7.66-7.61 (m, 2H), 7.55-7.47 (m, 11H), 7.44-7.40 (m, 3H), 7.35-7.32 (m, 2H) | 586.21 | 585.21 |
| 24 | δ = 8.78-8.75 (m, 4H), 8.24-8.18 (m, 3H), 8.05-8.02 (dd, 1H), 7.97-7.90 (m, 2H), 7.81-7.79 (m, 1H), 7.74-7.72 (ss, 1H), 7.69-7.61 (m, 5H), 7.54-7.46 (m, 4H), 7.42-7.38 (m, 2H), 7.35-7.31 (m, 1H) | 589.20 | 588.20 |
| 26 | δ = 8.64 (s, 1H), 8.23 (m, 1H), 8.05-8.03 (dd, 1H), 8.00-7.90 (m, 3H), 7.83-7.82 (m, 2H), 7.72 (d, 1H), 7.63-7.60 (m, 1H), 7.58-7.48 (m, 9H), 7.43-7.41 (m, 3H), 7.35-7.31 (m, 1H), 7.22-7.18 (m, 1H) | 561.19 | 560.19 |
| 33 | δ = 8.36 (m, 1H), 8.19-8.16 (m, 2H), 7.95-7.92 (m, 2H), 7.90-7.87 (dd, 1H), 7.84-7.80 (t, 1H), 7.73-7.69 (m, 4H), 7.67-7.65 (m, 1H), 7.61 (d, 2H), 7.57-7.49 (m, 4H), 7.46 (d, 1H), 7.43-7.38 (m, 2H), 7.35-7.31 (m, 1H) | 511.17 | 510.17 |
| 39 | δ = 8.78-8.75 (m, 1H), 8.36 (m, 1H), 8.21-8.16 (m, 1H), 8.11-8.09 (ss, 1H), 7.95-7.87 (m, 3H), 7.75-7.64 (m, 10H), 7.55-7.51 (m, 1H), 7.42-7.38 (m, 2H), 7.35-7.31 (m, 2H) | 589.20 | 588.20 |
| 40 | δ = 8.46-8.42 (m, 4H), 8.36 (m, 1H), 8.19-8.18 (m, 1H), 8.11-8.09 (ss, 1H), 8.01-7.97 (m, 4H), 7.95-7.93 (m, 1H), 7.90-7.88 (m, 2H), 7.72-7.69 (m, 5H), 7.66-7.64 (ss, 1H), 7.61-7.58 (m, 4H), 7.55-7.49 (m, 5H), 7.42-7.40 (m, 2H), 7.35-7.31 (m, 1H) | 741.26 | 740.26 |
| 42 | δ = 8.36 (m, 1H), 8.33-8.30 (m, 2H), 8.23-8.21 (m, 1H), 8.11-8.09 (ss, 1H), 8.00-7.98 (m, 1H), 7.95-7.86 (m, 7H), 7.72-7.69 (m, 5H), 7.64-7.58 (m, 4H), 7.55-7.49 (m, 3H), 7.42-7.38 (m, 1H), 7.35-7.31 (m, 1H) | 638.22 | 637.22 |
| 46 | δ = 8.19-8.17 (ss, 1H), 8.01-7.97 (m, 2H), 7.95-7.93 (m, 1H), 7.75-7.73 (m, 1H), 7.65-7.63 (m, 1H), 7.57 (s, 1H), 7.55-7.46 (m, 8H), 7.44 (m, 1H), 7.40-7.30 (m, 3H) | 434.15 | 433.15 |
| 50 | δ = 8.08-8.05 (m, 2H), 8.01-7.97 (m, 2H), 7.95-7.93 (m, 1H), 7.89-7.87 (ss, 1H), 7.80-7.77 (m, 2H), 7.73-7.70 (m, 2H), 7.66 (d, 1H), 7.65-7.44 (m, 14H), 7.35-7.31 (m, 1H) | 587.20 | 586.20 |
| 54 | δ = 8.78-8.75 (m, 4H), 8.19-8.18 (m, 1H), 8.01-7.89 (m, 6H), 7.72-7.63 (m, 8H), 7.51-7.38 (m, 4H), 7.35-7.31 (m, 1H) | 589.20 | 588.20 |
| 58 | δ = 8.37-8.31 (m, 1H), 8.25-8.23 (ss, 1H), 8.01-7.98 (m, 2H), 7.95-7.91 (m, 2H), 7.75-7.73 (m, 1H), 7.65-7.63 (m, 1H), 7.59-7.57 (ss, 1H), 7.53-7.44 (m, 8H), 7.40-7.26 (m, 8H), 7.21-7.19 (dd, 1H) | 599.20 | 598.20 |
| 62 | δ = 8.61 (m, 1H), 8.11-8.06 (m, 2H), 8.03-8.02 (m, 1H), 7.95-7.93 (dd, 1H), 7.80-7.76 (m, 2H), 7.62-7.37 (m, 9H), 7.31-7.29 (dd, 1H), 7.19-7.18 (d, 1H), 0.26 (s, 9H) | 522.16 | 521.16 |
| 63 | δ = 8.61 (m, 1H), 8.19-8.16 (m, 2H), 8.11-8.06 (m, 2H), 7.99 (m, 1H), 7.95-7.93 (dd, 1H), 7.86-7.82 (t, 1H), 7.78-7.72 (m, 2H), 7.64-7.52 (m, 7H), 7.46-7.38 (m, 5H) | 527.15 | 526.15 |
| 67 | δ = 8.61 (m, 1H), 8.27-8.21 (m, 5H), 8.11-8.06 (m, 2H), 7.98 (m, 1H), 7.95-7.93 (m, 2H), 7.81-7.78 (m, 2H), 7.73-7.66 (m, 4H), 7.57-7.52 (m, 5H), 7.46-7.42 (m, 1H), 7.31-7.27 (m, 2H) | 604.18 | 603.18 |
| 73 | δ = 8.61 (m, 1H), 8.37-8.31 (m, 1H), 8.11-8.06 (m, 2H), 8.03 (m, 1H), 7.95 (d, 1H), 7.93-7.91 (m, 1H), 7.80-7.77 (m, 2H), 7.58-7.42 (m, 8H), 7.38-7.26 (m, 7H), 7.18 (d, 1H), 7.12-7.09 (dd, 1H) | 615.18 | 614.18 |
| 78 | δ = 8.58 (m, 1H), 8.18-8.16 (m, 2H), 8.11-8.09 (m, 1H), 8.07-8.05 (dd, 1H), 7.92-7.90 (dd, H), 7.87 (s, 1H), 7.84-7.82 (ss, 1H), 7.80-7.78 (m, 1H), 7.73-7.71 (m, 2H), 7.67-7.65 (ss, 1H), 7.61-7.60 (m, 2H), 7.58-7.53 (m, 2H), 7.51-7.49 (ss, 1H), 7.46-7.38 (m, 4H) | 527.15 | 526.15 |
| 79 | δ = 8.58 (m, 1H), 8.11-8.05 (m, 2H), 7.92-7.90 (dd, 1H), 7.81-7.78 (m, 6H), 7.75-7.73 (m, 1H), 7.62-7.60 (ss, 1H), 7.56-7.49 (m, 10H), 7.46-7.40 (m, 3H), 7.34-7.32 (dd, 2H) | 602.19 | 601.19 |
| 85 | δ = 8.58 (m, 1H), 8.46-8.42 (m, 4H), 8.19-8.18 (m, 1H), 8.11-8.05 (m, 3H), 8.01-7.97 (m, 4H), 7.92-7.88 (m, 2H), 7.80-7.78 (m, 1H), 7.73-7.69 (m, 2H), 7.66-7.64 (ss, 1H), 7.61-7.58 (m, 5H), 7.53-7.49 (m, 5H), 7.46-7.38 (m, 3H) | 757.23 | 756.23 |
| 86 | δ = 8.64 (s, 1H), 8.58 (m, 1H), 8.11-8.05 (m, 2H), 8.00-7.98 (dd, 1H), 7.92-7.90 (dd, 1H), 7.84-7.74 (m, 6H), 7.58-7.41 (m, 10H), 7.38-7.36 (ss, 1H), 7.22-7.17 (m, 1H) | 577.17 | 576.17 |

Example 1

To manufacture an anode, a substrate with deposited ITO/Ag/ITO layers (70/1000/70 Å) was cut to a size of 50 mm×50 mm×0.5 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 1000 Å.

Then, Compound 7 as a green phosphorescent host and a compound Ir(ppy)$_3$ as a dopant were co-deposited in a weight ratio of 91:9 on the HTL to form an EML having a thickness of about 250 Å. Then, BCP as a hole blocking compound was vacuum-deposited on the EML to form a HBL having a thickness of about 50 Å. Then, Alq$_3$ was deposited on the EML to form an ETL having a thickness of 350 Å, and then LiF, which is a halogenated alkali metal, was deposited on the ETL to form an EIL having a thickness of 10 Å. Then, Mg and Ag were vacuum-deposited in a weight ratio of 90:10 on the EIL to form an electrode having a thickness of 120 Å, thereby completing the manufacture of an organic light-emitting device.

The organic light-emitting device had a driving voltage of about 5.4V at a current density of 10 mA/cm$^2$, a luminosity of 5,210 cd/m$^2$, an emission efficiency of 52.1 cd/A, and a half life-span (hr@100 mA/cm$^2$) of about 72 hours.

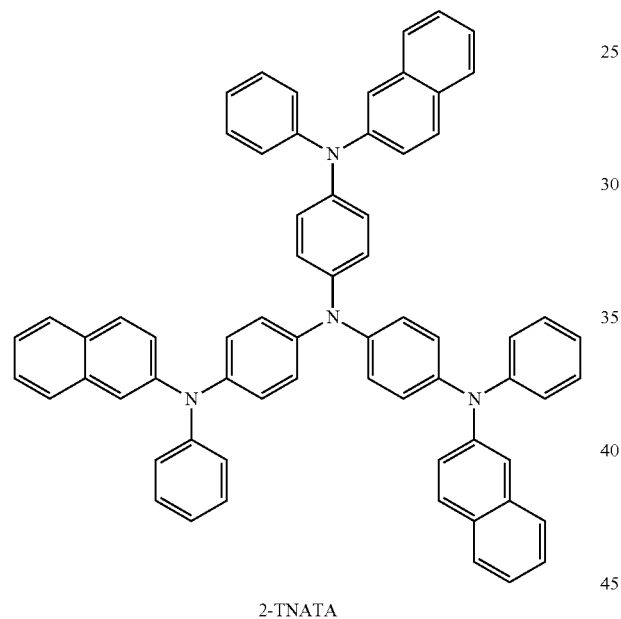

2-TNATA

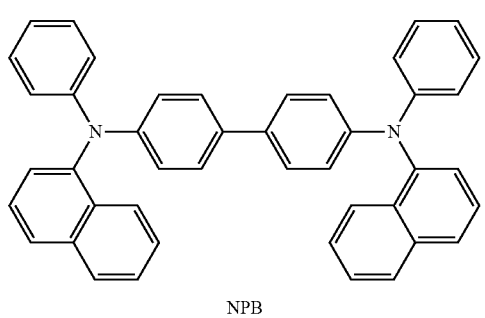

NPB

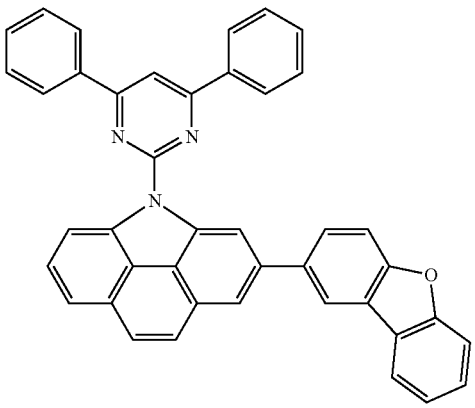

7

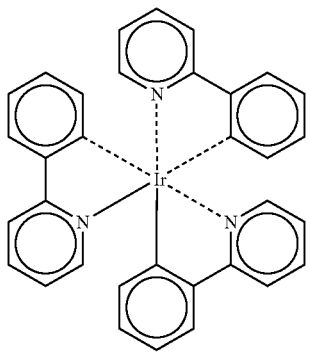

Ir(ppy)$_3$

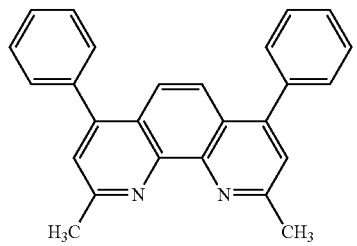

BCP

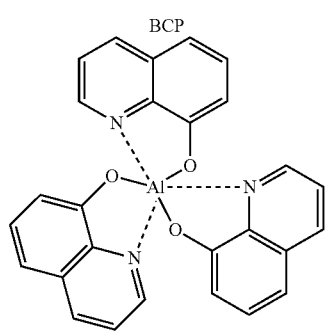

Alq$_3$

Example 2

An organic light-emitting device was manufactured in the same manner as in Example 1, except that Compound 24 instead of Compound 7 was used to form the EML. The organic light-emitting device had a driving voltage of about 5.3V at a current density of 10 mA/cm$^2$, a luminosity of 5,430 cd/m$^2$, an emission efficiency of 54.3 cd/A, and a half life-span (hr@100 mA/cm$^2$) of about 65 hours.

Example 3

An organic light-emitting device was manufactured in the same manner as in Example 1, except that Compound 39 instead of Compound 7 was used to form the EML. The organic light-emitting device had a driving voltage of about 5.3V at a current density of 10 mA/cm², a luminosity of 5,503 cd/m², an emission efficiency of 55.0 cd/A, and a half life-span (hr@100 mA/cm²) of about 58 hours.

Example 4

An organic light-emitting device was manufactured in the same manner as in Example 1, except that 4,4'-bis[N-(1-naphthyl)-N-phenylamino]biphenyl (NPB) as a HTL material was vacuum-deposited to form a HTL having a thickness of about 1,350 Å, and Compound 42 as a red phosphorescent host and BtpIr (bis(2-(2'-benzo[4,5-a]thienyl) pyridinato-N, C3')iridium acetylacetonate as a suitable dopant were co-deposited on the HTL in a weight ratio of about 94:6 to form an EML having a thickness of 400 Å.

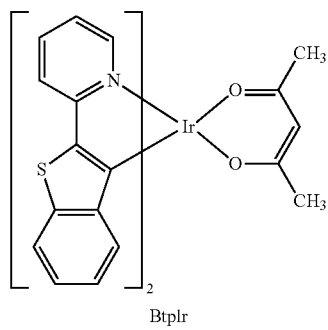

BtpIr

The organic light-emitting device had a driving voltage of about 5.6V at a current density of 10 mA/cm², a luminosity of 2,974 cd/m², an emission efficiency of 29.7 cd/A, and a half life-span (hr@100 mA/cm²) of about 113 hours.

Example 5

An organic light-emitting device was manufactured in the same manner as in Example 4, except that Compound 58 instead of Compound 42 was used to form the EML. The organic light-emitting device had a driving voltage of about 5.7V at a current density of 10 mA/cm², a luminosity of 2,742 cd/m², an emission efficiency of 27.4 cd/A, and a half life-span (hr@100 mA/cm²) of about 94 hours.

Example 6

An organic light-emitting device was manufactured in the same manner as in Example 4, except that Compound 86 instead of Compound 42 was used to form the EML. The organic light-emitting device had a driving voltage of about 5.8V at a current density of 10 mA/cm², a luminosity of 2,516 cd/m², an emission efficiency of 25.2 cd/A, and a half life-span (hr@ 100 mA/cm²) of about 87 hours.

Example 7

An organic light-emitting device was manufactured in the same manner as in Example 1, except that Compound 40 instead of Alq₃ was used to font the ETL. The organic light-emitting device had a driving voltage of about 5.2V at a current density of 10 mA/cm², a luminosity of 5,890 cd/m², an emission efficiency of 58.9 cd/A, and a half life-span (hr@100 mA/cm²) of about 109 hours.

Example 8

An organic light-emitting device was manufactured in the same manner as in Example 1, except that Compound 78 instead of Compound 40 was used to form the ETL. The organic light-emitting device had a driving voltage of about 5.1 V at a current density of 10 mA/cm², a luminosity of 5,925 cd/m², an emission efficiency of 59.3 cd/A, and a half life-span (hr@ 100 mA/cm²) of about 75 hours.

Comparative Example 1

An organic light-emitting device was manufactured in the same manner as in Example 1, except that a green phosphorescent host 4,4'-N,N'-dicarbazolbiphenyl (CBP), instead of Compound 7, was used to form the EML. The organic light-emitting device had a driving voltage of about 6.5V at a current density of 10 mA/cm², a luminosity of 3,210 cd/m², an emission efficiency of 32.1 cd/A, and a half life-span (hr@100 mA/cm²) of about 32 hours.

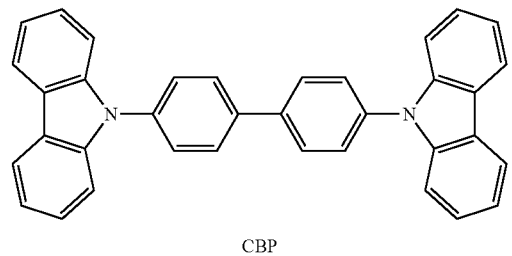 [SMILES: c1ccc2c(c1)c1ccccc1n2-c1ccc(-c2ccc(-n3c4ccccc4c4ccccc43)cc2)cc1 ; "CBP"]

CBP

Comparative Example 2

An organic light-emitting device was manufactured in the same manner as in Example 4, except that red phosphorescent host 4,4'-N,N'-dicarbazolbiphenyl (CBP), instead of Compound 42, was used to form the EML. The organic light-emitting device had a driving voltage of about 6.8V at a current density of 10 mA/cm², a luminosity of 1,643 cd/m², an emission efficiency of 16.4 cd/A, and a half life-span (hr@100 mA/cm²) of about 45 hours.

The organic light-emitting devices manufactured using the heterocyclic compounds represented by Formula 1 according to embodiments as green or red phosphorescent hosts in the EML or as ETL materials had markedly lower driving voltages and improved I-V-L characteristics with a higher efficiency, compared to those manufactured using CBP. In particular, the organic light-emitting devices according to the embodiments had markedly improved lifetimes. Main characteristics and lifetime characteristics of the organic light-emitting devices of Examples 1 to 9 and Comparative Example 1 are shown in Table 2.

TABLE 2

| | Host or ETL material | Driving voltage (V) | Current density (mA/cm$^2$) | Luminance (cd/m$^2$) | Efficiency (cd/A) | Emission color | Lifetime LT97 (hr) |
|---|---|---|---|---|---|---|---|
| Example 1 | Compound 7 | 5.4 | 10 | 5,210 | 52.1 | Green | 72 hr |
| Example 2 | Compound 24 | 5.3 | 10 | 5,430 | 54.3 | Green | 65 hr |
| Example 3 | Compound 39 | 5.3 | 10 | 5,503 | 55.0 | Green | 58 hr |
| Example 4 | Compound 42 | 5.6 | 10 | 2,974 | 29.7 | Green | 113 hr |
| Example 5 | Compound 58 | 5.7 | 10 | 2,742 | 27.4 | Red | 94 hr |
| Example 6 | Compound 86 | 5.8 | 10 | 2,516 | 25.2 | Red | 87 hr |
| Example 7 | Compound 40 | 5.2 | 10 | 5,890 | 58.9 | Green | 109 hr |
| Example 8 | Compound 78 | 5.1 | 10 | 5,925 | 59.3 | Green | 75 hr |
| Comparative Example 1 | CBP | 6.5 | 10 | 3,210 | 32.1 | Green | 32 hr |
| Comparative Example 2 | CBP | 6.8 | 10 | 1,643 | 16.4 | Red | 45 hr |

By way of summation, according to the one or more of the embodiments, a heterocyclic compound of Formula 1 may have good charge transporting capability, and thus may be used as a light-emitting material or an electron transporting material for fluorescent or phosphorescent devices of any color of red, green, blue, and white. An organic light-emitting device with high-efficiency, low-driving voltage, high luminance, and long lifetime may be manufactured using the heterocyclic compound of Formula 1.

One or more embodiments include a heterocyclic compound that has improved electrical characteristics, improved charge transporting capability, improved emission capability, and a high glass transition temperatures (Tg) enough to prevent crystallization, and thus is suitable as an electron transporting or electron injecting material for fluorescent or phosphorescent devices of any color of red, green, blue, or white, and an organic light-emitting device including the heterocyclic compound, and thus having high efficiency, low voltage, high luminance, and long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1:

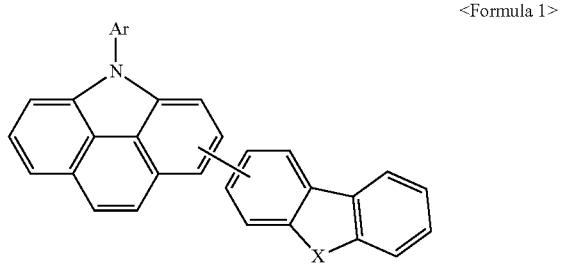

<Formula 1> wherein, in Formula 1, Ar is a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_2$-$C_{60}$ heteroaryl group, a substituted or unsubstituted $C_6$-$C_{60}$ aryl group, or a substituted or unsubstituted $C_6$-$C_{60}$ condensed polycyclic group; and X is O or S.

2. The heterocyclic compound as claimed in claim 1, wherein the heterocyclic compound of Formula 1 is a compound represented by Formula 2:

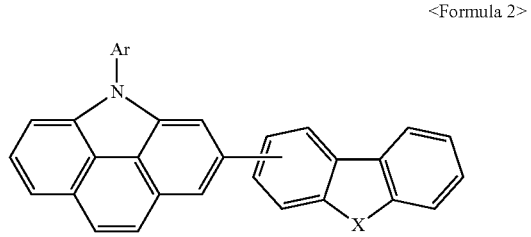

<Formula 2> wherein, in Formula 2, Ar and X are the same as defined in claim 1.

3. The heterocyclic compound as claimed in claim 1, wherein the heterocyclic compound of Formula 1 is a compound represented by Formula 3:

<Formula 3>

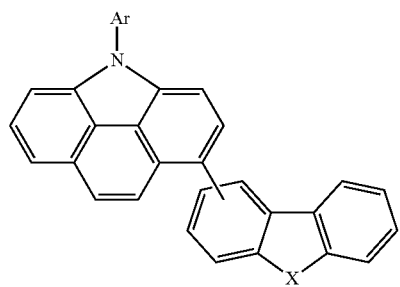

wherein, in Formula 3, Ar and X are the same as defined in claim 1.

4. The heterocyclic compound as claimed in claim 1, wherein Ar in Formula 1 is a group represented by one of Formulae 2a to 2d:

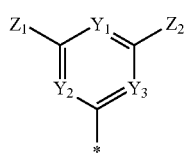

2a

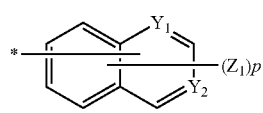

2b

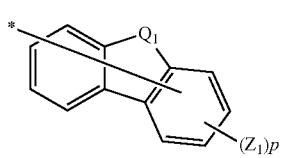

2c

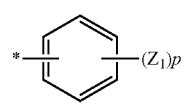

2d wherein, in Formulae 2a to 2d, $Y_1$, $Y_2$, and $Y_3$ are each independently CH or N; $Q_1$ is O or —$NR_{50}$—; $Z_1$, $Z_2$, and $R_{50}$ are each independently a hydrogen atom, a deuterium atom, a substituted or unsubstituted $C_1$-$C_{20}$ alkyl group, a $C_1$-$C_{20}$ alkylsilyl group, a $C_6$-$C_{20}$ arylsilyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, an amino group substituted with a $C_6$-$C_{20}$ aryl group or a $C_2$-$C_{20}$ heteroaryl group, a halogen group, a cyano group, a nitro group, a hydroxy group, or a carboxyl group; p is an integer from 1 to 7; and * indicates a binding site.

5. The heterocyclic compound as claimed in claim 1, wherein Ar in Formula 1 is a group represented by one of Formulae 3a to 3i:

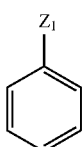

3a

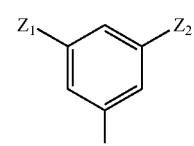

3b

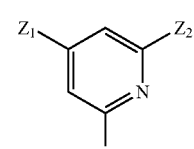

3c

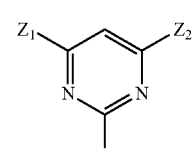

3d

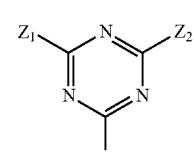

3e

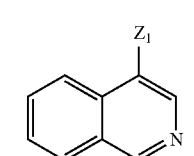

3f

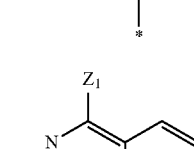

3g

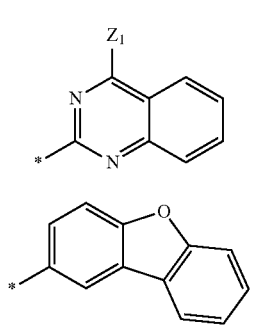

3h

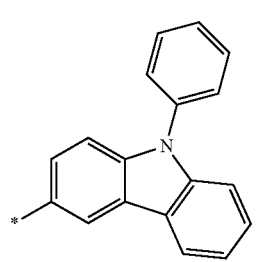

3i wherein, in Formulae 3a to 3i, $Z_1$ and $Z_2$ are each independently a hydrogen atom, a deuterium atom, a substituted or unsubstituted $C_1$-$C_{20}$ alkyl group, a $C_1$-$C_{20}$ alkylsilyl group, a $C_6$-$C_{20}$ arylsilyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, an amino group substituted with a $C_6$-$C_{20}$ aryl group or a $C_2$-$C_{20}$ heteroaryl group, a halogen group, a cyano group, a nitro group, a hydroxy group, or a carboxy group; and * indicates a binding site.

6. The heterocyclic compound as claimed in claim 1, wherein the heterocyclic compound of Formula 1 is one of the compounds represented by the following formulae:

7

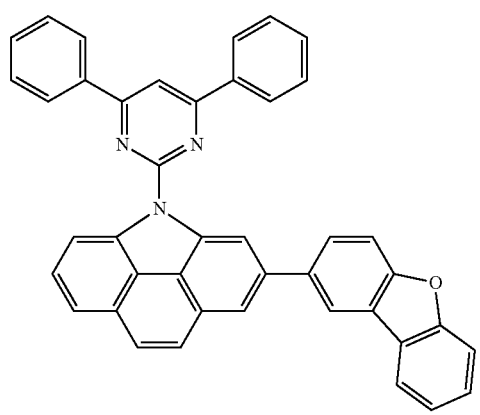

24

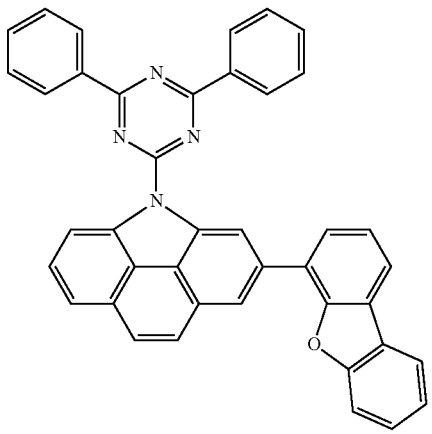

39

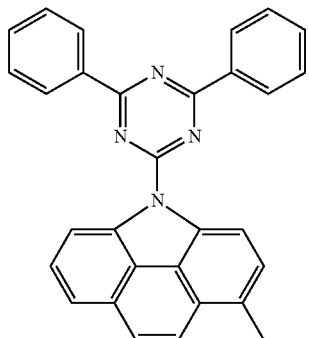

40

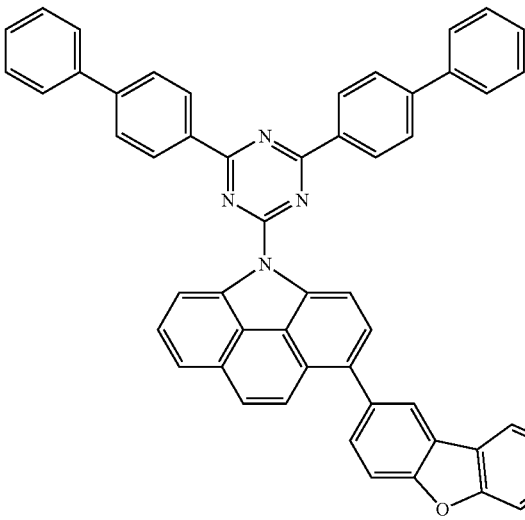

42

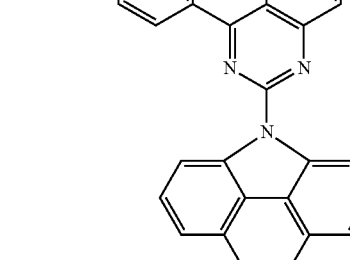

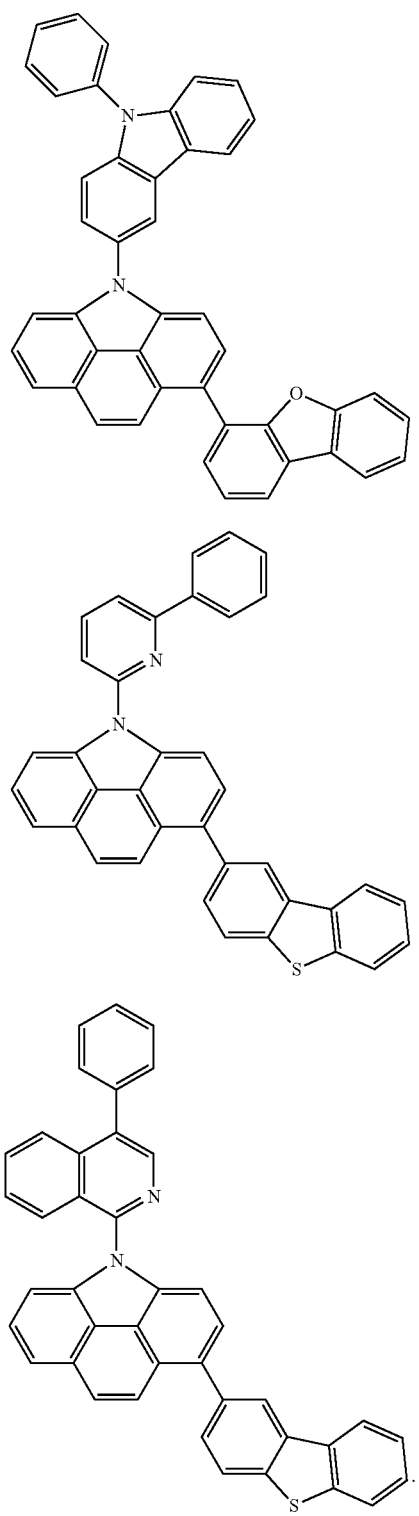

7. An organic light-emitting device, comprising:
a first electrode;
a second electrode; and
an organic layer disposed between the first electrode and the second electrode,
wherein the organic layer includes the heterocyclic compound of claim 1.

8. The organic light-emitting device as claimed in claim 7, wherein the organic layer is an emission layer or an electron transport layer.

9. The organic light-emitting device as claimed in claim 7, wherein the organic layer includes an emission layer, and further includes an electron injection layer, an electron transport layer, a functional layer having both electron injection and transport capabilities, a hole injection layer, a hole transport layer, or a functional layer having both hole injection and transport capabilities, and
the emission layer includes an anthracene-based compound, an arylamine-based compound, or a styryl-based compound.

10. The organic light-emitting device as claimed in claim 7, wherein the organic layer includes an emission layer, and further includes an electron injection layer, an electron transport layer, a functional layer having both electron injection and transport capabilities, a hole injection layer, a hole transport layer, or a functional layer having both hole injection and transport capabilities, and
the emission layer includes red, green, blue, and white emission layers, one of which includes a phosphorescent compound.

11. The organic light-emitting device as claimed in claim 10, wherein at least one of the hole injection layer, the hole transport layer, and the functional layer having both hole injection and hole transport capabilities is included in the organic layer and includes a charge-generating material.

12. The organic light-emitting device as claimed in claim 11, wherein the charge-generating material is a p-type dopant.

13. The organic light-emitting device as claimed in claim 12, wherein the p-dopant is a quinone derivative.

14. The organic light-emitting device as claimed in claim 12, wherein the p-dopant is a metal oxide.

15. The organic light-emitting device as claimed in claim 12, wherein the p-dopant is a cyano group-containing compound.

16. The organic light-emitting device as claimed in claim 7, wherein the organic layer includes an electron transport layer, and the electron transport layer further includes a metal complex.

17. The organic light-emitting device as claimed in claim 16, wherein the metal complex is a lithium (Li) complex.

18. The organic light-emitting device as claimed in claim 16, wherein the metal complex is lithium quinolate (LiQ), or Compound 203:

<Compound 203>

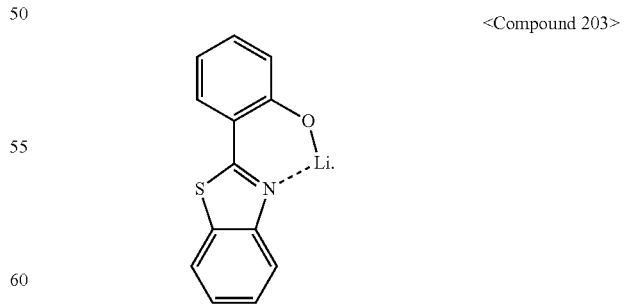

19. The organic light-emitting device as claimed in claim 7, wherein the organic layer is formed of the compound of claim 1 by a wet process.

20. A flat panel display device comprising the organic light-emitting device of claim 7, wherein the first electrode of the organic light-emitting device is electrically connected to a source electrode or a drain electrode of a thin-film transistor.

* * * * *

UNITED STATES PATENT AND TRADEMARK OFFICE
CERTIFICATE OF CORRECTION

PATENT NO. : 9,640,768 B2  
APPLICATION NO. : 14/287438  
DATED : May 2, 2017  
INVENTOR(S) : Seok-Hwan Hwang et al.

It is certified that error appears in the above-identified patent and that said Letters Patent is hereby corrected as shown below:

On the Title Page

Item (54) and in the Specification, Column 1, Lines 1-3:  
Replace: "HETEROCYCLIC COMPOUND AND ORGAINIC LIGHT-EMITTING DEVICE INCLUDING THE SAME"  
With: -- HETEROCYCLIC COMPOUND AND ORGANIC LIGHT-EMITTING DEVICE INCLUDING THE SAME --

Signed and Sealed this  
Fourth Day of June, 2019

Andrei Iancu  
*Director of the United States Patent and Trademark Office*